US012016978B2

(12) United States Patent
Antoni et al.

(10) Patent No.: US 12,016,978 B2
(45) Date of Patent: Jun. 25, 2024

(54) PROCESSES FOR IMMOBILISING BIOLOGICAL ENTITIES

(71) Applicant: CARMEDA AB, Upplands Väsby (SE)

(72) Inventors: Per Antoni, Upplands Väsby (SE); Malin Eriksson, Upplands Väsby (SE); Anna Gällhagen, Upplands Väsby (SE); Eva Koch, Upplands Väsby (SE); Daniel Nyström, Upplands Väsby (SE); Christian Porsch-Grahm, Upplands Väsby (SE); Helena Göransson, Upplands Väsby (SE)

(73) Assignee: CARMEDA AB, Upplands Väsby (SE)

( * ) Notice: Subject to any disclaimer, the term of this patent is extended or adjusted under 35 U.S.C. 154(b) by 0 days.

(21) Appl. No.: 17/871,189

(22) Filed: Jul. 22, 2022

(65) Prior Publication Data
US 2022/0378985 A1    Dec. 1, 2022

Related U.S. Application Data

(63) Continuation of application No. 16/297,064, filed on Mar. 8, 2019, now abandoned.

(30) Foreign Application Priority Data

Mar. 9, 2018  (EP) ..................... 18161058
Oct. 13, 2018  (EP) ..................... 18198422

(51) Int. Cl.
*A01N 43/36*  (2006.01)
*A61L 27/34*  (2006.01)
*A61L 31/16*  (2006.01)
*A61L 33/00*  (2006.01)
*A61L 33/06*  (2006.01)
*A61L 33/08*  (2006.01)
*C07D 207/22*  (2006.01)
*C07D 207/277*  (2006.01)

(52) U.S. Cl.
CPC ............. *A61L 31/16* (2013.01); *A61L 27/34* (2013.01); *A61L 33/0029* (2013.01); *A61L 33/0035* (2013.01); *A61L 33/0076* (2013.01); *A61L 33/068* (2013.01); *A61L 33/08* (2013.01); *A61L 2300/236* (2013.01); *A61L 2300/42* (2013.01); *A61L 2300/608* (2013.01); *A61L 2400/04* (2013.01); *A61L 2420/02* (2013.01); *A61L 2420/08* (2013.01)

(58) Field of Classification Search
CPC ...... A61L 31/16; A61L 27/34; A61L 33/0029; A61L 33/0035; A61L 33/0076; A61L 33/068; A61L 33/08; A61L 2300/236; A61L 2300/42; A61L 2300/608; A61L 2400/04; A61L 2420/02; A61L 2420/08; A61L 31/10
See application file for complete search history.

(56) References Cited

U.S. PATENT DOCUMENTS

| | | | | |
|---|---|---|---|---|
| 4,265,927 A ‡ | 5/1981 | Ericksson | ........... | A61L 33/0017 514/56 |
| 4,613,665 A ‡ | 9/1986 | Larm | ........... | C08B 37/0075 536/55.1 |
| 6,461,665 B1 ‡ | 10/2002 | Scholander | ........ | C08B 37/0075 427/407.1 |
| 6,653,457 B1 ‡ | 11/2003 | Larm | ........... | C08B 37/0075 536/124 |
| 8,501,212 B2 ‡ | 8/2013 | Vestberg | ........... | A61K 47/6957 514/56 |
| 8,658,707 B2 ‡ | 2/2014 | Xu | ........... | C08F 214/265 521/50.5 |
| 8,992,963 B2 ‡ | 3/2015 | Oscarson | ........... | A61L 33/08 514/56 |
| 9,101,696 B2 ‡ | 8/2015 | Leontein | ........... | A61L 31/10 |

(Continued)

FOREIGN PATENT DOCUMENTS

| | | |
|---|---|---|
| EP | 0086186 A1 | 8/1983 |
| EP | 0086186 A1 ‡ | 8/1983 |

(Continued)

OTHER PUBLICATIONS

Liu et al. ACS Applied Materials & Interfaces 1.1 (2009): 113-123. (Year: 2009).*
Pasche et al. (1991). A binding of Antithrombin to Immobilized Heparin Under Varying Flow Conditions. Artificial Organs, 15(6):481-491.‡
Petitou et al. (2003). 1976-1983, A Critical Period in the History of Heparin: the Discovery of the Antithrombin Binding Site. Biochimie, 85:83-89.‡
Larsen, Mette L. et al. in "Assay of plasma heparin using thrombin and the chromogenic substrate H-D-Phe-Pip-Arg-pNA" (S-2238) (Thromb. Res. 1978; 13(2):285-288).‡

(Continued)

*Primary Examiner* — Mina Haghighatian
*Assistant Examiner* — Janice Y Silverman
(74) *Attorney, Agent, or Firm* — Faegre Drinker Biddle & Reath

(57) ABSTRACT

According to the invention there is provided inter alia a process for the manufacture of a solid object having a surface comprising a layered coating of cationic and anionic polymer wherein the outer coating layer comprises an anticoagulant entity, comprising the steps of:
i) treating a surface of the solid object with a cationic polymer;
ii) treating the surface with an anionic polymer;
iii) optionally repeating steps i) and ii) one or more times;
iv) treating the surface with a cationic polymer; and
v) treating the outermost layer of cationic polymer with an anticoagulant entity, thereby to covalently attach the anticoagulant entity to the outermost layer of cationic polymer; wherein, the anionic polymer is characterized by having (a) a total molecular weight of 650 kDa-10,000 kDa; and (b) a solution charge density of >4 µeq/g; and wherein, step ii) is carried out at a salt concentration of 0.25 M-5.0 M.

12 Claims, 20 Drawing Sheets

(56) References Cited

U.S. PATENT DOCUMENTS

| | | | |
|---|---|---|---|
| 9,272,075 B2 ‡ | 3/2016 | Antoni | A61L 31/10 |
| 9,441,030 B2 ‡ | 9/2016 | Song | C07K 1/22 |
| 9,566,296 B2 ‡ | 2/2017 | Vickers | A61L 31/044 |
| 9,764,068 B2 * | 9/2017 | Leontein | A61L 33/0064 |
| 2007/0299511 A1 ‡ | 12/2007 | Gale | A61L 31/148 623/1.46 |
| 2014/0135285 A1 ‡ | 5/2014 | McKay | A61L 31/044 514/59 |
| 2014/0272232 A1 ‡ | 9/2014 | Thiagarajan | C09D 105/10 428/476.3 |
| 2017/0002098 A1 ‡ | 1/2017 | Ayoub | A61L 15/28 |
| 2017/0188922 A1 ‡ | 7/2017 | Lee | A61K 31/485 |
| 2018/0028713 A1 ‡ | 2/2018 | Agarwal | A61K 31/381 |
| 2019/0275212 A1 | 9/2019 | Antoni et al. | |
| 2019/0275213 A1 ‡ | 9/2019 | Antoni | A61L 29/085 |
| 2020/0316268 A1 ‡ | 10/2020 | Antoni | A61L 33/08 |

FOREIGN PATENT DOCUMENTS

| | | | | |
|---|---|---|---|---|
| EP | 0086187 A1 ‡ | 8/1983 | | |
| EP | 0086187 A1 | 8/1983 | | |
| EP | 0495820 B1 ‡ | 7/1992 | | |
| EP | 0495820 B1 | 5/1995 | | |
| WO | 96/37241 A1 | 11/1996 | | |
| WO | 02/85500 A1 | 10/2002 | | |
| WO | WO-2002085500 A1 ‡ | 10/2002 | | |
| WO | 2009/064372 A2 | 5/2009 | | |
| WO | WO-2009064372 A2 ‡ | 5/2009 | | A61K 31/727 |
| WO | 2010/029189 A2 | 3/2010 | | |
| WO | WO-2010029189 A2 ‡ | 3/2010 | | A61L 27/34 |
| WO | 2011/110684 A1 | 9/2011 | | |
| WO | WO-2011110684 A1 ‡ | 9/2011 | | A61K 47/58 |
| WO | 2012/123384 A1 | 9/2012 | | |
| WO | WO-2012123384 A1 ‡ | 9/2012 | | A61K 47/50 |

OTHER PUBLICATIONS

Smith, R. L., & Gilkerson, E. (1979). Quantification of Glycosaminoglycan Hexosamine Using 3-Methyl-2-Benzothiazolone Hydrazone Hydrochloride. Analytical Biochemistry, 98:478-480.‡

Thunberg, L. et al. (1980). The Molecular Size of the Antithrombin-Binding Sequence in Heparin. Elsevier/North-Holland Biomedical Press, FEBS Letters, 117(1):203-206.‡

Rodahl, M. et al. (1995). Quartz crystal microbalance setup for frequency and Q-factor measurements in gaseous and liquid environments. Review of Scientific Environments, 66(7): p. 3924-3930.‡

Farris, Stefano et al. (2012). Charge Density Quantification of Polyelectrolyte Polysaccharides by Conductomeric Titration: An Analytical Chemistry Experiment. J. Chem. Educ., 89(1):121-124.‡

Lappegard, K. T. et al. (2008). The artificial surface-induced whole blood inflammatory reaction revealed by increases in a series of chemokines and growth factors is largely complement dependent. J. Biomed Mater Res, 87A:129-135.‡

George, O. "1.4 Molecular Weight." in: Principles of Polymerization, Third edition (New York, John Wiley & Sons, 1991), p. 24.‡

Bitter, T., & Muir, H. M. (1962). Analytical Biochemistry, 4:330-334.‡

Ekdahl, Kristina N. et al. (2013). Advances in Experimental Medicine and Biology, 735:257-270.‡

Andersson, J. et al. (2003). Optimal heparin surface concentration and antithrombin binding capacity as evaluated with human non-anticoagulated blood in vitro. J. Biomed Mater Res, 67A:458-466.‡

Velnar et al., "The Wound Healing Process: an Overview of the Cellular and Molecular Mechanisms", The Journal of International Medical Research, vol. 37, 2009, pp. 1528-1542.‡

Ai et al., "Biomedical Applications of Electrostatic Layer-by-Layer Nano-Assembly of Polymers, Enzymes, and Nanoparticles", Cell Biochemistry and Biophysics, vol. 39, 2003, pp. 23-43.‡

Luxbacher, Thomas "The streaming potential technique" in: The Zeta Potential for Solid Surface Analysis (Austria, Anton Paar GmbH, 2014), pp. 1-6, 20-34.‡

Schoeler, B. et al., Macromolecules 2002, 35, 889-897 (Year: 2002).‡

Hirsh, J. and Levine, MN. Blood, 1992, 79: 1-17 (Year: 1992).‡ https://www.sigmaaldrich.com/content/dam/sigma-aldrich/docs/Sigma-Aldrich/Datasheet/1/31396dat.pdf (Year: 2015).‡ https://www.chemicalbook.com/productchemicalpropertiescb9339022_en.htm (Year: 2017).‡

International Preliminary Report on Patentability received for PCT Patent Application No. PCT/EP2019/055845, dated Sep. 24, 2020, 11 pages.

International Search Report and Written Opinion received for PCT Patent Application No. PCT/EP2019/055845, dated Jun. 3, 2019, 12 pages.

Search Report and Written Opinion received for Singapore Patent Application No. 11202008063Y, dated Mar. 7, 2022, 8 pages.

* cited by examiner

‡ imported from a related application

PROCESSES FOR IMMOBILISING BIOLOGICAL ENTITIES

CROSS REFERENCE TO RELATED APPLICATIONS

This application is a continuation of U.S. application Ser. No. 16/297,064, filed Mar. 8, 2019, which claims the benefit of priority to EP 18161058.5, filed Mar. 9, 2018, and also claims the benefit of priority to EP 18198422.0, filed Oct. 3, 2018, the disclosure of which are hereby incorporated by reference in their entireties.

FIELD OF THE INVENTION

The present invention relates to processes for preparing solid objects having surface coatings comprising biological entities. In particular, the present invention relates to processes for preparing improved surface coatings comprising anticoagulant entities such as heparin and certain products obtained thereby.

BACKGROUND OF THE INVENTION

When a medical device is implanted in the body or is in contact with body fluids, a number of different reactions are set into motion, some of them resulting in inflammation and some in the coagulation of the blood in contact with the device surface. In order to counteract these serious adverse effects, the well-known anticoagulant compound heparin has for a long time been administered systemically to patients before the medical device is implanted into their body, or when it is in contact with their body fluids, in order to provide an antithrombotic effect.

Thrombin is one of several coagulation factors, all of which work together to result in the formation of thrombi at a surface in contact with the blood. Antithrombin (also known as antithrombin III) ("ATM") is the most prominent coagulation inhibitor. It neutralizes the action of thrombin and other coagulation factors and thus restricts or limits blood coagulation. Heparin dramatically enhances the rate at which antithrombin inhibits coagulation factors. Heparin cofactor II ("HCII") is another coagulation factor which rapidly inhibits thrombin in the presence of heparin.

Systemic treatment with high doses of heparin is, however, often associated with serious side-effects of which bleeding is the predominant. Another rare, but serious complication of heparin therapy is the development of an allergic response called heparin induced thrombocytopenia (HIT) that may lead to thrombosis (both venous and arterial). High-dose systemic heparin treatment e.g. during surgery also requires frequent monitoring of the activated clotting time (used to monitor and guide heparin therapy) and the corresponding dose adjustments as necessary.

Therefore, solutions have been sought where the need for a systemic heparinization of the patient would be unnecessary or can be limited. It was thought that this could be achieved through a surface modification of the medical devices using the anticoagulative properties of heparin and other anticoagulants. Thus, a number of more or less successful technologies have been developed where a layer of heparin is attached to the surface of the medical device seeking thereby to render the surface thromboresistant. For devices where long-term bioactivity is required, heparin should desirably be resistant to leaching and degradation.

Heparin is a polysaccharide carrying negatively charged sulfate and carboxylic acid groups on the saccharide units. Ionic binding of heparin to polycationic surfaces was thus attempted, but the surface modifications suffered from lack of stability resulting in lack of function, as the heparin leached from the surface. Thereafter, different surface modifications have been prepared wherein the heparin has been covalently bound to groups on the surface.

One of the most successful processes for rendering a medical device thromboresistant has been the covalent binding of a heparin fragment to a modified surface of the device. The general method and improvements thereof are described in various patent documents (see EP0086186A1, EP0086187A1, EP0495820B1 and U.S. Pat. No. 6,461,665B1 each of which is incorporated herein by reference in its entirety).

These documents describe the preparation of a heparinized surface by reacting heparin modified to bear a terminal aldehyde group with a surface on a medical device which has been modified to bear primary amino groups. An intermediate Schiff base is formed which is reduced in situ to form a stable secondary amine linker, thereby covalently immobilizing the heparin.

Further methods for covalently attaching heparin to a surface while retaining its activity are described in WO2010/029189A2, WO2011/110684A1 and WO2012/123384A1 (each of which is incorporated herein by reference in its entirety).

The anticoagulant entity is typically immobilized on a surface which has been treated with one or more layers of polymer or a complex, rather than being immobilized directly onto the surface of the solid object.

EP0086187A1 describes a surface modified substrate with a complex absorbed thereto, wherein the complex is of a polymeric cationic surfactant that contains primary amino nitrogen functionality as well as secondary and/or tertiary amino functionality, and a dialdehyde that has 1~4 carbon atoms between the two aldehyde groups. An anionic compound may additionally be bonded to said complex, and optionally additional cationic and anionic alternating compounds.

EP0495820B1 describes a method for modifying the surface of a substrate, comprising the steps of: (a) adsorbing a polyamine of a high average molecular weight and crosslinking said polyamine with crotonaldehyde; (b) then adsorbing on the surface of the crosslinked polyamine a layer of an anionic polysaccharide; (c) optionally repeating steps (a) and (b) one or more times; and (d) adsorbing on the anionic polysaccharide layer, or on the outermost layer of anionic polysaccharide, a layer of non-crosslinked polyamine providing free primary amino groups. In a subsequent step, a biologically active chemical entity carrying a functional group reactive with the free primary amino groups can be bound to the non-crosslinked polyamine, e.g. heparin.

However, there remains a need for improved surface coatings comprising anticoagulant entities such as heparin, in particular for coatings in which the biological activity of the anticoagulant entity is maintained or enhanced. Such improved surface coatings have potential utility in medical devices and other articles which would benefit from an anticoagulant surface.

The present inventors have discovered that, surprisingly, the nature of the surface upon which an anticoagulant entity is immobilized can significantly impact characteristics of the coating, in particular the resulting biological activity of the anticoagulant entity. In particular, when an anticoagulant entity is immobilized on a surface of a solid object comprising a layered coating of cationic and anionic polymer, careful modulation of the nature and the conditions of the application of the anionic polymer layer(s) can improve the resulting characteristics of the coating of the solid object including, for example, the thromboresistant properties that it may have.

SUMMARY OF THE INVENTION

In one aspect, the present invention provides a process for the manufacture of a solid object having a surface comprising a layered coating of cationic and anionic polymer wherein the outer coating layer comprises an anticoagulant entity, comprising the steps of:
  i) treating a surface of the solid object with a cationic polymer;
  ii) treating the surface with an anionic polymer;
  iii) optionally repeating steps i) and ii) one or more times;
  iv) treating the surface with a cationic polymer; and
  v) treating the outermost layer of cationic polymer with an anticoagulant entity, thereby to covalently attach the anticoagulant entity to the outermost layer of cationic polymer;
  wherein,
  the anionic polymer is characterized by having (a) a total molecular weight of 650 kDa-10,000 kDa; and (b) a solution charge density of >4 µeq/g;
  and wherein,
  step ii) is carried out at a salt concentration of 0.25 M-5.0 M.

In a further aspect, the present invention provides a process for the manufacture of a solid object having a surface comprising a layered coating of cationic and anionic polymer wherein the outer coating layer comprises an anticoagulant entity, comprising the steps of:
  i) treating a surface of the solid object with a cationic polymer;
  ii) treating the surface with an anionic polymer;
  iii) optionally repeating steps i) and ii) one or more times;
  iv) treating the surface with a cationic polymer; and
  v) treating the outermost layer of cationic polymer with an anticoagulant entity, thereby to covalently attach the anticoagulant entity to the outermost layer of cationic polymer;
  wherein,
  the anionic polymer is a polymer comprising $-SO_3^-$ groups,
  the anionic polymer is characterized by having (a) a total molecular weight of 650 kDa-10,000 kDa; and (b) a sulfur content between 10% and 25% by weight of the anionic polymer;
  and wherein,
  step ii) is carried out at a salt concentration of 0.25 M-5.0 M.

In a further aspect, the present invention provides a process for the manufacture of a solid object having a surface comprising a layered coating of cationic and anionic polymer wherein the outer coating layer comprises an anticoagulant entity, comprising the steps of:
  i) treating a surface of the solid object with a cationic polymer;
  ii) treating the surface with an anionic polymer;
  iii) optionally repeating steps i) and ii) one or more times;
  iv) treating the surface with a cationic polymer; and
  v) treating the outermost layer of cationic polymer with an anticoagulant entity, thereby to covalently attach the anticoagulant entity to the outermost layer of cationic polymer;
  wherein,
  the anionic polymer is characterized by having a total molecular weight of 650 kDa-10,000 kDa;
  the anionic polymer is dextran sulfate;
  and wherein,
  step ii) is carried out at a salt concentration of 0.25 M-5.0 M.

DETAILED DESCRIPTION OF THE INVENTION

Solid Object

Figure 1:
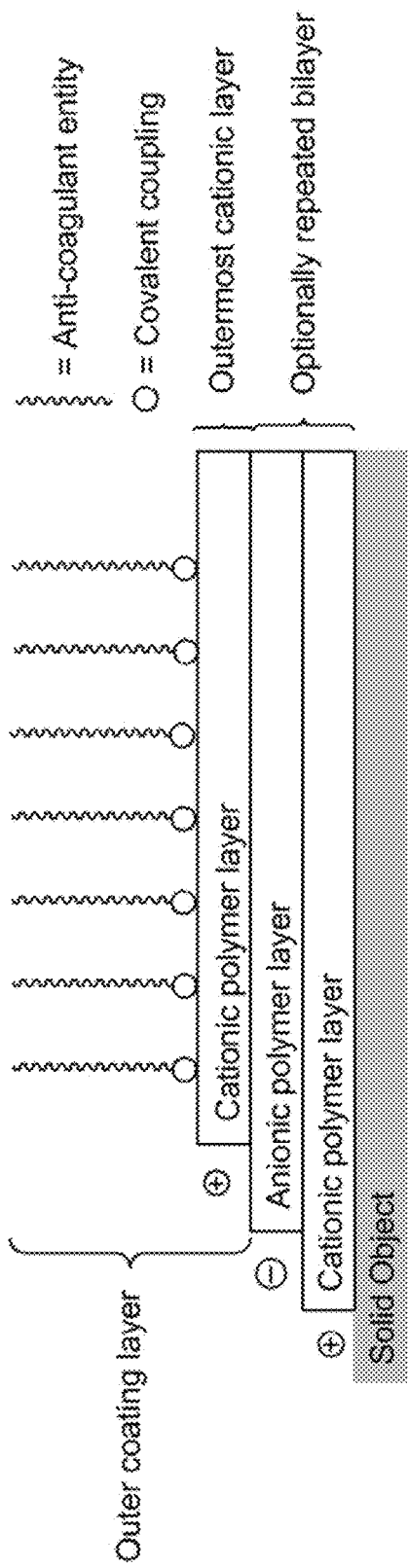
FIG. 1: shows an example coating of the invention with a single bilayer.

Any solid object can potentially be coated using the process of the invention, although such coatings and processes are particularly useful for medical devices, analytical devices, separation devices, and other industrial articles including membranes.

Solid objects may have a thromboresistant surface. In certain embodiments of the invention, the thromboresistant surface may exhibit a direct pharmacologic inhibition of the coagulation response by immobilization of an anticoagulant entity. In certain embodiments of the invention, the thromboresistant surface does not cause any appreciable clinically-significant adverse reactions such as thrombosis, haemolysis, platelet, leukocyte, and complement activation, and/or other blood-associated adverse event when in contact with blood.

In the art, the terms "hemocompatible", "non-thrombogenic", "anti-thrombogenic" and the like can typically be interpreted as being equivalent to the term "thromboresistant".

In one embodiment, the solid object is a medical device. When the solid object is a medical device, it is suitably a thromboresistant medical device. Thus, in one embodiment the solid object is a thromboresistant medical device. For the purposes of this patent application, the term "medical device" refers to intracorporeal or extra-corporeal devices but more usually to intracorporeal medical devices.

Intracorporeal medical devices are devices which are used within the anatomy e.g. within the vasculature or other body lumen, space or cavity, typically to provide a therapeutic effect. Intracorporeal devices may be of long-term or temporary use. Devices of long-term use are left, in part or in whole, in the anatomy after the immediate surgical procedure to deliver them e.g. stents or stent-grafts. Devices for temporary or short-term use include those which are transiently inserted into a treatment region (i.e. inserted and then removed in the same surgical procedure), such as a medical balloon. In one embodiment, the solid object is an intracorporeal medical device.

Examples of intracorporeal medical devices which can be permanent or temporary intracorporeal medical devices include stents including bifurcated stents, balloon-expandable stents, self-expanding stents, neurovascular stents and flow diverting stents, stent-grafts including bifurcated stent-grafts, grafts including vascular grafts and bifurcated grafts, sheaths including retractable sheaths such as interventional diagnostic and therapeutic sheaths, large and standard bore endovascular delivery sheaths, arterial introducer sheaths with and without hemostatic control and with or without steering, micro-introducer sheaths, dialysis access sheaths, guiding sheaths, and percutaneous sheaths, dilators, occluders such as vascular occluders, embolic filters, embolectomy devices, catheters, artificial blood vessels, blood indwelling monitoring devices, valves including artificial heart valves, pacemaker electrodes, guidewires, cardiac leads, cardiopulmonary bypass circuits, cannulae, plugs, drug delivery devices, balloons, tissue patch devices, blood pumps, patches, lines such as chronic infusion lines or arterial lines, placement wires, devices for continuous subarachnoid infusions, feeding tubes, CNS shunts such as ventriculopleural shunts, ventriculoatrial (VA) shunts, ventriculoperitoneal (VP) shunts, ventricular atrial shunts, portosystemic shunts and shunts for ascites.

Examples of catheters include, but are not limited to, microcatheters, central venous catheters, peripheral intravenous catheters, hem odialysis catheters, catheters such as coated catheters include implantable venous catheters, tunnelled venous catheters, coronary catheters useful for angiography, angioplasty, or ultrasound procedures in the heart or in peripheral veins and arteries, catheters containing spectroscopic or imaging capabilities, hepatic artery infusion catheters, CVC (central venous catheters), peripheral intravenous catheters, peripherally inserted central venous catheters (PIC lines), flow-directed balloon-tipped pulmonary artery catheters, total parenteral nutrition catheters, chronic dwelling catheters (e.g. chronic dwelling gastrointestinal catheters and chronic dwelling genitourinary catheters), peritoneal dialysis catheters, CPB catheters (cardiopulmonary bypass), urinary catheters and microcatheters (e.g. for intracranial application).

In one embodiment, the solid object is an intracorporeal medical device selected from the group consisting of stents, stent-grafts, sheaths, dilators, occluders, valves, embolic filters, embolectomy devices, catheters, artificial blood vessels, blood indwelling monitoring devices, valves, pacemaker electrodes, guidewires, cardiac leads, cardiopulmonary bypass circuits, cannulae, plugs, drug delivery devices, balloons, tissue patch devices, blood pumps, patches, lines, placement wires, devices for continuous subarachnoid infusions, feeding tubes and shunts. In a specific embodiment, the solid object is a stent or a stent-graft.

In one embodiment, said intracorporeal medical device can be used in neurological, peripheral, cardiac, orthopaedic, dermal, or gynaecologic applications. In one embodiment, said stents can be used in cardiac, peripheral or neurological applications. In one embodiment, said stent-grafts can be used in cardiac, peripheral or neurological applications. In one embodiment, said sheaths can be used in carotid, renal, transradial, transseptal, paediatric or micro applications.

Examples of extracorporeal medical devices are blood treatment devices, and transfusion devices. In one embodiment, said intracorporeal medical device can be used in neurological, peripheral, cardiac, orthopaedic, dermal, or gynaecologic applications. In one embodiment the extracorporeal medical device is an oxygenator. In another embodiment the extracorporeal medical device is a filter capable of removing viruses, bacteria, sepsis-causing pro-inflammatory cytokines and toxins.

A membrane can be, for example, a haemodialysis membrane.

An analytical device can be, for example, a solid support for carrying out an analytical process such as chromatography or an immunological assay, reactive chemistry or catalysis. Examples of such devices include slides, beads, well plates and membranes.

A separation device can be, for example, a solid support for carrying out a separation process such as protein purification, affinity chromatography or ion exchange. Examples of such devices include filters and columns.

The solid object may comprise or be formed of a metal, a synthetic or naturally occurring organic or inorganic polymer, a ceramic material, a protein-based material, or a polysaccharide-based material, inter alia.

Suitable metals include, but are not limited to, biocompatible metals such as titanium, stainless steel, high nitrogen stainless steel, cobalt, chromium, nickel, tantalum, niobium, gold, silver, rhodium, zinc, platinum, rubidium, copper and magnesium, and combinations (alloys) thereof. Suitable alloys include cobalt-chromium alloys such as L-605, MP35N, Elgiloy, titanium alloys including nickel-titanium alloys (such as Nitinol), tantalum alloys, niobium alloys (e.g. Nb-1% Zr), and others.

In one embodiment, said biocompatible metal is a nickel-titanium alloy, such as Nitinol.

Synthetic or naturally occurring organic or inorganic polymers include polyolefins, polyesters (e.g. polyethylene terephthalate and polybutylene terephthalate), polyester ethers, polyester elastomer copolymers (e.g. such as those available from DuPont in Wilmington, Del. under the tradename of HYTREL.RTM), fluorine-containing polymers, chlorine-containing polymers (e.g. polyvinyl chloride (PVC)), block copolymer elastomers (e.g. such as those copolymers having styrene end blocks, and midblocks formed from butadiene, isoprene, ethylene/butylene, ethylene/propene), block copolymers (e.g. styrenic block copolymers such as acrylonitrile-styrene and acrylonitrile-butadiene-styrene block copolymers, or block copolymers wherein the particular block copolymer thermoplastic elastomers in which the block copolymer is made up of hard segments of a polyester or polyamide and soft segments of polyether), polyurethanes, polyamides (e.g. nylon 12, nylon 11, nylon 9, nylon 6/9 and nylon 6/6), polyether block amides (e.g. PEBAX®), polyetheresteramide, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylam ide, polyacrylic acid, polystyrenes, polytetrafluoroethylene, poly(methyl)methacrylates, polyacrylonitriles, poly(vinylacetates), poly(vinyl alcohols), polyoxymethylenes, polycarbonates, phenolics, amino-epoxy resins, cellulose-based plastics, and rubber-like plastics, bioresorbables (e.g. poly(D,L-lactide) and polyglycolids, and copolymers thereof and copolymers thereof), derivatives thereof and mixtures thereof. Combinations of these materials can be employed with and without cross-linking. Some of these classes are available both as thermosets and as thermoplastic polymers. As used herein, the term "copolymer" shall be used to refer to any polymer formed from two or more monomers, e.g. 2, 3, 4, 5 and so on and so forth.

Fluorinated polymers (fluorine-containing polymers) include fluoropolymers such as expanded polytetrafluoroethylene (ePTFE), polytetrafluoroethylene (PTFE), fluorinated ethylene-propylene (FEP), perfluorocarbon copolymers (such as tetrafluoroethylene perfluoroalkylvinyl ether (TFE/PAVE) copolymers and copolymers of tetrafluoroethylene (TFE) and perfluorom ethyl vinyl ether (PMVE)), and combinations of the above with and without crosslinking between the polymer chains.

In one embodiment, the solid object comprises a polyether-block-amide, such as PEBAX®. In another embodiment, the solid object comprises a chlorine-containing polymer (e.g. PVC) or a fluorine-containing polymer (e.g. ePTFE).

Polymeric substrates may optionally be blended with fillers and/or colorants. Thus, suitable substrates include pigmented materials such as pigmented polymeric materials.

Ceramic substrates may include, but are not limited to, silicone oxides, aluminium oxides, alumina, silica, hydroxyapatites, glasses, calcium oxides, polysilanols, and phosphorous oxide.

Protein-based materials include silk and wool. Polysaccharide-based materials include agarose and alginate.

Anticoagulant Entity

An anticoagulant entity is an entity capable of interacting with mammalian blood to prevent or alleviate coagulation or thrombus formation.

Anticoagulant entities include heparin moieties, dermatan sulfate moieties, dermatan disulfate moieties, hirudin, eptifibatide, tirofibran, urokinase, D-Phe-Pro-Arg chloromethylketone, an RGD peptide-containing compound, AZX100 (a cell peptide that mimics HSP20, Capstone Therapeutics Corp., USA), platelet receptor antagonists, anti-throm bin antibodies, anti-platelet receptor antibodies, aspirin, prostaglandin inhibitors, platelet inhibitors (e.g. clopidogrel, nitric oxide (NO), prostaglandines and abciximab), antiplatelet peptides, coumadins (i.e. vitamin K antagonists of the 4-hydroxycoumarin class e.g. warfarin), argatroban, thrombomodulin, anticoagulant proteins, anticoagulant enzymes (e.g. apyrase). In one embodiment, the anticoagulant entity is selected from the group consisting of heparin moieties, dermatan sulfate moieties and dermatan disulfate moieties.

In one embodiment, the anticoagulant entity is a glycosaminoglycan. In one embodiment, the anticoagulant entity is a thrombin inhibitor.

The term "heparin moiety" refers to a heparin molecule, a fragment of a heparin molecule, a derivative of a heparin molecule or an analogue of a heparin molecule.

In one embodiment, the anticoagulant entity is a heparin moiety. Suitably the heparin moiety is selected from the group consisting of full length heparin (native heparin), an alkali metal or alkaline earth metal salt of heparin (e.g. sodium heparin (e.g. Hepsal or Pularin), potassium heparin (e.g. Clarin), lithium heparin, calcium heparin (e.g. Calciparine) or magnesium heparin (e.g. Cutheparine)), a low molecular weight heparin (e.g. ardeparin sodium, tinzaparin or dalteparin), heparan sulfate, a heparinoid, a heparin-based compound, heparin having a hydrophobic counter-ion, a synthetic heparin composition capable of antithrombin-mediated inhibition of factor Xa (e.g. a "fondaparinux" composition (e.g. Arixtra from GlaxoSmithKline)) and a synthetic heparin derivative comprising at least the active pentasaccharide sequence from heparin (see for example Petitou et al., Biochimie, 2003, 85(1-2):83-9). Additional heparin moieties include heparin modified by means of e.g. mild nitrous acid degradation (U.S. Pat. No. 4,613,665A, incorporated herein by reference in its entirety) or periodate oxidation (U.S. Pat. No. 6,653,457B1, incorporated herein by reference in its entirety) and other modification reactions known in the art where the activity of the heparin moiety is preserved. Heparin moieties also include such moieties bound to a linker or spacer as described below. In one embodiment, the heparin moiety is full length heparin.

Low molecular weight heparins may be prepared by, for example, oxidative depolymerisation, enzymatic degradation or deaminative cleavage.

In one embodiment the heparin moiety is a fragment of heparin. Fragments of heparin may be produced using techniques known in the art. Suitably the fragments are fragments of native heparin produced by a process comprising degrading (e.g. fragmentation of) native heparin. As illustrated in Example 2e below, fragments of heparin may be prepared by partial nitrous acid cleavage of native heparin, optionally followed by fractionation by gel chromatography. Alternatively, fragments of heparin may be synthetically produced. Synthetic production may include chemo enzymatic and/or traditional organic chemistry methods.

Figure 23:
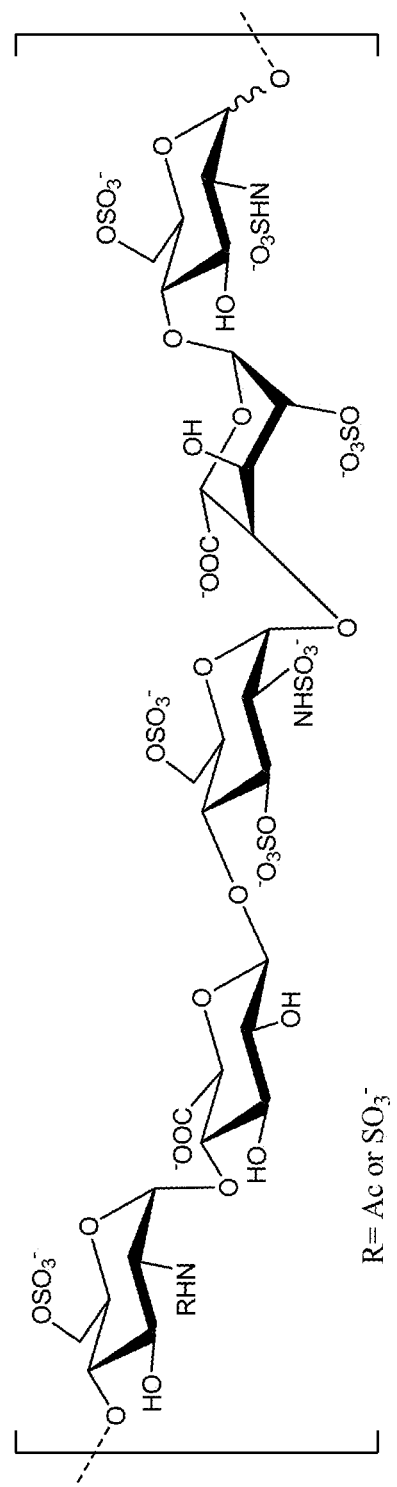
FIG. 23: shows the active pentasaccharide sequence of heparin

The anticoagulant activity of heparin is mainly dependent on an antithrombin (AT) binding pentasaccharide sequence (the 'active pentasaccharide sequence', or 'active sequence'; see FIG. 23). Suitably the fragment of heparin contains the active pentasaccharide sequence.

Fragments of heparin may, for example, have a length of 5-30 e.g. 5-20 e.g. 5-18 e.g. 5-17 e.g. 5-10 e.g. 6-10 saccharide residues. Alternatively, fragments of heparin may, for example, have a length of 6-30 e.g. 6-20 e.g. 6-18 e.g. 6-17 saccharide residues.

U.S. Pat. No. 6,461,665B1 (Scholander; incorporated herein by reference) discloses improving the anti-thrombogenic activity of surface-immobilized heparin by treating the heparin prior to immobilization. The improvement is achieved by treating the heparin at elevated temperature or at elevated pH, or by contacting the heparin with nucleophilic catalysts such as amines, alcohols, thiols or immobilized amino, hydroxyl or thiol groups.

The anticoagulant entity is covalently immobilized on the surface of the solid object, therefore does not substantially elute or leach from the solid object. As discussed below, the anticoagulant entity can be covalently immobilized by various methods.

The anticoagulant entity is covalently attached to the outermost layer of cationic polymer.

The anticoagulant entity is suitably end-point attached to the cationic polymer, particularly when the anticoagulant entity is a heparin moiety. Thus, in one embodiment, the anticoagulant entity is an end-point attached anticoagulant moiety. In a particular embodiment, the anticoagulant entity is an end-point attached heparin moiety. Where applicable, the anticoagulant entity is preferably connected through its reducing end. Thus, in one embodiment, the anticoagulant entity is connected through its reducing end. In a particular embodiment, the anticoagulant entity is an end-point attached heparin moiety connected through its reducing end (sometimes referred to as position C1 of the reducing terminal). The advantage of end-point attachment, especially reducing end-point attachment, is that the biological activity of the anticoagulant entity (for example the heparin moiety) is maximized due to enhanced availability e.g. the antithrombin interaction sites as compared with attachment elsewhere in the anticoagulant entity (e.g. heparin moiety).

A representative end-point attachment process is described in EP0086186B1 (Larm; incorporated herein by reference in its entirety) which discloses a process for the covalent binding of oligomeric or polymeric organic substances to substrates of different types containing primary amino groups. The substance to be coupled, which may be heparin, is subjected to degradation by diazotization to form a substance fragment having a free terminal aldehyde group. The substance fragment is then reacted through its aldehyde group with the amino group of the substrate to form a Schiff's base, which is then converted (via reduction) to a secondary amine. The advantage of end-point attachment of heparin, especially reducing end point attachment (as described above in EP0086186B1), is that the biological activity of the heparin moiety is maximized due to enhanced availability of the antithrombin interaction sites as compared with attachment elsewhere in heparin moiety.

The anticoagulant entity may be covalently attached to the outermost layer of cationic polymer via a linker. Thus, in one embodiment, the anticoagulant entity is covalently attached via a linker.

In one embodiment, the linker comprises a secondary amine. A representative procedure for covalently bonding a heparin moiety to a polymer via a secondary amine is described in EP0086186B1.

In one embodiment, the linker comprises a secondary amide. A representative procedure for covalently bonding a heparin moiety to a polymer via an amidation reaction involving N-succinimidyl 3-(2-pyridyldithio)propionate (SPDP) or 1-ethyl-3-(3-dimethylaminopropyl)-carbodiimide (EDC) is set out in WO2012/123384A1 (incorporated herein by reference in its entirety).

In one embodiment, the linker comprises a 1,2,3-triazole. A representative procedure for covalently bonding a heparin moiety to a polymer via a 1,2,3-triazole linkage is described in WO2010/029189A2 (Carmeda A B, incorporated herein by reference in its entirety). The document describes the azide- or alkyne-functionalization of a polyimine; the preparation of alkyne- and azide-functionalized heparin (both native and nitrous acid degraded heparin); and reactions to link the derivatised heparin to the derivatised polymer via a 1,2,3-triazole linker.

In one embodiment, the linker comprises a thioether. A representative procedure for covalently bonding a heparin moiety to a polymer via a thioether linkage is described in WO2011/110684A1 (Carmeda A B et al., incorporated herein by reference in its entirety).

Cationic Polymer

The cationic polymer may be a straight chain polymer but is more usually a branched chain polymer such as a hyperbranched polymer. In one embodiment the cationic polymer is a branched cationic polymer. The cationic polymer is optionally cross-linked. In one embodiment, the cationic polymer comprises primary/secondary amine groups. In one embodiment, the cationic polymer is a polyamine, which is optionally cross-linked. The cationic polymer (e.g. polyamine), suitably has molecular weight of 5 kDa-3,000 kDa, such as 5 kDa-2,000 kDa, 5 kDa-1,500 kDa, 5 kDa-1,000 kDa, 5 kDa-800 kDa, 5 kDa-500 kDa, 5 kDa-300 kDa or 5 kDa-200 kDa or 800 kDa-3,000 kDa. When the cationic polymer (e.g. polyamine) is cross-linked, it is suitably cross-linked using an aldehyde cross-linker such as crotonaldehyde and/or glutaraldehyde. In one embodiment, the cationic polymer is a polyalkyleneimine e.g. polyethyleneimine.

The cationic polymer forms part of a layer-by-layer coating of cationic polymer and anionic polymer, which is formed by alternately treating the surface of the solid object with layers of cationic and anionic polymer. A bilayer is defined herein as one layer of cationic polymer and anionic polymer. In the layer-by-layer coating, the cationic polymer is typically applied before the anionic polymer i.e. a surface of the solid object is typically first treated with a first layer of cationic polymer (step i) in claim 1), upon which a first layer of anionic polymer is applied (step ii) in claim 1). Depending on the number of bilayers required, further layers of cationic polymer and anionic polymer may be applied (step iii) in claim 1). When the final (which may be also the first) bilayer of cationic and anionic polymer is completed, a layer of cationic polymer is then applied (corresponding to step iv) in claim 1). This layer (i.e. the outermost layer) of cationic polymer is then treated with an anticoagulant entity, so as to covalently attach the anticoagulant entity to the layer of cationic polymer. Thus, the outer coating layer of cationic polymer can be said to "comprise" an anticoagulant entity. In the layer-by-layer coating, the innermost layer is a layer of cationic polymer and the outermost layer is an outer coating layer of cationic polymer to which the anticoagulant entity is covalently attached (see FIG. 1).

In one embodiment, the cationic polymer of step i) is a polyamine, which is optionally cross-linked. In one embodiment, the cationic polymer of step iv) is a polyamine, which is optionally cross-linked. In one embodiment, the cationic polymer of step i) is the same as the cationic polymer of step iv).

WO2012/123384A1 (Gore Enterprise Holdings, Inc. et al., incorporated herein by reference in its entirety) discloses a device with a coating comprising a plurality of hyperbranched polymer molecules bearing anticoagulant entities, in particular heparin. Such hyperbranched polymer molecules may be utilised in the outermost layer of cationic polymer i.e. such hyperbranched polymers may be used as the cationic polymer of step iv), and then modified to bear anticoagulant entities in step v).

Anionic Polymer

Anionic polymers suitable for the invention carry deprotonated functional groups from the groups consisting of —COON, —SO$_3$H and —PO$_3$H$_2$. Thus, in one embodiment, the anionic polymer is a polymer comprising groups selected from —CO2$^-$, —SO$_3$$^-$, —PO$_3$H$^-$ and —PO$_3$$^{2-}$. Suitably, the anionic polymer is a polymer comprising —SO$_3$$^-$ groups. More suitably, the deprotonated functional groups carried by the anionic polymer consist of —SO$_3$$^-$ groups.

The anionic polymer is suitably an anionic glycosaminoglycan or polysaccharide. The anionic characteristics of the polymer typically derive from carboxylate or sulfate groups along the polymer chain. Thus, in one embodiment, the anionic polymer is a glycosaminoglycan or polysaccharide bearing carboxylate and/or sulfate groups, in particular a glycosaminoglycan bearing carboxylate and/or sulfate groups. The anionic polymer may be branched or unbranched. In one embodiment, the anionic polymer and the anticoagulant entity are not the same.

In one embodiment, the anionic polymer is optionally cross-linked.

In one embodiment, the anionic polymer is selected from the group consisting of dextran sulfate, hyaluronic acid, poly(2-acrylamido-2-methyl-1-propanesulfonic acid), poly (2-acrylamido-2-methyl-1-propanesulfonic acid-co-acrylonitrile) acrylonitrile, poly(acrylic acid), polyanetholesulfonic acid, poly(sodium 4-styrenesulfonate), poly(4-styrenesulfonic acid-co-maleic acid), poly(vinyl sulfate), polyvinylsulfonic acid and salts thereof. Suitably, the anionic polymer is dextran sulfate.

Dextran sulfate is a sulfated polymer of anhydroglucose. The degree of sulfation and consequently the sulfur content of the dextran sulfate can vary.

In some embodiments the sulfur content is between 10% and 25% by weight, e.g. the sulfur content is between 15% and 20% by weight.

In one embodiment, the anionic polymer is characterized by having a total molecular weight of 750 kDa-10,000 kDa, such as 1,000 kDa-10,000 kDa. In one embodiment, the anionic polymer is characterized by having a total molecular weight of 650 kDa-1,000 kDa, e.g. 750 kDa-1,000 kDa. In one embodiment, the anionic polymer is characterized by having a total molecular weight of 1,000 kDa-4,500 kDa e.g. 2,000 kDa-4,500 kDa. In one embodiment, the anionic polymer is characterized by having a total molecular weight of 4,500 kDa-7,000 kDa. In one embodiment, the anionic polymer is characterized by having a total molecular weight of 7,000 kDa-10,000 kDa. Suitably, the total molecular weight of the anionic polymer is measured according to Evaluation Method G.

In one embodiment, the anionic polymer is characterized by having a solution charge density of between >4 µeq/g and 7 µeq/g, such as between >5 µeq/g and 7 µeq/g. Suitably, the solution charge density of the anionic polymer is measured according to Evaluation Method H.

Coating Bilayer(s) of Cationic and Anionic Polymer

The process of the invention involves forming a solid object having a surface comprising a layered coating of cationic and anionic polymer. As explained above, a bilayer is defined herein as one layer of cationic and anionic polymer (see FIG. 1).

The layered coating comprises one or more coating bilayers, e.g. 2 or more, 3 or more, 4 or more, 5 or more, 6 or more, 7 or more, 8 or more, 9 or more or 10 or more coating bilayers. When more than one coating bilayer is applied, steps i) and ii) are repeated i.e. step iii) is not optional. In one embodiment of the process of the invention, step iii) is not optional. In this embodiment, step iii) is repeated as many times as is necessary to achieve the required number of coating bilayers e.g. 1 time, 2 times, 3 times, 4 times, 5 times, 6 times, 7 times, 8 times or 9 times. In one embodiment of the process of the invention, in step iii), steps i) and ii) are repeated between 1 and 10 times, such 1, 2, 3, 4, 5 or 6 times.

When step iii) is not optional (i.e. when steps i) and ii) are repeated one or more times) the precise process conditions of each repeat need not be identical (e.g. the salt type and/or concentration used in treating the surface with an anionic polymer in step ii) need not be identical in each repetition). In an embodiment, the process conditions (e.g. the salt type and/or concentration used in treating the surface with an anionic polymer in step ii)) are identical in each repetition.

Process Steps

The present invention provides a process for the manufacture of a solid object having a surface comprising a layered coating of cationic and anionic polymer wherein the outer coating layer comprises an anticoagulant entity, comprising the steps of:

i) treating a surface of the solid object with a cationic polymer;
ii) treating the surface with an anionic polymer;
iii) optionally repeating steps i) and ii) one or more times;
iv) treating the surface with a cationic polymer; and
v) treating the outermost layer of cationic polymer with an anticoagulant entity, thereby to covalently attach the anticoagulant entity to the outermost layer of cationic polymer;
wherein,
the anionic polymer is characterized by having (a) a total molecular weight of 650 kDa-10,000 kDa; and (b) a solution charge density of >4 µeq/g;
and wherein,
step ii) is carried out at a salt concentration of 0.25 M-5.0 M.

It should be noted that steps i)-v) are carried out sequentially in the given order i.e. each of steps i)-iv) is implicitly followed by "and then". This does not preclude one or more additional steps being carried out between each of specified steps i)-v). Thus, in one embodiment, the process of the invention additionally comprises a step between step i) and step ii), between step ii) and step iii), between step iii) and step iv) or between step iv) and step v).

It should be understood, for example, that washing steps may be performed between the specified process steps.

The present inventors have found that, surprisingly, the salt concentration of step ii) (i.e. the salt concentration present when the anionic polymer coating layer(s) is (are) applied) impacts the resulting characteristics of the coating of the solid object, in particular the thromboresistant properties of the final solid object. The present inventors have found that when step ii) is carried out at a salt concentration of 0.25 M-5.0 M, the resulting characteristics of the coating of the solid object, in particular the thromboresistant properties of the final solid object can be improved, as shown in Examples 2a and 3a.

In one embodiment, step ii) is carried out at a salt concentration of 0.25 M-4.0 M, such as 0.25 M-3.0 M, 0.5 M-3.0 M, 1.0 M-3.0 M, 1.5 M-3.0 M, 0.25 M-1.5 M, 0.5 M-1.5 M, 0.75 M-1.5 M or 1.0 M-2.0 M, in particular, at a salt concentration of 1.0 M-3.0 M, such as 1.0 M-2.0 M or 0.75 M-1.5 M or 1.5 M-3.0 M.

In one embodiment, the salt is an inorganic salt. Suitably, the salt is selected from the group consisting of a sodium salt, a potassium salt, a magnesium salt, a calcium salt, a lithium salt, an ammonium salt, a barium salt and a strontium salt.

In one embodiment, the salt is an inorganic sodium salt.

In one embodiment, the salt is selected from the group consisting of sodium chloride, sodium sulfate, sodium hydrogen phosphate and sodium phosphate.

In one embodiment, the salt is sodium chloride.

In one embodiment, the salt is not sodium chloride.

In one embodiment, the salt is sodium chloride at a concentration of 0.25 M-3.0 M, e.g. 0.5 M-3.0 M, e.g. 1.0 M-3.0 M, e.g. 1.5 M-3.0 M.

In one embodiment, the salt is sodium sulfate at a concentration of 0.25 M-1.5 M, e.g. 0.5 M-1.5 M, e.g. 0.75 M-1.5 M.

In one embodiment, the salt is sodium hydrogen phosphate at a concentration of 0.25 M-3.0 M, e.g. 0.5 M-3.0 M, e.g. 1.0 M-3.0 M, e.g. 1.0 M-2.0 M.

In one embodiment, the salt is sodium phosphate at a concentration of 0.25 M-3.0 M e.g. 0.5 M-3.0 M e.g. 1.0 M-3.0 M. e.g. 1.0 M-2.0 M.

Prior to step i) (treating the surface of the solid object with a cationic polymer) the surface of the solid object can optionally be subjected to a pre-treatment step.

The pre-treatment step may be a cleaning step to improve adhesion and surface coverage of the subsequent coating. Suitable cleaning agents include solvents such as alcohols, solutions with high pH like solutions comprising a mixture of an alcohol and an aqueous solution of a hydroxide compound (e.g. sodium hydroxide), sodium hydroxide solution as such, solutions containing tetramethyl ammonium hydroxide (TMAH), acidic solutions like Piranha (a mixture of sulfuric acid and hydrogen peroxide), basic Piranha solution, and other oxidizing agents including combinations of sulfuric acid and potassium permanganate or different types of peroxysulfuric acid or peroxydisulfuric acid solutions (also as ammonium, sodium, and potassium salts), or by subjecting the solid object to plasma in air, argon or nitrogen atmosphere or combinations thereof.

Thus, in one embodiment, the process of the invention additionally comprises a pre-treatment step before step i). Suitably, the pre-treatment step is a cleaning step.

Alternatively, a pre-treatment step may involve overlaying the surface of the solid object to be coated according to steps i)-v) with a material such as a polymer or primer coating layer, prior to the application of steps i)-v). This "preparative" coating layer could, for example, allow the surface of the solid object to be coated to be "sculpted" or modified to create a desired surface topography or texture in order to optimize the subsequent layered coating process. The additional coating layer could also improve the adherence of the subsequent layered coating, in particular helping to maintain its integrity during processing. An example of such a priming coating layer on a solid object is a coating layer applied using chemical vapour deposition (CVD). Another example of such a priming coating layer on a solid object is a coating of polydopamine or an analogue thereof.

In one embodiment, the pre-treatment step comprises treating a surface of the solid object with a polymer selected from the group consisting of a polyolefin, polyisobutylene, ethylene-α-olefin copolymers, an acrylic polymer, an acrylic copolymer, polyvinyl chloride, polyvinyl methyl ether, polyvinylidene fluoride, polyvinylidene chloride, a fluoropolymer (e.g. expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference in its entirety, as well as combinations thereof), polyacrylonitrile, a polyvinyl ketone, polystyrene, polyvinyl acetate, an ethylene-methyl methacrylate copolymer, an acrylonitrile-styrene copolymer, an ABS resin, Nylon 12, a block copolymer of Nylon 12, polycaprolactone, a polyoxymethylene, a polyether, an epoxy resin, a polyurethane, rayon-triacetate, cellulose, cellulose acetate, cellulose butyrate, cellophane, cellulose nitrate, cellulose propionate, a cellulose ether, carboxymethyl cellulose, a chitin, polylactic acid, polyglycolic acid, a polylactic acid-polyethylene oxide copolymer, polyethylene glycol, polypropylene glycol, polyvinyl alcohol, an elastomeric polymer such as silicone (e.g. polysiloxane or a substituted polysiloxane), a polyurethane, a thermoplastic elastomer, an ethylene vinyl acetate copolymer, a polyolefin elastomer, an EPDM rubber, and mixtures thereof.

In one embodiment, is provided a process for the manufacture of a solid object as described herein, consisting of steps i)-v) as defined herein i.e. the solid object has no additional coating layers beyond those resulting from steps i)-v).

A solid object coated according to the process of the invention may be sterilized. Suitable sterilization processes include, but are not limited to, sterilization using ethylene oxide, vapour hydrogen peroxide, plasma phase hydrogen peroxide, dry heat, autoclave steam sterilization, chlorine dioxide sterilization, gamma ray sterilization or electron beam sterilization.

As shown in Example 7, solid objects coated according to the process of the invention were subjected to increased temperature and humidity and retained their thromboresistant properties. Conditions of increased temperature and humidity can act as a mimic for the rigorous conditions of sterilization, in particular ethylene oxide sterilization.

Hence, a solid object coated according to the process of the invention is expected to be stable to sterilization.

Coating Properties

Typically, the coating layer will have an average total thickness of about 10 nm to about 1000 nm, e.g. about 10 nm to about 800 nm, e.g. about 10 mM to about 500 nm, about 10 nm to about 400 nm, about 10 nm to about 300 nm, about 10 nm to about 200 nm or about 10 nm to about 100 nm. Coating thickness can be measured using a suitable coating thickness analyser or gauge, by using X-ray photoelectron spectroscopy with depth profiling (see Evaluation Method J) or by using Quartz Crystal Microbalance with Dissipation (see Evaluation Method 0). Suitably, the coating thickness is measured using Evaluation Method 0.

In one embodiment, the solid object coated according to the process of the invention has anticoagulant entity activity (in particular heparin activity) of at least 1 pmol/cm$^2$ of surface e.g. at least 2 pmol/cm$^2$ of surface, at least 3 pmol/cm$^2$ of surface, at least 4 pmol/cm$^2$ of surface, or at least 5 pmol/cm$^2$ of surface for binding of ATIII, suitably measured according to Evaluation Method B.

In one embodiment, a thromboresistant surface of the solid object has anticoagulant entity activity (in particular heparin activity) of at least 1 pmol/cm$^2$ of surface e.g. at least 2 pmol/cm$^2$ of surface, at least 3 pmol/cm$^2$ of surface, at least 4 pmol/cm$^2$ of surface, or at least 5 pmol/cm$^2$ of surface for binding of ATIII, suitably measured according to Evaluation Method B.

In one embodiment, the solid object coated according to the process of the invention has anticoagulant entity activity (in particular heparin activity) of at least 5 pmol/cm$^2$ of surface e.g. at least 12 pmol/cm$^2$ of surface, at least 20 pmol/cm$^2$ of surface, at least 50 pmol/cm$^2$ of surface for binding of HCII, suitably measured according to Evaluation Method M.

In one embodiment, a thromboresistant surface of the solid object has anticoagulant entity activity (in particular heparin activity) of at least 5 pmol/cm$^2$ of surface e.g. at least 12 pmol/cm$^2$ of surface, at least 20 pmol/cm$^2$ of surface, at least 50 pmol/cm$^2$ of surface for binding of HCII, suitably measured according to Evaluation Method M.

In one embodiment, the solid object coated according to the process of the invention has blood contact performance of at least 80% preserved platelets, e.g. at least 85% preserved platelets, e.g. at least 90% preserved platelets, suitably measured according to Evaluation Method E.

In one embodiment, a thromboresistant surface of a solid object has blood contact performance of at least 80% preserved platelets, e.g. at least 85% preserved platelets, e.g. at least 90% preserved platelets, suitably measured according to Evaluation Method E.

In one embodiment, the solid object coated according to the process of the invention has an F1+2 value of <10,000 pmol/L e.g. less than 7,500 pmol/L, less than 5,000 pmol/L or less than 4,000 pmol/L, suitably measured according to Evaluation Method F.

In one embodiment, a thromboresistant surface of a solid object has an F1+2 value of <10,000 pmol/L, less than 7,500 pmol/L, less than 5,000 pmol/L or less than 4,000 pmol/L, suitably measured according to Evaluation Method F.

In one embodiment, the anticoagulant entity is a heparin moiety, wherein the solid object has heparin concentration of at least 1 µg/cm$^2$, e.g. at least 2 µg/cm$^2$, at least 4 µg/cm$^2$, at least 5 µg/cm$^2$, or at least 6 µg/cm$^2$, suitably measured according to Evaluation Method A.

Figure 22:
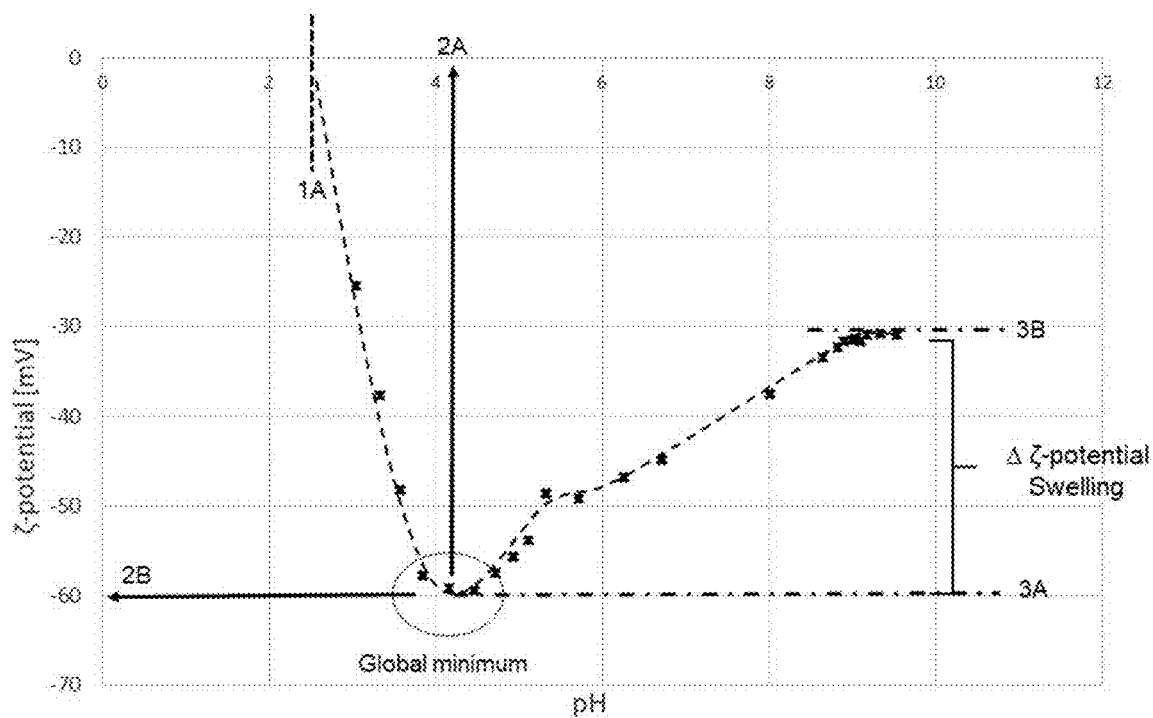
FIG. 22: shows a typical zeta potential profile of a solid object of the present invention.

Zeta potential profiles of the solid objects coated according to the process of the invention may suitably be measured using Evaluation Method D. A typical zeta potential profile of a solid object coated according to the process of the invention is shown in FIG. 22 which indicates the various parameters that can be used qualify and define a zeta potential profile, in particular the isoelectric point (IEP) (1A) which corresponds to a particular pH value at which the zeta potential is 0 mV; the global minimum of the curve corresponding to the pH (2A) at which the zeta potential (2B) is at a minimum; and the delta value (Δ) which corresponds to the difference between the zeta potential at the global minimum (3A) and the zeta potential at pH 9 (3B).

Similar zeta (ξ) potential profiles have been obtained for solid objects coated according to the process of the invention with dextran sulfates 4-7 as can be seen in FIGS. 7-13 (Examples 4a and 4b). Thus, the zeta potential profile can be viewed as a potential fingerprint for solid objects coated according to the process of the invention, at least in its preferred aspects. According to this potential fingerprint, preferably the IEP (1A) is below pH 3, the global minimum of the curve (2A) is below pH 5 and the delta value i.e. the difference between the zeta potential at the global minimum (3A) and the zeta potential at pH 9 (3B), is at least 20 mV. These parameters are suitably measured according to Evaluation Method D.

Solid objects coated according to the process of the invention suitably have a zeta potential profile with an isoelectric point (IEP) of below pH 3 because the acidic nature of the heparin dominates on the coated surface. By contrast, inert polymer materials will have an IEP at approximately pH 4. The swelling properties of samples having acidic groups is seen towards the alkaline region. The swelling will force the shear plane in the direction of the bulk and lower absolute zeta potential values (closer to 0 mV) should be obtained. A high delta value of the zeta potential correlates with high thromboresistant properties e.g. when evaluated according to Evaluation Methods B, M, E or F. Furthermore, higher salt concentration used in the process of the invention gives lower absolute zeta potential values in the alkaline regions irrespective of the salt tested, yet again correlating with the antithrom bin binding values. Without being limited by theory, this can potentially be explained with an increased access of antithrom bin to heparin molecules in a coating that can undergo swelling.

Therapeutic Methods

Solid objects, in particular medical devices coated according to the process of the invention as described hereinabove are of use in medical therapy.

In one aspect of the invention is provided a solid object (in particular a medical device) coated according to the process of the invention described hereinabove for use in treating tissue in the human or animal body. The tissue to be treated includes any body cavity, space, or hollow organ passage(s) such as blood vessels, the urinary tract, the intestinal tract, nasal cavity, neural sheath, intervertebral regions, bone cavities, oesophagus, intrauterine spaces, pancreatic and bile ducts, rectum, and those previously intervened body spaces that have implanted vascular grafts, stents, prosthesis, or other type of medical implants. In yet another aspect of the invention, a solid object (e.g. medical device) coated according to a process of the invention as described hereinabove may be deployed to treat aneurysms in the brain.

The coated solid object (in particular medical device) as described herein can be of use in the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters.

In one embodiment is provided a solid object (in particular a medical device such as a stent, graft or stent-graft) coated according to the process of the invention as described hereinabove for use in the prevention or treatment of stenosis or restenosis in a blood vessel of the human body. In another embodiment is provided a solid object (in particular a medical device such as a stent, graft or stent-graft) coated according to the process of the invention as described hereinabove for use in the prevention or treatment of stenosis or restenosis in a blood vessel of the human body, where previously placed eluting constructs have failed. In another embodiment, a solid object (in particular a medical device such as a stent, graft or stent-graft) coated according to the process of the invention as described hereinabove can be used to establish or maintain arteriovenous access sites, e.g. those used during kidney dialysis. In a further embodiment, a solid object (in particular a medical device such as a stent, graft or stent-graft e.g. a vascular graft) coated according to the process of the invention described hereinabove may be used to redirect flow around an area of blockage or vessel narrowing. In another embodiment, a solid object (in particular a medical device such as a stent, graft or stent-graft) coated according to the process of the invention as described hereinabove may be deployed to restore patency to an area of diseased vessel or to exclude an aneurysm. In yet another embodiment, a sold object (in particular a medical device such as a stent, graft or stent-graft) coated according to the process of the invention as described hereinabove may be deployed to reinforce a diseased vessel following angioplasty. In yet another embodiment, a solid object (in particular a medical device such as a stent, graft or stent-graft) coated according to the process of the invention as described hereinabove may be deployed in the brain using balloon assisted or coil assisted procedures.

In one embodiment, a solid object (in particular a medical device) coated according to the process of the invention as described hereinabove can be used for Percutaneous Transluminal Angioplasty (PTA) in patients with obstructive disease of the peripheral arteries.

In another aspect of the invention is provided a method for the prevention or treatment of stenosis or restenosis which comprises implanting into said blood vessel in the human body a solid object (in particular a medical device) coated according to the process of the invention as described hereinabove.

Further Embodiments of the Invention

Embodiments and preferences described above with respect to the process of the invention apply equally to embodiments below.

In one embodiment is provided a process for the manufacture of a solid object having a surface comprising a layered coating of cationic and anionic polymer wherein the outer coating layer is a layer comprising cationic polymer, comprising the steps of:
  i) treating a surface of the solid object with a cationic polymer;
  ii) treating the surface with an anionic polymer;
  iii) optionally repeating steps i) and ii) one or more times; and
  iv) treating the surface with a cationic polymer;
wherein,
  the anionic polymer is characterized by having (a) a total molecular weight of 650 kDa-10,000 kDa; and (b) a solution charge density of >4 µeq/g;
  and wherein,
  step ii) is carried out at a salt concentration of 0.25 M-5.0 M.

In one embodiment is provided a solid object having a surface comprising a layered coating of cationic and anionic polymer, wherein the outer coating layer is a layer comprising cationic polymer;
  and wherein the anionic polymer is characterized by having (a) a total molecular weight of 650 kDa-10,000 kDa; and (b) a solution charge density of >4 µeq/g.

In one embodiment is provided a process for the manufacture of a solid object having a surface comprising a layered coating of cationic and anionic polymer wherein the outer coating layer is a layer comprising anionic polymer, comprising the steps of:
  i) treating a surface of the solid object with a cationic polymer;
  ii) treating the surface with an anionic polymer;
  iii) optionally repeating steps i) and ii) one or more times;
wherein,
  the anionic polymer is characterized by having (a) a total molecular weight of 650 kDa-10,000 kDa; and (b) a solution charge density of >4 µeq/g;
  and wherein,
  step ii) is carried out at a salt concentration of 0.25 M-5.0 M.

In one embodiment is provided a solid object having a surface comprising a layered coating of cationic and anionic polymer, wherein the outer coating layer is a layer comprising anionic polymer; and wherein the anionic polymer is characterized by having (a) a total molecular weight of 650 kDa-10,000 kDa; and (b) a solution charge density of >4 µeq/g.

In one embodiment is provided a process for the manufacture of a solid object having a surface comprising a layered coating of cationic and anionic polymer wherein the outer coating layer comprises an anticoagulant entity, consisting of the steps of:
  i) treating a surface of the solid object with a cationic polymer;
  ii) treating the surface with an anionic polymer;
  iii) optionally repeating steps i) and ii) one or more times;
  iv) treating the surface with a cationic polymer; and
  v) treating the outermost layer of cationic polymer with an anticoagulant entity, thereby to covalently attach the anticoagulant entity to the outermost layer of cationic polymer;
wherein,
  the anionic polymer is characterized by having (a) a total molecular weight of 650 kDa-10,000 kDa; and (b) a solution charge density of >4 µeq/g;
  and wherein,
  step ii) is carried out at a salt concentration of 0.25 M-5.0 M.

In one embodiment is provided a solid object having a surface comprising a layered coating of cationic and anionic polymer, wherein the outer coating layer is a layer comprising cationic polymer to which is covalently bound an anticoagulant entity; and wherein the anionic polymer is characterized by having (a) a total molecular weight of 650 kDa-10,000 kDa; and (b) a solution charge density of >4 µeq/g. Suitably the anionic polymer is applied to the surface at a salt concentration of 0.25 M-5.0 M, such as 0.25 M-4.0 M or 0.25 M-3.0 M.

In one embodiment is provided a solid object having a surface comprising a layered coating of cationic and anionic polymer, wherein the outer coating layer is a layer comprising cationic polymer to which is covalently bound an anticoagulant entity; and wherein the anionic polymer is characterized by having (a) a total molecular weight of 650 kDa-1,000 kDa; and (b) a solution charge density of >4 µeq/g. Suitably the anionic polymer is applied to the surface at a salt concentration of 0.25 M-5.0 M, such as 0.25 M-4.0 M or 0.25 M-3.0 M.

In one embodiment is provided a solid object having a surface comprising a layered coating of cationic and anionic polymer, wherein the outer coating layer is a layer comprising cationic polymer to which is covalently bound an anticoagulant entity; and wherein the anionic polymer is characterized by having (a) a total molecular weight of 1,000 kDa-4,500 kDa; and (b) a solution charge density of >4 µeq/g. Suitably the anionic polymer is applied to the surface at a salt concentration of 0.25 M-5.0 M, such as 0.25 M-4.0 M or 0.25 M-3.0 M.

In one embodiment is provided a solid object having a surface comprising a layered coating of cationic and anionic polymer, wherein the outer coating layer is a layer comprising cationic polymer to which is covalently bound an anticoagulant entity; and wherein the anionic polymer is characterized by having (a) a total molecular weight of 4,500 kDa-7,000 kDa; and (b) a solution charge density of >4 µeq/g. Suitably the anionic polymer is applied to the surface at a salt concentration of 0.25 M-5.0 M, such as 0.25 M-4.0 M or 0.25 M-3.0 M.

In one embodiment is provided a solid object having a surface comprising a layered coating of cationic and anionic polymer, wherein the outer coating layer is a layer comprising cationic polymer to which is covalently bound an anticoagulant entity; and wherein the anionic polymer is characterized by having (a) a total molecular weight of 7,000 kDa-10,000 kDa; and (b) a solution charge density of >4 µeq/g. Suitably the anionic polymer is applied to the surface at a salt concentration of 0.25 M-5.0 M, such as 0.25 M-4.0 M or 0.25 M-3.0 M.

In one embodiment is provided a process for the manufacture of a solid object having a surface comprising a layered coating of cationic and anionic polymer wherein the outer coating layer comprises an anticoagulant entity, comprising the steps of:
i) treating a surface of the solid object with a cationic polymer;
ii) treating the surface with an anionic polymer;
iii) optionally repeating steps i) and ii) one or more times;
iv) treating the surface with a cationic polymer; and
v) treating the outermost layer of cationic polymer with an anticoagulant entity, thereby to covalently attach the anticoagulant entity to the outermost layer of cationic polymer;
wherein,
the anionic polymer is a polymer comprising $—SO_3^-$ groups,
the anionic polymer is characterized by having (a) a total molecular weight of 650 kDa-10,000 kDa; and (b) a sulfur content between 10% and 25% by weight of the anionic polymer;
and wherein,
step ii) is carried out at a salt concentration of 0.25 M-5.0 M.

In one embodiment is provided a process for the manufacture of a solid object having a surface comprising a layered coating of cationic and anionic polymer wherein the outer coating layer comprises an anticoagulant entity, comprising the steps of:
i) treating a surface of the solid object with a cationic polymer;
ii) treating the surface with an anionic polymer;
iii) optionally repeating steps i) and ii) one or more times;
iv) treating the surface with a cationic polymer; and
v) treating the outermost layer of cationic polymer with an anticoagulant entity, thereby to covalently attach the anticoagulant entity to the outermost layer of cationic polymer;
wherein,
the anionic polymer is characterized by having a total molecular weight of 650 kDa-10,000 kDa;
the anionic polymer is dextran sulfate;
and wherein,
step ii) is carried out at a salt concentration of 0.25 M-5.0 M.

In one embodiment is provided a solid object having a surface comprising a layered coating of cationic and anionic polymer, wherein the outer coating layer is a layer comprising cationic polymer to which is covalently bound an anticoagulant entity; the anionic polymer is a polymer comprising $—SO_3^-$ groups and wherein the anionic polymer is characterized by having (a) a total molecular weight of 650 kDa-10,000 kDa; and (b) a sulfur content between 10% and 25% by weight of the anionic polymer.

In one embodiment is provided a process for the manufacture of a solid object having a surface comprising a layered coating of cationic and anionic polymer wherein the outer coating layer is a layer comprising cationic polymer, comprising the steps of:
i) treating a surface of the solid object with a cationic polymer;
ii) treating the surface with an anionic polymer;
iii) optionally repeating steps i) and ii) one or more times; and
iv) treating the surface with a cationic polymer;
wherein,
the anionic polymer is a polymer comprising $—SO_3^-$ groups,
the anionic polymer is characterized by having (a) a total molecular weight of 650 kDa-10,000 kDa; and (b) a sulfur content between 10% and 25% by weight of the anionic polymer;
and wherein,
step ii) is carried out at a salt concentration of 0.25 M-5.0 M.

In one embodiment is provided a process for the manufacture of a solid object having a surface comprising a layered coating of cationic and anionic polymer wherein the outer coating layer is a layer comprising cationic polymer, comprising the steps of:
i) treating a surface of the solid object with a cationic polymer;
ii) treating the surface with an anionic polymer;
iii) optionally repeating steps i) and ii) one or more times; and
iv) treating the surface with a cationic polymer;
wherein,
the anionic polymer is characterized by having a total molecular weight of 650 kDa-10,000 kDa;
the anionic polymer is dextran sulfate;
and wherein,
step ii) is carried out at a salt concentration of 0.25 M-5.0 M.

In one embodiment is provided a solid object having a surface comprising a layered coating of cationic and anionic polymer, wherein the outer coating layer is a layer comprising cationic polymer; the anionic polymer is a polymer comprising —$SO_3^-$ groups and wherein the anionic polymer is characterized by having (a) a total molecular weight of 650 kDa-10,000 kDa; and (b) a sulfur content between 10% and 25% by weight of the anionic polymer.

In one embodiment is provided a process for the manufacture of a solid object having a surface comprising a layered coating of cationic and anionic polymer wherein the outer coating layer is a layer comprising anionic polymer, comprising the steps of:
 i) treating a surface of the solid object with a cationic polymer;
 ii) treating the surface with an anionic polymer;
 iii) optionally repeating steps i) and ii) one or more times;
wherein,
 the anionic polymer is a polymer comprising —$SO_3^-$ groups,
 the anionic polymer is characterized by having (a) a total molecular weight of 650 kDa-10,000 kDa; and (b) a sulfur content between 10% and 25% by weight of the anionic polymer;
and wherein,
 step ii) is carried out at a salt concentration of 0.25 M-5.0 M.

In one embodiment is provided a process for the manufacture of a solid object having a surface comprising a layered coating of cationic and anionic polymer wherein the outer coating layer is a layer comprising anionic polymer, comprising the steps of:
 i) treating a surface of the solid object with a cationic polymer;
 ii) treating the surface with an anionic polymer;
 iii) optionally repeating steps i) and ii) one or more times;
wherein,
 the anionic polymer is characterized by having a total molecular weight of 650 kDa-10,000 kDa;
 the anionic polymer is dextran sulfate;
and wherein,
 step ii) is carried out at a salt concentration of 0.25 M-5.0 M.

In one embodiment is provided a solid object having a surface comprising a layered coating of cationic and anionic polymer, wherein the outer coating layer is a layer comprising anionic polymer; the anionic polymer is a polymer comprising —$SO_3^-$ groups and wherein the anionic polymer is characterized by having (a) a total molecular weight of 650 kDa-10,000 kDa; and (b) a sulfur content between 10% and 25% by weight of the anionic polymer.

Clauses of the Invention

Additional Clauses of the Invention:
1. A process for the manufacture of a solid object having a surface comprising a layered coating of cationic and anionic polymer wherein the outer coating layer comprises an anticoagulant entity, comprising the steps of:
 i) treating a surface of the solid object with a cationic polymer;
 ii) treating the surface with an anionic polymer;
 iii) optionally repeating steps i) and ii) one or more times;
 iv) treating the surface with a cationic polymer; and
 v) treating the outermost layer of cationic polymer with an anticoagulant entity, thereby to covalently attach the anticoagulant entity to the outermost layer of cationic polymer;
wherein,
 the anionic polymer is characterized by having (a) a total molecular weight of 650 kDa-10,000 kDa; and (b) a solution charge density of >4 µeq/g;
and wherein,
 step ii) is carried out at a salt concentration of 0.25 M-5.0 M.

2. A process for the manufacture of a solid object according to clause 1, wherein the anionic polymer is dextran sulfate.

3. A process for the manufacture of a solid object according to clause 1 or clause 2, wherein the anionic polymer is characterized by having a total molecular weight of 750 kDa-10,000 kDa, such as 1,000 kDa-10,000 kDa.

4. A process for the manufacture of a solid object according to any one of clauses 1 to 3, wherein the anionic polymer is characterized by having a solution charge density of between >4 µeq/g and 7 µeq/g, such as between >5 µeq/g and 7 µeq/g.

5. A process for the manufacture of a solid object according to any one of clauses 1 to 4, wherein step ii) is carried out at a salt concentration of 0.25 M-4.0 M, such as 0.25 M-3.0 M.

6. A process for the manufacture of a solid object according to any one of clauses 1 to 5, wherein the salt is selected from the group consisting of sodium chloride, sodium sulfate, sodium hydrogen phosphate and sodium phosphate, and in particular is sodium chloride.

7. A process for the manufacture of a solid object according to any one of clauses 1 to 6, wherein the cationic polymer of step i) is a polyamine, which is optionally cross-linked; and/or
 wherein the cationic polymer of step iv) is a polyamine, which is optionally cross-linked.

8. A process for the manufacture of a solid object according to any one of clauses 1 to 7, wherein the anticoagulant entity is a heparin moiety e.g. an end-point attached heparin moiety which is connected through its reducing end.

9. A process for the manufacture of a solid object according to any one of clauses 1 to 8, wherein the solid object is a thromboresistant medical device.

10. A solid object having a surface comprising a layered coating of cationic and anionic polymer, wherein the outer coating layer is a layer comprising cationic polymer to which is covalently bound an anticoagulant entity; and wherein the anionic polymer is characterized by having (a) a total molecular weight of 650 kDa-10,000 kDa; and (b) a solution charge density of >4 µeq/g.

11. A solid object according to clause 10, wherein the anionic polymer is characterized by having a total molecular weight of 650 kDa-1,000 kDa, or 1,000 kDa-4,500 kDa or 4,500 kDa-7,000 kDa or 7,000 kDa-10,000 kDa.

12. A solid object according to any one of clauses 10 or 11, wherein the anionic polymer is applied to the surface at a salt concentration of 0.25 M-5.0 M, such as 0.25 M-4.0 M or 0.25 M-3.0 M.

13. A process for the manufacture of a solid object having a surface comprising a layered coating of cationic and anionic polymer wherein the outer coating layer is a layer comprising cationic polymer, comprising the steps of:

i) treating a surface of the solid object with a cationic polymer;
ii) treating the surface with an anionic polymer;
iii) optionally repeating steps i) and ii) one or more times; and
iv) treating the surface with a cationic polymer;
wherein,
the anionic polymer is characterized by having (a) a total molecular weight of 650 kDa-10,000 kDa; and (b) a solution charge density of >4 µeq/g;
and wherein,
step ii) is carried out at a salt concentration of 0.25 M-5.0 M.

14. A solid object having a surface comprising a layered coating of cationic and anionic polymer, wherein the outer coating layer is a layer comprising cationic polymer; and wherein the anionic polymer is characterized by having (a) a total molecular weight of 650 kDa-10,000 kDa; and (b) a solution charge density of >4 µeq/g.

15. A process for the manufacture of a solid object having a surface comprising a layered coating of cationic and anionic polymer wherein the outer coating layer is a layer comprising anionic polymer, comprising the steps of:
i) treating a surface of the solid object with a cationic polymer;
ii) treating the surface with an anionic polymer;
iii) optionally repeating steps i) and ii) one or more times; wherein,
the anionic polymer is characterized by having (a) a total molecular weight of 650 kDa 10,000 kDa; and (b) a solution charge density of >4 µeq/g;
and wherein,
step ii) is carried out at a salt concentration of 0.25 M-5.0 M.

Advantages

Solid objects coated according to the process of the invention, at least in some embodiments, are expected to have one or more of the following merits or advantages:
A coating of the anticoagulant entity having uniform distribution and being comparatively smooth can be obtained e.g. as determined using Evaluation Method C (toluidine blue staining test) or Evaluation Method I (SEM);
A uniform coating may be obtained which will mask the intrinsic properties of the solid object, for example to improve the thromboresistant properties of a device irrespective of the material of its manufacture;
A coating with good anticoagulant entity activity such as heparin activity can be obtained e.g. as determined using Evaluation Method B or M;
A thromboresistant coating which does not leach anticoagulant entity e.g. heparin, due to its covalent attachment and therefore has a long lifetime may be obtained;
A coating whose properties are preserved upon sterilization (e.g. with EO) may be obtained;
A self-healing coating may be obtained due to the possibility of reversible forming of ionic interactions between the layers;
A coating with good biocompatibility can be obtained e.g. as determined by using Evaluation Method N;
A coating which may reduce the need for systemic administration of anticoagulant e.g. heparin, and reduce the likelihood of contact activation e.g. as determined using Evaluation Method E (platelets) and/or Evaluation Method F (blood loop) may be obtained;
A solid object having a combination of anti-inflammatory properties as determined by using Evaluation Method N and thromboresistance can be obtained which may be beneficial in certain applications e.g. cardiovascular applications;
An analytical or separation device with good binding capacity to biomolecules may be obtained; and
An analytical or separation device with long heparin activity life time may be obtained.

The invention embraces all combinations of indicated groups and embodiments of groups recited above.

Abbreviations

Ac acetyl
ABS acrylonitrile butadiene styrene
ATIII antithrom bin III
CNS central nervous system
CPB cardiopulmonary bypass
CVC central venous catheter
CVD chemical vapour deposition
Da dalton
DI deionized
EDC 1-ethyl-3-(3-dimethylaminopropyl)-carbodiimide
EO ethylene oxide
EPDM ethylene propylene diene monomer (M-class)
ePTFE expanded polytetrafluoroethylene
FEP fluorinated ethylene-propylene
GPC gel permeation chromatography
HCII heparin cofactor II
HIT heparin induced thrombocytopenia
IEP isoelectric point
M molar concentration
MBTH 3-methyl-2-benzothiazolinone hydrazone hydrochloride
PAVE perfluoroalkylvinyl ether
PES-Na sodium polyethylene sulfate
PTA percutaneous transluminal angioplasty
PIC peripherally inserted central catheter
PMVE perfluoromethyl vinyl ether
PTFE polytetrafluoroethylene
PUR polyurethane
PVC polyvinyl chloride
RGD arginylglycylaspartic acid
SEM scanning electron microscopy/microscope
SPDP N-succinimidyl 3-(2-pyridyldithio)propionate
TFE tetrafluoroethylene
TMAH tetramethyl ammonium hydroxide
TM B 3,3',5,5'-tetramethylbenzidine
VA ventriculoatrial
VP ventriculoperitoneal
XPS X-ray photoelectron spectroscopy

EXAMPLES

General Procedures

Chemicals

Isopropanol, sodium dihydrogen phosphate dihydrate, sodium sulfate and sodium chloride are available from Sigma Aldrich and VWR Chemicals and may be used as received. Heparin of pharmacopea quality was treated with nitrous acid, essentially as described in EP0086186A1 and used in the Examples. Polyamines are available from vendors as described in U.S. Pat. No. 9,101,69662. Dextran sulfates were purchased from various vendors as indicated in Table 1 of Example 1. Deionized (DI) water was used in the Examples below.

Materials

PVC tubing was purchased from Flex Tubing Products. PUR tubing was purchased from NewAge Industries. Stainless steel coupons were purchased from Helab Mekano A B.

Evaluation Methods

The parameter being evaluated by each method is given in parentheses.

Evaluation Method A: Heparin Concentration Test (Quantitative Heparin Attachment)

Quantification of surface immobilized heparin can be performed by complete degradation of heparin followed by colorimetric determination of the reaction products released into solution. Degradation is achieved by reacting the heparin surface with an excess of sodium nitrite under acidic conditions. The degradation products, mainly disaccharides, are quantified colorimetrically in a reaction with MBTH (3-methyl-2-benzothiazolinone hydrazone hydrochloride), essentially as described in Smith R. L. and Gilkerson E (1979), Anal Biochem 98, 478-480, which is incorporated herein by reference in its entirety.

Evaluation Method B: Heparin Activity Test (Quantitative Heparin Function Using ATIII)

For solid objects coated according to the process of the invention comprising a heparin coating, the heparin activity of the device can be measured by measuring the ability, or capacity, of the heparin to bind antithrombin III (ATIII) as described by Pasche, et al. in "A binding of antithrombin to immobilized heparin under varying flow conditions" (Artif. Organs 1991; 15:281-491, incorporated herein by reference in its entirety) and Larsen M. L, et al. in "Assay of plasma heparin using thrombin and the chromogenic substrate H-D-Phe-Pip-Arg-pNA" (S-2238) (Thromb. Res. 1978; 13:285-288, incorporated herein by reference in its entirety), and can be used to evaluate a solid object's thromboresistant properties. Washed samples are incubated with an excess of antithrombin in solution to saturate all available antithrombin-binding sites of the heparin surface. Non-specifically adsorbed antithrombin is rinsed away using a salt solution.

Subsequently, antithrom bin specifically bound to the surface bound heparin is released by incubating with a solution of heparin at high concentration. Finally, the antithrom bin released from the heparin surface is measured in a thrombin inhibition assay, based on a chromogenic thrombin substrate. The results are expressed as picomoles antithrombin III (ATIII) bound per apparent square centimeter of device (pmol ATIII/$cm^2$ solid object surface). The apparent solid object surface area does not take into account multiple covered surfaces nor porosity considerations of a solid object composed of a porous material. If the surface of the solid object is porous, the effect of porosity on surface area is not considered for these calculations. For example, the apparent surface area of a cylindrical tubular ePTFE vascular graft (which is made of a porous material) with heparin immobilized on substrate material comprising the inner surface of the tubular graft is calculated as it is for any cylindrical geometry as $2\pi rL$: where r is the graft inner radius; L is the axial length; and $\pi$ is the number pi. This method can be used to measure the activity of any anticoagulant entity with ATIII binding activity.

Evaluation Method C: Toluidine Blue Staining Test (Heparin Distribution)

Heparin distribution is evaluated using toluidine blue staining solution. The solution is prepared by dissolving 200 mg of toluidine blue in 1 L of water. The samples are subjected to the staining solution for 2 minutes prior to extensive water rinse. A blue/violet staining indicates that negatively charged heparin molecules are homogenously distributed in the outer coating layer.

Evaluation Method D: Zeta Potential Measurement (Indicator of Surface Charge)

Zeta potential, as an indicator of surface charge, of the coating is determined on a SurPASS instrument. The measurement is conducted by circulating an electrolyte over the surface, which is by standard a 1 mM solution of a simple electrolyte such as KCl or NaCl. The resulting streaming potential is measured and used to determine the zeta potential. The zeta potential of coating is determined in the pH range 3 to 9 via addition of acid or base to the solution respectively. The zeta potential is calculated using Eq 1 below, as described in T. Luxbacher, The ZETA guide, Principles of the streaming potential technique, first edition, published by Anton Paar GMBH, ISBN 978-3-200-03553-9 (incorporated herein by reference in its entirety).

$$\zeta = \frac{dU}{dp} \times \frac{\eta}{\varepsilon \times \varepsilon_0} \times K_B \quad \text{(Eq 1)}$$

dU/dP=slope of streaming potential vs differential pressure, $K_B$=electrolyte conductivity n=electrolyte viscosity $\varepsilon$=dielectric coefficient of electrolyte $\varepsilon_0$=vacuum permittivity.

Evaluation Method E: Blood Loop Evaluation Test (Measurement of Platelet Loss)

Blood contact evaluation can be performed on a coated object to evaluate its thromboresistant properties. A procedure which may be used when the solid object is a tubular device such as a piece of PVC tubing is as follows. Firstly, the luminal side of the coated tubing is washed with 0.15 M saline solution for 15 hours at a flow of 1 mL/min to ensure complete wetting and removal of any loosely bound anticoagulant entity, such that a stable surface remains. The washed tubing is then incubated in a Chandler loop model performed essentially according to Andersson et al. (Andersson, J.; Sanchez, J.; Ekdahl, K. N.; Elgue, G.; Nilsson, B.; Larsson, R. J Biomed Mater Res A 2003, 67(2), 458-466, incorporated herein by reference in its entirety) at 20 rpm. The platelets from fresh blood and from the blood collected from the loops are counted in a cell counter to measure the loss of platelets. A great loss of platelets indicates poor thromboresistant performance of the surface. Conversely a minimal loss of platelets indicates a thromboresistant surface.

Evaluation Method F: Blood Loop Evaluation Test (for Measurement of F1+2)

The determination of F1+2 (prothrom bin fragment) is used as an activation marker for coagulation (i.e. as an indirect measurement of thrombin). F1+2 is directly proportional to the formation of thrombin and interpreted as an indirect measurement of thrombin generation, and can be used to evaluate a solid object's thromboresistant properties. Quantitative determination of F1+2 in plasma is performed with an enzymatic immunoanalysis, by using a standard ELISA kit (Enzyme-Linked Immuno Sorbent Assay) (Enzygnost F1+2 ELISA, OPBDG03, Siemens). The F1+2 antigen in the sample couples to the antibodies entrapped on the coated surface of 96-well microtiter plate and subsequently detected by a peroxidase conjugated anti-F1+2 antibody. The amount of coupled peroxidase is measured by addition of a specific substrate, 3,3',5,5'-tetramethylbenzidine (TMB). The enzymatic conversion of the substrate to chromogen is stopped by addition of diluted sulfuric acid. Absorbance at 450 nm in the wells is proportional to the concentration of F1+2 in the sample. The concentration of the samples is determined by comparison to a standard curve with known concentrations of F1+2.

Evaluation Method G: Molecular Weight of Anionic Polymers Such as Dextran Sulfate in Solution Determination of the molecular weight of a dextran sulfate sample is performed on a gel permeation chromatography (GPC) instrument. The dextran sulfate samples are dissolved in a water-based elution media and analyzed on a GPC instrument suitable for the molecular weight range 1,000 Da-100,000 Da (superose column) or 100,000 Da-2,000,000 Da (sephacryl column). A dextran sulfate standard of an appropriate molecular weight is used to verify the accuracy of the calibration curve. Polymers such as dextran sulfate are disperse molecules i.e. have a distribution of molecular weights, which can be described with different molecular weight averages. The commonly reported value is the weight average molecular weight (Mw). See Odian G., Principles of Polymerization, Third edition, Section 1.4 Molecular weight, p. 24 (incorporated herein by reference in its entirety) which explains the theory on determination of molecular weights of polymers using GPC techniques. The molecular weight of anionic polymers other than dextran sulfate can also be determined using this method.

Evaluation Method H: Solution Charge Density of Anionic Polymers Such as Dextran Sulfate in Solution Quantitative determination of charge density is performed on a MUtek Particle Charge Detector via titration of polyelectrolyte solutions (0.001 M) (polydiallyldimethylammonium chloride (Poly-Dadmac) and sodium polyethylene sulfate (PES-Na)). Samples are dissolved in water (maximum viscosity allowed 6000 m Pas) to a concentration of 0.06 g/L. The pH is adjusted to 3 for all sample solutions. 10 mL per sample solution is added each measurement followed by titration of appropriate polyelectrolyte solution at an interval of 1 unit per 3 seconds. See S. Farris et al., Charge Density Quantification of Polyelectrolyte Polysaccharides by Conductometric Titration: An Analytical Chemistry Experiment, J. Chem. Educ., 2012, 89 (1), pp 121-124 (incorporated herein by reference in its entirety). The solution charge density of anionic polymers other than dextran sulfate can also be determined using this method.

Evaluation Method I: Scanning Electron Microscopy with Energy Dispersive X-Ray Spectroscopy (Coating Coverage and Uniformity)

TM3000 is a table-scanning electron microscope (SEM) manufactured by Hitachi that is used to obtain information about e.g. a sample thickness, topography (surface structure) and surface coverage. A higher magnification can be achieved with table SEM compared to traditional light microscopes as it is electrons used to create the image. The TM3000 is also equipped with Quantax70. This is an Energy Dispersive X-ray Spectrometer (EDS) used to determine the chemical composition of the sample. In addition, there is a rotation/tilt table as accessory to facilitate analysis of different parts of the sample. The sample is mounted on a holder with carbon tape (also acts as grounding) and then placed in the test chamber. The chamber is evacuated to a lower pressure before evaluation of the sample can commence. SEM technology is based on the scanning of an electron beam across the sample, some of the electrons being reflected backscattered electrons, while others execute secondary electrons. A detector is used to measure the current generated by the reflected backscattered electrons. The current is imaged on a display where each pixel corresponds to the position of the sample. A bright pixel is obtained if many electrons are reflected (high electron density) and a darker pixel is obtained if few electrons (low electron density) are reflected.

Evaluation Method J: X-Ray Photoelectron Spectroscopy with Depth Profiling (XPS) (Coating Thickness)

X-ray Photoelectron Spectroscopy (XPS or ESCA) is the most widely used surface characterization technique providing non-destructive chemical analysis of solid materials. Samples are irradiated with mono-energetic X-rays causing photoelectrons to be emitted from the top 1 nm-10 nm of the sample surface. An electron energy analyzer determines the binding energy of the photoelectrons. Qualitative and quantitative analysis of all elements except hydrogen and helium is possible, at detection limits of ~0.1-0.2 atomic percent. Analysis spot sizes range from 10 μm to 1.4 mm. It is also possible to generate surface images of features using elemental and chemical state mapping. Depth profiling is possible using angle-dependent measurements to obtain non-destructive analyses within the top 10 nm of a surface, or throughout the coating depth using destructive analysis such as ion etching.

Evaluation Method K: Increased Temperature and Humidity Test (General Model for Sterilization Stability) The solid object coated according to the process of the invention is placed in a breathable polyethylene pouch (e.g. a Tyvek pouch). The pouch is placed in a climate chamber (e.g. Climacell) at 40° C. and 50% relative humidity for 1 week followed by 2 hours drying in a vacuum chamber. After performing this general model for sterilization stability, the thromboresistant properties/activation of the coated object is assessed e.g. using Evaluation Method E or F.

Evaluation Method L: Stability to Ethylene Oxide

The solid object coated according to the process of the invention is placed in a breathable polyethylene pouch (e.g. a Tyvek pouch) and subjected to at least 12 hours preconditioning at 50° C. and 60% relative humidity followed by 2 hours exposure of ethylene oxide at a pressure of 366 mBar and 50° C. The chamber is then degassed at 50° C. for at least 10 hours. Sterilization by ethylene oxide may be performed at Synergy Health Ireland Ltd. After sterilization, the thromboresistant properties/activation of the coated object is assessed e.g. using Evaluation Method E or F.

Evaluation Method M: Heparin Activity Test (Quantitative Heparin Function Using HCII)

For solid objects coated according to the process of the invention comprising a heparin coating, the heparin activity of the device can be measured by measuring the ability, or capacity, of the heparin to bind heparin cofactor II (HCII) as described in WO2009/064372A2 (Gore Enterprise Holdings, Inc.; incorporated herein by reference in its entirety) by measuring the ability, or capacity, of the heparin to bind a known quantity of heparin cofactor II (HCII), using an assay as described by Larsen M. L., et al., in "Assay of plasma heparin using thrombin and the chromogenic substrate H-D-Phe-Pip-Arg-pNA (S-2238)." Thromb Res 13:285-288 (1978) and Pasche B., et al., in "A binding of antithrombin to immobilized heparin under varying flow conditions." Artif. Organs 1991; 15:281-491), and can be used to evaluate a solid object's thromboresistant properties. The results are expressed as picomoles heparin cofactor II (HCII) bound per apparent square centimetre of solid object surface (pmol HCII/cm² solid object surface). The apparent solid object surface area does not take into account multiple covered surfaces nor porosity considerations of a device composed of a porous material. If the surface of the device is porous, the effect of porosity on surface area is not considered for these calculations. For example, the apparent surface area of a cylindrical tubular ePTFE vascular graft (which is made of a porous material) with heparin immobilized on substrate material comprising the inner surface of the tubular graft is calculated as it is for any cylindrical geometry as $2\pi rL$: where r is the graft inner radius; L is the axial length; and $\pi$ is the number pi. This method can be used to measure the activity of any anticoagulant entity with HCII binding activity.

Evaluation Method N—Surface Biocompatibility

The biocompatibility of a surface of a solid object coated according to a process of the invention can be assessed as described in Lappegard, K. T 2008, J. Biomed. Mater. Res. Vol 87, 129-135 (incorporated herein by reference in its entirety). A procedure which may be used to evaluate the inflammatory response is as follows. Firstly, the coated solid object is washed with 0.15 M saline solution for 15 min. The wetted coated solid object is placed in heparinized PVC tubing containing whole blood and left to rotate in a circulating loop at 20 rpm (see Ekdahl K. N., Advances in Experimental Medicine and Biology, 2013, 735, 257-270 (incorporated herein by reference in its entirety) for a representative procedure). After incubation, the blood is centrifuged for 15 min, 3220 g at 4° C. The plasma is frozen in aliquots at −70° C. for later analysis of cytokines. Plasma samples are analyzed using multiplex cytokine assay (Bio-Plex Human Cytokine 27-Plex Panel, Bio-Rad Laboratories, Hercules, CA) according to the method described by Lappegard et al. (above).

The negative control is an empty loop of heparinized PVC without any device. This represents a non-inflammatory control for which the incubated blood should demonstrate no or minimal amount of inflammatory markers. The positive control is an empty loop of non-heparinized PVC without any device. This represents an inflammatory control for which a greater amount of inflammatory markers should be observed. The controls are included for ensuring the quality of the experiment and the blood.

Evaluation Method O—Quartz Crystal Microbalance with Dissipation (Coating Thickness)

Q-sense E4 is a crystal microbalance with dissipation (QCM-D) monitoring instrument. QCM-D is a technique for measurement of both mass and structural properties of molecular layers and may be seen as an ultrasensitive weighing deceive.

A QCM sensor consists of a thin quartz disc where AT-cut crystals are the most commonly used. The quartz disc is placed between two electrodes and by applying a voltage to the quartz crystal it can be made to oscillate at its resonance frequency. Changes in mass on the quartz surface induces a change in frequency of the oscillating crystal related through the Sauerbrey relationship (see Rodahl, M., et al., Quartz crystal microbalance setup for frequency and Q factor measurements in gaseous and liquid environments. Review of scientific environments, 1995. 66(7): p.3924-3930. (incorporated herein by reference in its entirety). Coating thickness of solid objects coated according to the process of the invention are reported as dry coating thickness.

Evaluation Method P—Molecular Weight Determination of the Heparin Fragment Fractions The molecular weight of Heparin fragment fractions are determined by analytical gel permeation chromatography (GPC) on a system consisting of two Superdex columns in series (S-75 and S-200) essentially according to USP<209>Low Molecular Weight Heparin Molecular Weight Determinations. Peak positions are identified based on the elution profile of the 2nd International Standard for Low Molecular Weight Heparin for Molecular Weight Calibration (NIBSC, UK), where the least retarded peak of the standard is a disaccharide.

Evaluation Method Q—Heparin Fragment Concentration Determination

The quantities of isolated heparin fragment in solution are estimated by analyzing the uronic acid content by the carbazole assay (Bitter, T.; Muir, H. M., Anal. Biochem., 1962, (4), 330-334), related to a heparin standard curve.

Example 1: Processes for Coating a Solid Object (Layered Coating of Cationic and Anionic Polymer, with Outer Coating Layer of Anticoagulant Entity)

General Coating Process—Tubing

The luminal surface of a section of tubing (e.g. PVC or PUR tubing) is coated with a layer-by-layer coating of cationic polymer and anionic polymer using essentially the method described by Larm et al. in EP0086186A1, EP0495820B1 and EP0086187A1 (all incorporated herein by reference in their entirety).

Specifically, the luminal surface of the tubing is firstly cleaned with isopropanol and an oxidizing agent. The coating bilayers are built-up by alternating adsorption of a cationic polymer (polyamine, 0.05 g/L in water) and an anionic polymer (dextran sulfate, 0.1 g/L in water). The polyamine is crosslinked with a difunctional aldehyde (crotonaldehyde). The dextran sulfate raw material is varied as specified in each of the Examples below, and applied in the presence of various sodium salts at varied concentrations, again as specified in each Example below. Every pair of polyamine and sulfated polysaccharide is called one bilayer i.e. a bilayer is defined as one layer of cationic and anionic polymer and the same conditions are used for building up of each bilayer. The luminal surface of the tubing is coated with three bilayers (see FIG. 1 for a solid object coated with a single bilayer). A final, outermost layer of polyamine is then adsorbed.

Heparin is then immobilized to the outermost layer of polyamine via reductive amination, essentially as described by Larm et al. in EP0086186A1 and EP0495820B1 (both incorporated herein by reference in their entirety).

General Coating Process—Steel Coupons

Any solid object can be coated using the general coating process described above for tubing. In the Examples below where a steel coupon was utilized, the entire surface of the coupon was coated.

Dextran Sulfates Used in Examples 1.1-1.56

The evaluated dextran sulfates were purchased from different vendors as presented in Table 1.

TABLE 1

Dextran sulfates evaluated in the Examples

| Dextran sulfate No. | Vendor | Mw* [kDa] | Solution charge density** [µeq/g] (pH 3) |
|---|---|---|---|
| 1 (Reference example dextran sulfate) | Sigma Aldrich | 50 | 6.1 |
| 2 (Reference example dextran sulfate) | Tdb Consultancy | 100 | 5.4 |
| 3 (Reference example dextran sulfate) | Tdb Consultancy | 600 | 3.0 |
| 4 | Tdb Consultancy | 800 | 6.3 |
| 5 | pK Chemicals A/S | 4000 | 6.2 |
| 6 | Alfa Aesar | 5000 | 5.3 |
| 7 | Sigma Aldrich | 8000 | 6.4 |

*Weight average molecular weight (Mw) determined according to Evaluation Method G
**Solution charge density determined according to Evaluation Method H Example 1.1: Preparation of Coating on PVC Tubing Using Dextran Sulfate 1 and NaCl Concentration of 0.25 M PVC tubing (I.D. 3 mm) was coated according to the general procedure described above. Dextran sulfate 1, see Table 1, was applied at NaCl concentration of 0.25 M.

Example 1.2: Preparation of Coating on PVC Tubing Using Dextran Sulfate 1 and NaCl Concentration of 1.7 M PVC tubing (I.D. 3 mm) was coated according to the general procedure described above. Dextran sulfate 1, see Table 1, was applied at NaCl concentration of 1.7 M.

Example 1.3: Preparation of Coating on PVC Tubing Using Dextran Sulfate 2 and NaCl Concentration of 0.25 M PVC tubing (I.D. 3 mm) was coated according to the general procedure described above. Dextran sulfate 2, see Table 1, was applied at NaCl concentration of 0.25 M.

Example 1.4: Preparation of Coating on PVC Tubing Using Dextran Sulfate 3 and NaCl Concentration of 0.05 M PVC tubing (I.D. 3 mm) was coated according to the general procedure described above. Dextran sulfate 3, see Table 1, was applied at NaCl concentration of 0.05 M.

Example 1.5: Preparation of Coating on PVC Tubing Using Dextran Sulfate 3 and NaCl Concentration of 0.1 M PVC tubing (I.D. 3 mm) was coated according to the general procedure described above. Dextran sulfate 3, see Table 1, was applied at NaCl concentration of 0.1 M.

Example 1.6: Preparation of Coating on PVC Tubing Using Dextran Sulfate 3 and NaCl Concentration of 0.25 M PVC tubing (I.D. 3 mm) was coated according to the general procedure described above. Dextran sulfate 3, see Table 1, was applied at NaCl concentration of 0.25 M.

Example 1.7: Preparation of Coating on PVC Tubing Using Dextran Sulfate 3 and NaCl Concentration of 1.0 M PVC tubing (I.D. 3 mm) was coated according to the general procedure described above. Dextran sulfate 3, see Table 1, was applied at NaCl concentration of 1.0 M.

Example 1.8: Preparation of Coating on PVC Tubing Using Dextran Sulfate 3 and NaCl Concentration of 1.7 M PVC tubing (I.D. 3 mm) was coated according to the general procedure described above. Dextran sulfate 3, see Table 1, was applied at NaCl concentration of 1.7 M.

Example 1.9: Preparation of Coating on PVC Tubing Using Dextran Sulfate 3 and NaCl Concentration of 2.6 M PVC tubing (I.D. 3 mm) was coated according to the general procedure described above. Dextran sulfate 3, see Table 1, was applied at NaCl concentration of 2.6 M.

Example 1.10: Preparation of Coating on PVC Tubing Using Dextran Sulfate 3 and NaCl Concentration of 3.0 M PVC tubing (I.D. 3 mm) was coated according to the general procedure described above. Dextran sulfate 3, see Table 1, was applied at NaCl concentration of 3.0 M.

Example 1.11: Preparation of Coating on PVC Tubing Using Dextran Sulfate 4 and NaCl Concentration of 0.05 M PVC tubing (I.D. 3 mm) was coated according to the general procedure described above. Dextran sulfate 4, see Table 1, was applied at NaCl concentration of 0.05 M.

Example 1.12: Preparation of Coating on PVC Tubing Using Dextran Sulfate 4 and NaCl Concentration of 0.1 M PVC tubing (I.D. 3 mm) was coated according to the general procedure described above. Dextran sulfate 4, see Table 1, was applied at NaCl concentration of 0.1 M.

Example 1.13: Preparation of Coating on PVC Tubing Using Dextran Sulfate 4 and NaCl Concentration of 0.25 M PVC tubing (I.D. 3 mm) was coated according to the general procedure described above. Dextran sulfate 4, see Table 1, was applied at NaCl concentration of 0.25 M.

Example 1.14: Preparation of Coating on PVC Tubing Using Dextran Sulfate 4 and NaCl Concentration of 1.0 M PVC tubing (I.D. 3 mm) was coated according to the general procedure described above. Dextran sulfate 4, see Table 1, was applied at NaCl concentration of 1.0 M.

Example 1.15: Preparation of Coating on PVC Tubing Using Dextran Sulfate 4 and NaCl Concentration of 1.7 M PVC Tubing (I.D. 3 mm) was Coated According to the General Procedure Described Above. Dextran Sulfate 4, See Table 1, was Applied at NaCl Concentration of 1.7 M.

Example 1.16: Preparation of Coating on PVC Tubing Using Dextran Sulfate 4 and NaCl Concentration of 3.0 M PVC tubing (I.D. 3 mm) was coated according to the general procedure described above. Dextran sulfate 4, see Table 1, was applied at NaCl concentration of 3.0 M.

Example 1.17: Preparation of Coating on PVC Tubing Using Dextran Sulfate 5 and NaCl Concentration of 0.05 M PVC tubing was coated according to the general procedure described above. Dextran sulfate 5, see Table 1, was applied at NaCl concentration of 0.05 M.

Example 1.18: Preparation of Coating on PVC Tubing Using Dextran Sulfate 5 and NaCl Concentration of 0.25 M PVC tubing (I.D. 3 mm) was coated according to the general procedure described above. Dextran sulfate 5, see Table 1, was applied at NaCl concentration of 0.25 M.

Example 1.19: Preparation of Coating on PVC Tubing Using Dextran Sulfate 5 and NaCl Concentration of 0.5 M PVC tubing (I.D. 3 mm) was coated according to the general procedure described above. Dextran sulfate 5, see Table 1, was applied at NaCl concentration of 0.5 M.

Example 1.20: Preparation of Coating on PVC Tubing Using Dextran Sulfate 5 and NaCl Concentration of 0.85 M PVC tubing (I.D. 3 mm) was coated according to the general procedure described above. Dextran sulfate 5, see Table 1, was applied at NaCl concentration of 0.85 M.

Example 1.21: Preparation of Coating on PVC Tubing Using Dextran Sulfate 5 and NaCl Concentration of 1.0 M PVC tubing (I.D. 3 mm) was coated according to the general procedure described above. Dextran sulfate 5, see Table 1, was applied at NaCl concentration of 1.0 M.

Example 1.22: Preparation of Coating on PVC Tubing Using Dextran Sulfate 5 and NaCl Concentration of 1.7 M PVC tubing (I.D. 3 mm) was coated according to the general procedure described above. Dextran sulfate 5, see Table 1, was applied at NaCl concentration of 1.7 M.

Example 1.23: Preparation of Coating on PVC Tubing Using Dextran Sulfate 5 and NaCl Concentration of 3.0 M PVC tubing (I.D. 3 mm) was coated according to the general procedure described above. Dextran sulfate 5, see Table 1, was applied at NaCl concentration of 3.0 M.

Example 1.24: Preparation of Coating on PVC Tubing Using Dextran Sulfate 6 and NaCl Concentration of 0.05 M PVC tubing (I.D. 3 mm) was coated according to the general procedure described above. Dextran sulfate 6, see Table 1, was applied at NaCl concentration of 0.05 M

Example 1.25: Preparation of Coating on PVC Tubing Using Dextran Sulfate 6 and NaCl Concentration of 0.25 M PVC tubing (I.D. 3 mm) was coated according to the general procedure described above. Dextran sulfate 6, see Table 1, was applied at NaCl concentration of 0.25 M.

Example 1.26: Preparation of Coating on PVC Tubing Using Dextran Sulfate 6 and NaCl Concentration of 0.5 M PVC tubing (I.D. 3 mm) was coated according to the general procedure described above. Dextran sulfate 6, see Table 1, was applied at NaCl concentration of 0.5 M.

Example 1.27: Preparation of Coating on PVC Tubing Using Dextran Sulfate 6 and NaCl Concentration of 1.7 M PVC tubing (I.D. 3 mm) was coated according to the general procedure described above. Dextran sulfate 6, see Table 1, was applied at NaCl concentration of 1.7 M.

Example 1.28: Preparation of Coating on PVC Tubing Using Dextran Sulfate 6 and NaCl Concentration of 3.0 M PVC tubing (I.D. 3 mm) was coated according to the general procedure described above. Dextran sulfate 6, see Table 1, was applied at NaCl concentration of 3.0 M.

Example 1.29: Preparation of Coating on PVC Tubing Using Dextran Sulfate 7 and NaCl Concentration of 0.05 M PVC tubing (I.D. 3 mm) was coated according to the general procedure described above. Dextran sulfate 7, see Table 1, was applied at NaCl concentration of 0.05 M.

Example 1.30: Preparation of Coating on PVC Tubing Using Dextran Sulfate 7 and NaCl Concentration of 0.1 M PVC tubing (I.D. 3 mm) was coated according to the general procedure described above. Dextran sulfate 7, see Table 1, was applied at NaCl concentration of 0.1 M.

Example 1.31: Preparation of Coating on PVC Tubing Using Dextran Sulfate 7 and NaCl Concentration of 0.25 M PVC tubing (I.D. 3 mm) was coated according to the general procedure described above. Dextran sulfate 7, see Table 1, was applied at NaCl concentration of 0.25 M.

Example 1.32: Preparation of Coating on PVC Tubing Using Dextran Sulfate 7 and NaCl Concentration of 0.5 M PVC tubing (I.D. 3 mm) was coated according to the general procedure described above. Dextran sulfate 7, see Table 1, was applied at NaCl concentration of 0.5 M.

Example 1.33: Preparation of Coating on PVC Tubing Using Dextran Sulfate 7 and NaCl Concentration of 0.85 M PVC tubing (I.D. 3 mm) was coated according to the general procedure described above. Dextran sulfate 7, see Table 1, was applied at NaCl concentration of 0.85 M.

Example 1.34: Preparation of Coating on PVC Tubing Using Dextran Sulfate 7 and NaCl Concentration of 1.0 M PVC tubing (I.D. 3 mm) was coated according to the general procedure described above. Dextran sulfate 7, see Table 1, was applied at NaCl concentration of 1.0 M.

Example 1.35: Preparation of Coating on PVC Tubing Using Dextran Sulfate 7 and NaCl Concentration of 1.7 M PVC tubing (I.D. 3 mm) was coated according to the general procedure described above. Dextran sulfate 7, see Table 1, was applied at NaCl concentration of 1.7 M.

Example 1.36: Preparation of Coating on PVC Tubing Using Dextran Sulfate 7 and NaCl Concentration of 2.6 M PVC tubing (I.D. 3 mm) was coated according to the general procedure described above. Dextran sulfate 7, see Table 1, was applied at NaCl concentration of 2.6 M.

Example 1.37: Preparation of Coating on PVC Tubing Using Dextran Sulfate 7 and NaCl Concentration of 3.0 M PVC tubing (I.D. 3 mm) was coated according to the general procedure described above. Dextran sulfate 7, see Table 1, was applied at NaCl concentration of 3.0 M.

Example 1.38: Preparation of Coating on PVC Tubing Using Dextran Sulfate 7 and NaCl Concentration of 3.4 M PVC tubing (I.D. 3 mm) was coated according to the general procedure described above. Dextran sulfate 7, see Table 1, was applied at NaCl concentration of 3.4 M.

Example 1.39: Preparation of Coating on PVC Tubing Using Dextran Sulfate 5 and $Na_2HPO_4$ Concentration of 0.05 M PVC tubing (I.D. 3 mm) was coated according to the general procedure described above. Dextran sulfate 5, see Table 1, was applied at $Na_2HPO_4$ concentration of 0.05 M.

Example 1.40: Preparation of Coating on PVC Tubing Using Dextran Sulfate 5 and $Na_2HPO_4$ Concentration of 0.25 M PVC tubing (I.D. 3 mm) was coated according to the general procedure described above. Dextran sulfate 5, see Table 1, was applied at $Na_2HPO_4$ concentration of 0.25 M.

Example 1.41: Preparation of Coating on PVC Tubing Using Dextran Sulfate 5 and $Na_2HPO_4$ Concentration of 0.85 M PVC tubing (I.D. 3 mm) was coated according to the general procedure described above. Dextran sulfate 5, see Table 1, was applied at $Na_2HPO_4$ concentration of 0.85 M.

Example 1.42: Preparation of Coating on PVC Tubing Using Dextran Sulfate 5 and $Na_2HPO_4$ Concentration of 1.7 M PVC tubing (I.D. 3 mm) was coated according to the general procedure described above. Dextran sulfate 5, see Table 1, was applied at $Na_2HPO_4$ concentration of 1.7 M.

Example 1.43: Preparation of Coating on PVC Tubing Using Dextran Sulfate 5 and $Na_2SO_4$ Concentration of 0.05 M PVC tubing (I.D. 3 mm) was coated according to the general procedure described above. Dextran sulfate 5, see Table 1, was applied at $Na_2SO_4$ concentration of 0.05 M.

Example 1.44: Preparation of Coating on PVC Tubing Using Dextran Sulfate 5 and $Na_2SO_4$ Concentration of 0.25 M PVC tubing (I.D. 3 mm) was coated according to the general procedure described above. Dextran sulfate 5, see Table 1, was applied at $Na_2SO_4$ concentration of 0.25 M.

Example 1.45: Preparation of Coating on PVC Tubing Using Dextran Sulfate 5 and $Na_2SO_4$ Concentration of 0.85 M PVC tubing (I.D. 3 mm) was coated according to the general procedure described above. Dextran sulfate 5, see Table 1, was applied at $Na_2SO_4$ concentration of 0.85 M.

Example 1.46: Preparation of Coating on PVC Tubing Using Dextran Sulfate 7 and $Na_2HPO_4$ Concentration of 0.85 M PVC tubing (I.D. 3 mm) was coated according to the general procedure described above. Dextran sulfate 7, see Table 1, was applied at $Na_2HPO_4$ concentration of 0.85 M.

Example 1.47: Preparation of Coating on PVC Tubing Using Dextran Sulfate 7 and Na$_2$SO$_4$ Concentration of 0.85 M PVC tubing (I.D. 3 mm) was coated according to the general procedure described above. Dextran sulfate 7, see Table 1, was applied at Na$_2$SO$_4$ concentration of 0.85 M.

Example 1.48: Preparation of Coating on PUR Tubing Using Dextran Sulfate 7 and NaCl Concentration of 0.05 M PUR tubing (I. D. 3 mm) was coated according to the general procedure described above. Dextran sulfate 7, see Table 1, was applied at NaCl concentration of 0.05 M.

Example 1.49: Preparation of Coating on PUR Tubing Using Dextran Sulfate 7 and NaCl Concentration of 0.25 M PUR tubing (I. D. 3 mm) was coated according to the general procedure described above. Dextran sulfate 7, see Table 1, was applied at NaCl concentration of 0.25 M.

Example 1.50: Preparation of Coating on PUR Tubing Using Dextran Sulfate 7 and NaCl Concentration of 1.7 M PUR tubing (I. D. 3 mm) was coated according to the general procedure described above. Dextran sulfate 7, see Table 1, was applied at NaCl concentration of 1.7 M.

Example 1.51: Preparation of Coating on PUR Tubing Using Dextran Sulfate 7 and NaCl Concentration of 3.0 M PUR tubing (I. D. 3 mm) was coated according to the general procedure described above. Dextran sulfate 7, see Table 1, was applied at NaCl concentration of 3.0 M.

Example 1.52: Preparation of Coating on Steel Coupon Using Dextran Sulfate 7 and NaCl Concentration of 0.05 M A steel coupon (15.0 mm×3.35 mm) was coated according to the general procedure described above. Dextran sulfate 7, see Table 1, was applied at NaCl concentration of 0.05 M.

Example 1.53: Preparation of Coating on Steel Coupon Using Dextran Sulfate 7 and NaCl Concentration of 0.25 M A steel coupon (15.0 mm×3.35 mm) was coated according to the general procedure described above. Dextran sulfate 7, see Table 1, was applied at NaCl concentration of 0.25 M.

Example 1.54: Preparation of Coating on Steel Coupon Using Dextran Sulfate 7 and NaCl Concentration of 1.7 M A steel coupon (15.0 mm×3.35 mm) was coated according to the general procedure described above. Dextran sulfate 7, see Table 1, was applied at NaCl concentration of 1.7 M.

Example 1.55: Preparation of Coating on Steel Coupon Using Dextran Sulfate 7 and NaCl Concentration of 3.0 M A steel coupon (15.0 mm×3.35 mm) was coated according to the general procedure described above. Dextran sulfate 7, see Table 1, was applied at NaCl concentration of 3.0 M.

Example 1.56: Preparation of Coating on PVC Tubing Using Dextran Sulfate 2 and NaCl Concentration of 1.7 M PVC tubing (I.D. 3 mm) was coated according to the general procedure described above. Dextran sulfate 2, see Table 1, was applied at NaCl concentration of 1.7 M.

Example 2a: Normalized Heparin Activity of Coated PVC Tubing Using Different Dextran Sulfates at Varying NaCl Concentration Heparin activity of PVC tubing coated according to Examples 1.11-1.19, 1.21-1.32, 1.34-1.38 (corresponding to dextran sulfates 4, 5, 6 and 7) at varying NaCl concentrations was measured as set out in Evaluation Method B (Heparin activity test).

All coated solid objects tested exhibited heparin activity of at least 1 pmol/cm$^2$ when determined by Evaluation Method B. Heparin activity values shown in Table 2 below are normalized to the highest heparin activity value observed for coated PVC tubing with dextran sulfate 5 at 1.7 M NaCl (Example 1.22).

TABLE 2

Normalized heparin activity (%) of coated PVC tubing with dextran sulfates 4, 5, 6 and 7 at varying NaCl concentration

| Example No. | Dextran sulfate No. NaCl concentration [M] | 4 | 5 | 6 | 7 |
|---|---|---|---|---|---|
| | | Normalized heparin activity [%] | | | |
| 1.11/1.17/1.24/1.29 | 0.05 | 28 | 46 | 27 | 42 |
| 1.12/—/—/1.30 | 0.10 | 33 | — | — | 62 |
| 1.13/1.18/1.25/1.31 | 0.25 | 46 | 62 | 48 | 60 |
| —/1.19/1.26/1.32 | 0.50 | — | 59 | 38 | 78 |
| 1.14/1.21/—/1.34 | 1.00 | 93 | 95 | — | 82 |
| 1.15/1.22/1.27/1.35 | 1.70 | 92 | 100 | 62 | 98 |
| —/—/—/1.36 | 2.60 | — | — | — | 86 |
| 1.16/1.23/1.28/1.37 | 3.00 | 71 | 99 | 50 | 64 |
| —/—/—/1.38 | 3.40 | — | — | — | 38 |

Figure 2:
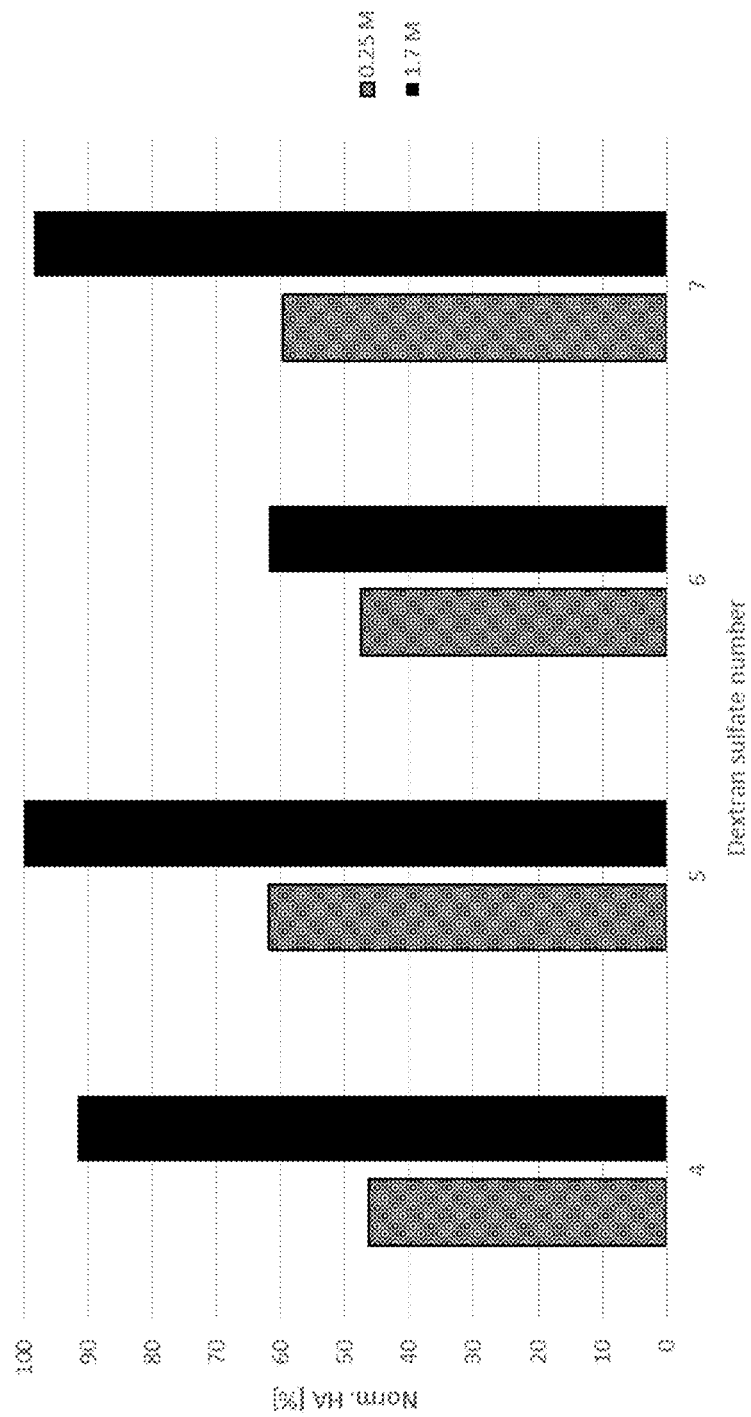
FIG. 2: shows normalized heparin activity (HA) for PVC tubing coated with dextran sulfates 4, 5, 6 and 7 at 0.25 M and 1.7 M NaCl concentration.

Normalized heparin activity values for PVC tubing coated with dextran sulfates 4, 5, 6 and 7 at 0.25 M and 1.7 M NaCl are shown in FIG. 2. It can be seen from FIG. 2 that although both salt concentrations led to coatings with acceptable thromboresistant properties, the use of the higher salt concentration (1.7 M) in the step of adding the dextran sulfate layer led to higher heparin activity than use of the lower salt concentration (0.25 M). It can be seen from Table 2 that the use of salt concentrations of less than 0.25 M resulted in lower heparin activities. The highest heparin activities were obtained using the dextran sulfates with charge density above 6 µeq/g (dextran sulfates 4, 5, 7).

Example 2b: Normalized Heparin Activity of Coated PVC Tubing Using Dextran Sulfate 5, with Different Salts at Varied Concentration Heparin activity of PVC tubing coated according to Examples 1.17, 1.18, 1.20, 1.22, and 1.39-1.45 (corresponding to dextran sulfate 5) using NaCl, Na$_2$HPO$_4$ or Na$_2$SO$_4$, at varying concentrations was measured as set out in Evaluation Method B (Heparin activity test).

All coated solid objects tested exhibited heparin activity of at least 1 pmol/cm$^2$. Heparin activity values shown in Table 3 below are normalized to the highest heparin activity observed for coated PVC tubing with dextran sulfate 5 at 1.70 M NaCl (Example 1.22)

TABLE 3

Normalized heparin activity (%) of coated PVC tubing (dextran sulfate 5) using different salts at varied concentration

| Example No. | Dextran sulfate No. Salt concentration [M] | 5 | | |
|---|---|---|---|---|
| | | Na$_2$HPO$_4$ | Na$_2$SO$_4$ | NaCl |
| | | Normalized heparin activity [%] | | |
| 1.39/1.43/1.17 | 0.05 | 7 | 34 | 46 |
| 1.40/1.44/1.18 | 0.25 | 11 | 18 | 62 |
| 1.41/1.45/1.20 | 0.85 | 25 | 30 | 32 |
| 1.42/—/1.22 | 1.70 | 36 | * | 100 |

* Not soluble in water at 1.7M

Figure 3:
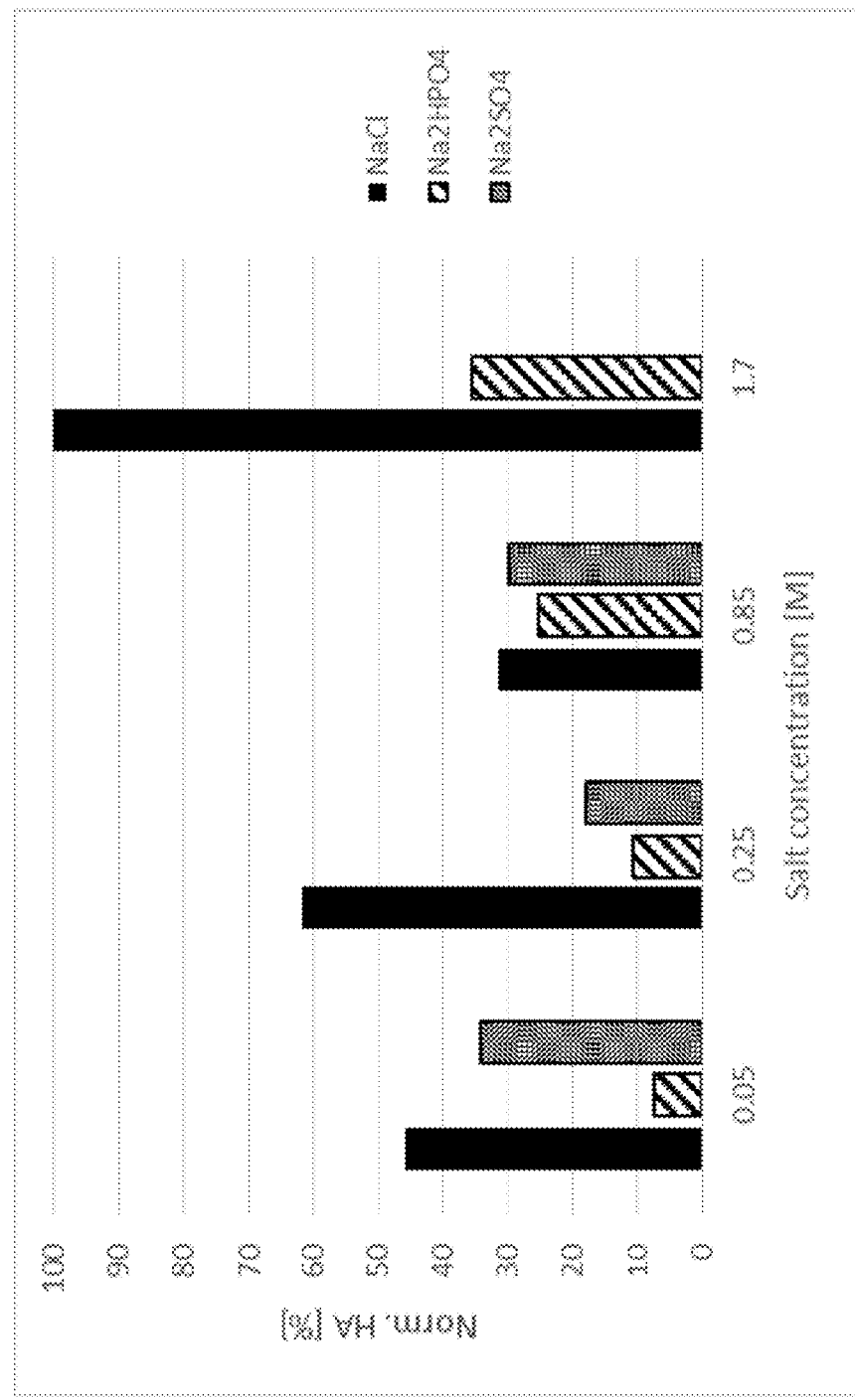
FIG. 3: shows normalized heparin activity (HA) for PVC tubing coated with dextran sulfate 5 using different salts at different concentration.

Normalized heparin activity values from Table 3 are shown in FIG. 3. It can be seen from FIG. 3 that the beneficial effect on heparin activity of using a higher salt concentration in the step of adding the dextran sulfate layer is shown by a range of salts. The highest heparin activity values were obtained using sodium chloride.

Example 2c: Normalized Heparin Activity of Coated PVC Tubing Using Dextran Sulfates 5 and 7, with Different Salts at 0.85 M Concentration Heparin activity of PVC tubing coated according to Examples 1.20, 1.33, 1.41 and 1.45-1.47 (corresponding to dextran sulfate 5 and 7 using NaCl, Na$_2$HPO$_4$ or Na$_2$SO$_4$ at 0.85 M was measured as set out in Evaluation Method B (Heparin activity test).

All coated solid objects tested exhibited heparin activity of at least 1 pmol/cm$^2$. Heparin activity values shown in Table 4 below are normalized to the highest heparin activity value observed for Example 1.22.

TABLE 4

Normalized heparin activity (%) of coated PVC tubing (dextran sulfate 5 and 7) using different salts at 0.85M concentration

| Example No. | Dextran sulfate no. | Salt concentration [M] | Na$_2$HPO$_4$ | Na$_2$SO$_4$ | NaCl |
|---|---|---|---|---|---|
| 1.41/1.45/1.20 | 5 | 0.85 | 25 | 30 | 32 |
| 1.46/1.47/1.33 | 7 | 0.85 | 43 | 38 | 45 |

It can be seen that the use of various salts, e.g. NaCl, Na$_2$HPO$_4$ and Na$_2$SO$_4$, does not significantly affect the heparin activity values. The salt concentration will affect the heparin activity regardless of the salt used.

Example 2d: Normalized Heparin Activity of Various Coated Solid Objects Using Dextran Sulfate 7, with NaCl at Varied Concentration Heparin activity of various coated solid objects according to Examples 1.29, 1.31, 1.35, 1.37, and 1.48-1.55 (corresponding to dextran sulfate 7) using NaCl at varied concentration was measured as set out in Evaluation Method B (Heparin activity test).

All coated solid objects tested exhibited heparin activity of at least 1 pmol/cm$^2$. Heparin activity values shown in Table 5 below are normalized to the highest heparin activity value observed for Example 1.22.

TABLE 5

Normalized heparin activity (%) of various coated solid objects (dextran sulfate 7) with NaCl at varied concentration

| Example No. | Dextran sulfate No. | Salt concentration [M] | PVC | PUR | Steel |
|---|---|---|---|---|---|
| 1.29/1.48/1.52 | 7 | 0.05 | 46 | 40 | 65 |
| 1.31/1.49/1.53 | 7 | 0.25 | 60 | 62 | 81 |
| 1.35/1.50/1.54 | 7 | 1.70 | 98 | 110 | 135 |
| 1.37/1.51/1.55 | 7 | 3.00 | 64 | 72 | 88 |

It is evident from Table 5 that the salt concentration will affect the heparin activity regardless of the material of the solid object that has been coated. Tubing made of polyurethane (PUR) and steel coupons were coated with dextran sulfate 7 at varied salt concentrations and the resulting normalized heparin activity values show that there is a clear salt dependence.

Example 2e: Normalized Heparin Activity of PVC Tubing Coated with Fragments of Heparin (Octasaccharides) Using Dextran Sulfate 5 and a NaCl Concentration of 1.7 M PVC tubing (I.D. 3 mm) was coated with fragments of Heparin (an octasaccharide) according to the general procedure described above with Dextran sulfate 5, see Table 1, applied at NaCl concentration of 1.7 M.

Heparin Fragment Fractions Prepared by Depolymerization of Heparin Followed by Fractionation Oligosaccharides, predominantly of the size of eight sugar units (octa), were prepared by partial nitrous acid cleavage of native heparin followed by fractionation by gel chromatography. An octasaccharide produced by nitrous cleavage is the shortest fragment that can contain a functional active sequence (Thunberg L. et al, FEBS Letters 117 (1980), 203-206).

Depolymerization of heparin: 10 g of heparin sodium was dissolved in 36 ml of water by stirring overnight. 0.30 g NaNO$_2$ was added to the heparin solution and allowed to dissolve. The solution was acidified to pH 2.5 by addition of 4M HCl. After a total reaction time of 2 h at room temperature, the solution was neutralized by addition of 4M NaOH.

The degradation mixture was separated based on molecular size by gel permeation chromatography (GPC), where portions of 3 ml were applied to the column (HiLoad 26/600 Superdex 30 pg, mobile phase 0.15 M NaCl) at a flow rate of 2.5 ml/min. The collected fractions (3 ml) were analyzed for aldehyde by the MBTH reaction, essentially as described in Smith R. L. and Gilkerson E (1979), Anal Biochem 98, 478-480. A broad peak centred on the elution position of the octasaccharide was collected. The combined oligosaccharide elution fractions from several preparative runs were concentrated by evaporation to a volume of 18 ml and re-chromatographed on the same column. For all re-chromatographic runs three fractions, representing deca-, octa- and hexasaccharide fragments, were collected and pooled.

The collected fractions were analysed by Evaluation Method P. The "hexa" fraction consists of a major peak representing hexasaccharide and a shoulder representing octasaccharide. The "octa" fraction consists of a major peak representing octasaccharide with a shoulder representing hexasaccharide and a minor shoulder representing decasaccharide. The "deca" fraction consists of a major peak representing decasaccharide with a shoulder representing octasaccharide and a minor shoulder representing dodecasaccharide.

The concentration of the heparin fragment fractions was determined by Evaluation Method Q (see table below).

|  |  | "Hexa" | "Octa" | "Deca" |
|---|---|---|---|---|
| concentration | mg/ml | 4.0 | 6.2 | 3.6 |

Immobilisation of Octasaccharide

The PVC tubing was coated with sixteen ml of the "octa" fraction diluted with 84 ml of 0.05 M NaCl, the octa fraction was then immobilized to the outermost layer of polyamine via reductive amination, essentially as described by Larm et al. in EP0086186A1 and EP0495820B1 (both incorporated herein by reference in their entirety).

Evaluation by Toluidine Staining of PVC Tubing Coated with Heparin Fragments

The oligosaccharide coated surface was subjected to a toluidine blue staining test as set out in Evaluation Method C. An intense blue/violet color was observed on the luminal surface of the tubing indicating an extensive covalent attachment of the heparin fragments. The homogenous staining obtained for tested tubing indicates formation of a uniform coating.

Evaluation of Heparin Density of PVC Tubing Coated with Heparin Fragments

The heparin density of the surface was determined by Evaluation Method A and the results are shown in the table below.

Evaluation of Heparin Activity of PVC Tubing Coated with Heparin Fragments

The heparin activity of the octasaccharide coated surface (Example 2e) was determined by Evaluation Method B. Heparin activity values shown in the table below are normalized to the highest heparin activity observed for coated PVC tubing with dextran sulfate 5 at 1.70 M NaCl (Example 1.22).

| Example no. | Heparin density ($\mu g/cm^2$) | Heparin activity (%) |
|---|---|---|
| 2e | 5.6 | 5 |
| 1.22 | 6.5 | 100 |

Although the heparin density value of the octasaccharide coating (Example 2e) and the heparin coating (Example 1.22) were similar, the AT binding capacity (heparin activity; 'HA') of the octasaccharide coatings was low compared to the heparin coating. However, this is to be expected considering the relatively low anti-FXa activity exhibited by the octasaccharide fraction in solution (data not shown). Thus, the octasaccharide fragments appear to substantially retain their AT-binding capacity after immobilization.

Example 3a: Heparin Concentration of Coated PVC Tubing Using Different Dextran Sulfates at Varied NaCl Concentration Heparin concentration of solid objects (PVC tubing) coated according to Examples 1.4-1.19, 1.21-1.32 and 1.34-1.38 (corresponding to dextran sulfates 3, 4, 5, 6 and 7) at varying NaCl concentrations was measured as set out in Evaluation Method A.

All coated solid objects tested exhibited heparin concentration of at least 1 $\mu g/cm^2$. Heparin concentration values are shown in Table 6 below.

TABLE 6

Heparin concentration ($\mu g/cm^2$) of coated PVC tubing with dextran sulfates 3, 4, 5, 6 and 7 at varied NaCl concentration

| Example No. | Salt concentration [M] | Dextran sulfate No. 3 (Ref Ex) | 4 | 5 | 6 | 7 |
|---|---|---|---|---|---|---|
|  |  | Heparin concentration [$\mu g/cm^2$] | | | | |
| 1.4/1.11/1.17/1.24/1.29 | 0.05 | 4.8 | 2.9 | 3.4 | 2.9 | 4.0 |
| 1.5/1.12/—/—/1.30 | 0.10 | 4.8 | 3.2 | — | — | 4.7 |
| 1.6/1.13/1.18/1.25/1.31 | 0.25 | 5.1 | 3.0 | 3.7 | 3.9 | 5.7 |
| —/—/1.19/1.26/1.32 | 0.50 | — | — | 4.5 | 4.8 | 5.7 |
| 1.7/1.14/1.21/—/1.34 | 1.00 | 5.1 | 4.1 | 4.5 | — | 6.8 |
| 1.8/1.15/1.22/1.27/1.35 | 1.70 | 4.3 | 4.7 | 6.5 | 6.0 | 6.8 |
| 1.9/—/—/—/1.36 | 2.60 | 3.1 | — | — | — | 6.9 |
| 1.10/1.16/1.23/1.28/1.37 | 3.00 | 2.0 | 5.0 | 4.1 | 5.0 | 7.3 |
| —/—/—/—/1.38 | 3.40 | — | — | — | — | 6.2 |

Figure 4:
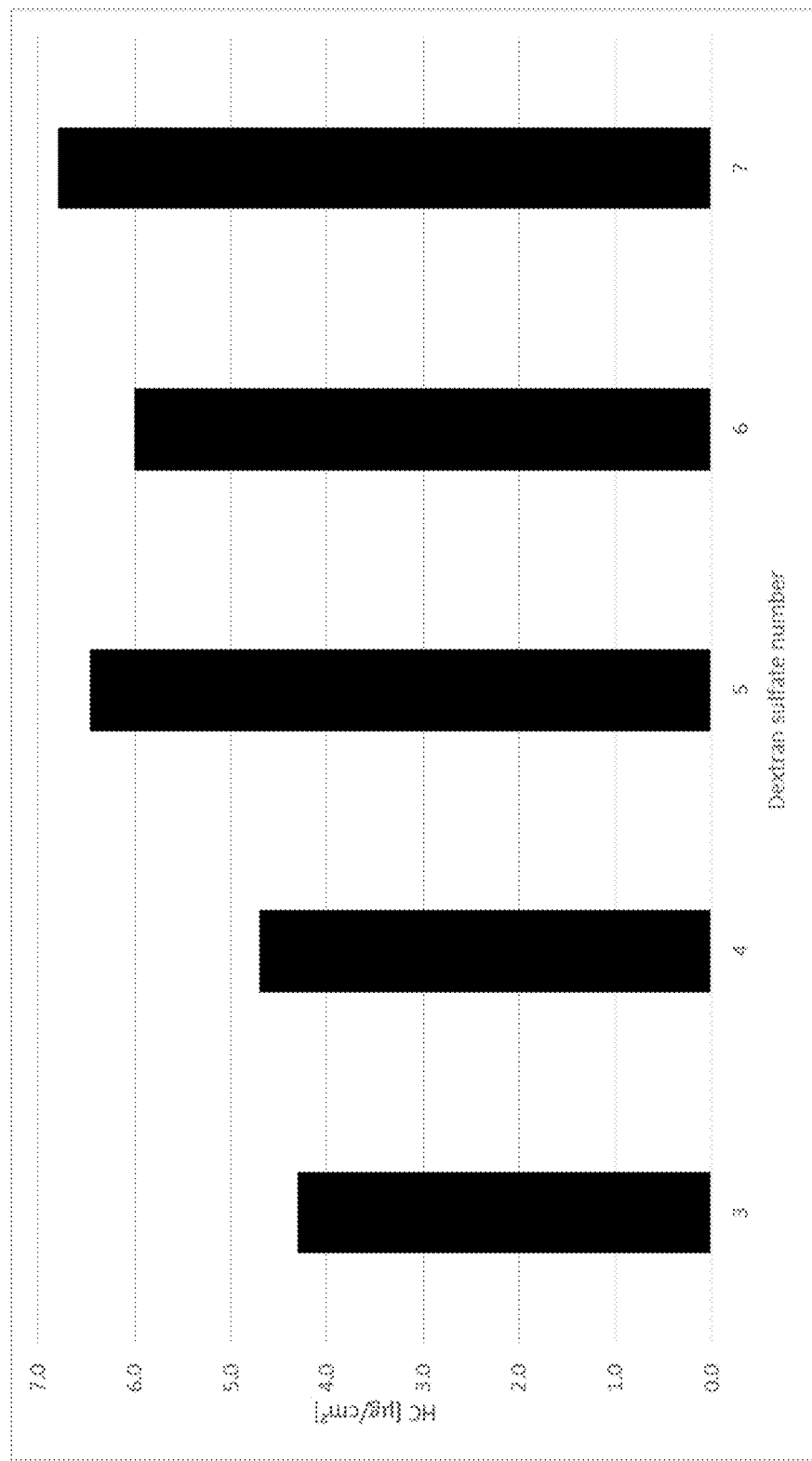
FIG. 4: shows heparin concentration (HC) for PVC tubing coated with dextran sulfates 3, 4, 5, 6 and 7 at 1.7 M NaCl concentration.

Heparin concentration for PVC tubing coated with dextran sulfates 3, 4, 5, 6 and 7 at 1.7 M NaCl are shown in FIG. 4. It can be seen from FIG. 4 that there is a trend to higher heparin concentration from using a dextran sulfate of higher molecular weight in the step of adding the dextran sulfate layer under these conditions. Dextran sulfate 3 is a reference dextran sulfate in this example.

Figure 5:
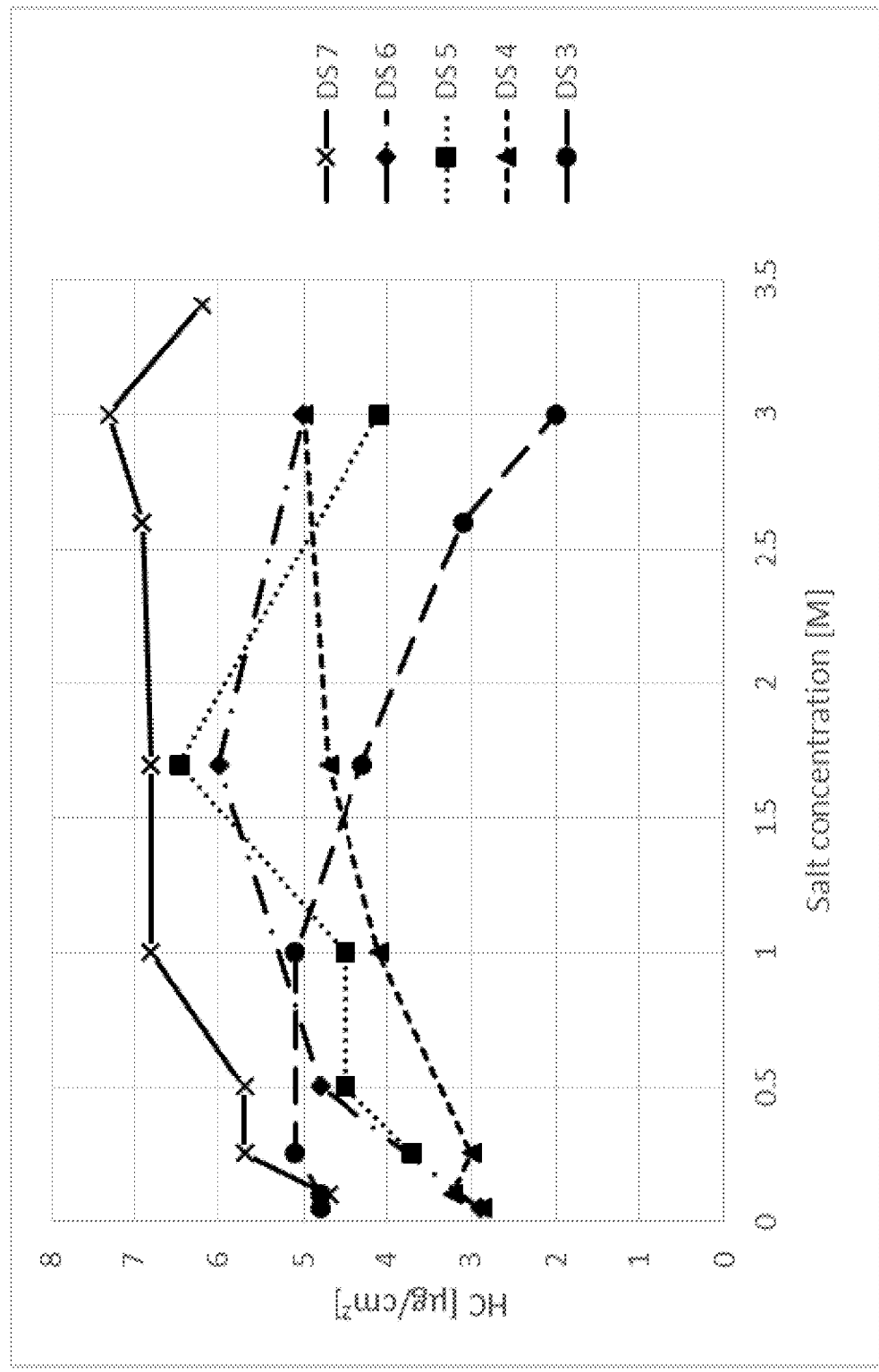
FIG. 5: shows heparin concentration (HC) for PVC tubing coated with dextran sulfates 3, 4, 5, 6 and 7 at varied NaCl concentration.

Heparin concentration for PVC tubing coated with dextran sulfates 3, 4, 5, 6 and 7 at varied NaCl concentration are shown in FIG. 5. It can be seen from FIG. 5 that dextran sulfates 4, 5, 6 and 7 demonstrate a trend to higher heparin concentration with increased salt concentration (at least up to 1.7 M) in the step of adding the dextran sulfate layer. It can be seen that the use of salt concentrations of less than 0.25 M generally results in lower heparin activities. Dextran sulfate 3 does not follow this trend and when it is used the heparin concentration lowers as the salt concentration in this step is increased. Dextran sulfate 3 is a reference dextran sulfate in this example. Without being limited by theory, the inventors attribute this difference in trend to the fact that dextran sulfate 3 has a much lower charge density than dextran sulfates 4, 5, 6 and 7.

Example 3b: Heparin Concentration of Coated PVC Tubing Using Dextran Sulfate 5, with Different Salts at Varied Concentration Heparin concentration of PVC tubing coated according to Examples 1.17, 1.18, 1.20, 1.22 and 1.39-1.45 (corresponding to dextran sulfate 5 using NaCl, $Na_2HPO_4$ or $Na_2SO_4$, at varying concentrations was measured as set out in Evaluation Method A.

All coated solid objects tested exhibited heparin concentration of at least 1 $\mu g/cm^2$. Heparin concentration values are shown in Table 7 below.

TABLE 7

Heparin concentration (μg/cm²) of coated PVC tubing (dextran sulfate 5) using different salts at varied concentration

| Example No. | Dextran sulfate No. Salt concentration [M] | Salt 5 Na₂HPO₄ | 5 Na₂SO₄ | 5 NaCl |
|---|---|---|---|---|
| | | Heparin concentration [μg/cm²] | | |
| 1.39/1.43/1.17 | 0.05 | 2.7 | 3.3 | 3.4 |
| 1.40/1.44/1.18 | 0.25 | 3.2 | 3.5 | 3.7 |
| 1.41/1.45/1.20 | 0.85 | 5.0 | 4.2 | 3.5 |
| 1.42/—/1.22 | 1.70 | 5.1 | * | 6.5 |

* Na₂SO₄ not soluble in water at 1.7M

Figure 6:
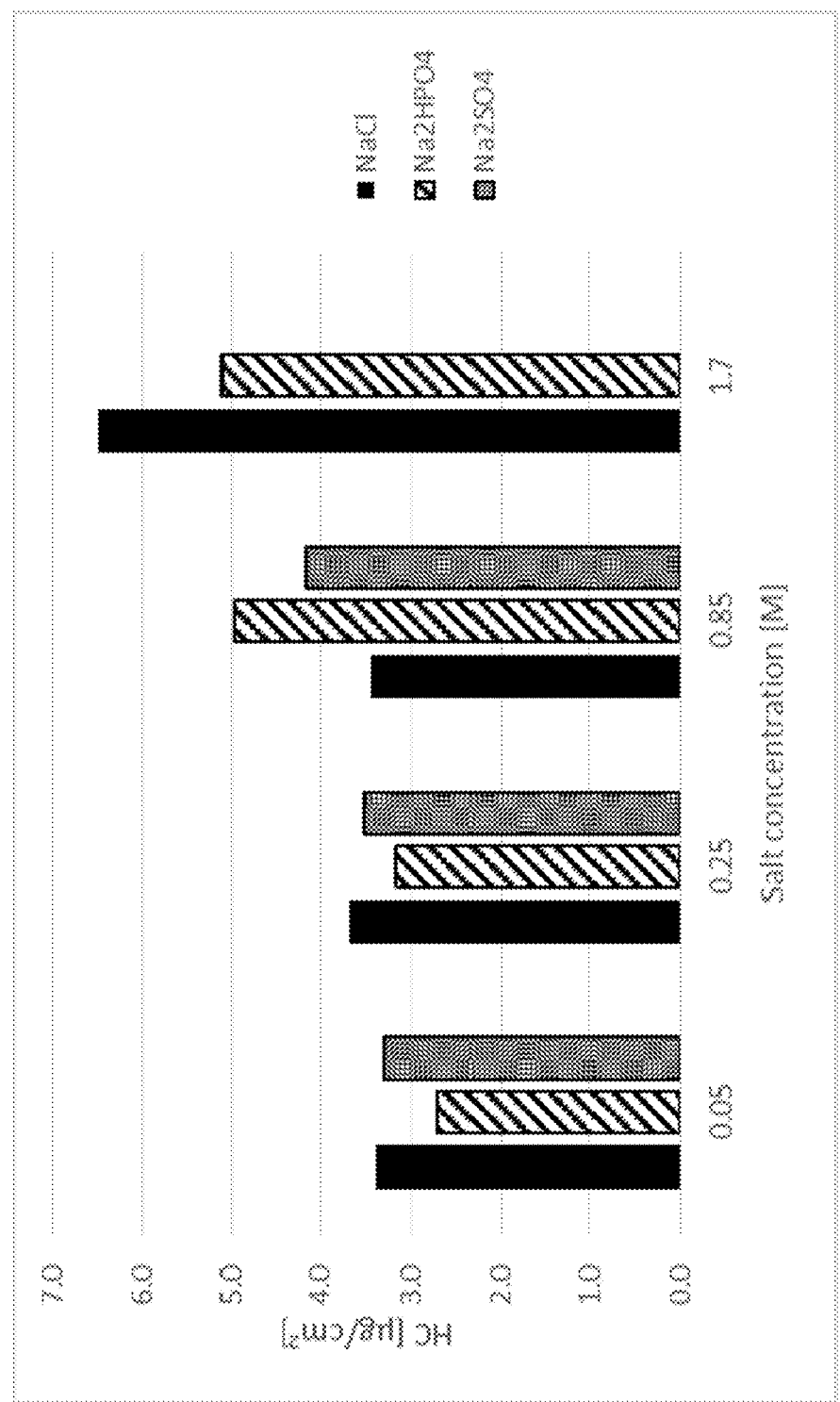
FIG. 6: shows heparin concentration (HC) for PVC tubing coated with dextran sulfate 5 using different salts at different concentration.

Heparin concentration values from Table 7 are shown in FIG. 6. It can be seen from FIG. 6 that dextran sulfate 5 demonstrates a trend to increased heparin concentration with increased salt concentration in the step of adding the dextran sulfate layer, for a range of different salts.

Example 3c: Heparin Concentration of Coated PVC Tubing Using Dextran Sulfates 5 and 7, with Different Salts at 0.85 M Concentration Heparin concentration of PVC tubing coated according to Examples 1.20, 1.33, 1.41, 1.45, 1.46 and 1.47 (corresponding to dextran sulfate 5 and 7 using NaCl, Na₂HPO₄ or Na₂SO₄ at 0.85 M was measured as set out in Evaluation Method A.

All coated solid objects tested exhibited heparin concentration of at least 1 μg/cm². Heparin concentration values are shown in Table 8 below.

TABLE 8

Heparin concentration (μg/cm²) of coated PVC tubing (dextran sulfates 5 and 7) using different salts at 0.85M concentration

| Example No. | Dextran sulfate No. | Salt concentration [M] | Na₂HPO₄ | Na₂SO₄ | NaCl |
|---|---|---|---|---|---|
| 1.41/1.45/1.20 | 5 | 0.85 | 5.0 | 4.2 | 3.5 |
| 1.46/1.47/1.33 | 7 | 0.85 | 3.3 | 3.6 | 3.7 |

It can be seen that the use of various salts, e.g. NaCl, Na₂HPO₄ and Na₂SO₄, does not significantly affect the heparin concentration values.

Example 3d: Heparin Concentration of Various Coated Solid Objects Using Dextran Sulfate 7, with NaCl at Varied Concentration Heparin concentration of various solid objects according to Examples 1.29, 1.31, 1.35, 1.37, and 1.48-1.55. (corresponding to dextran sulfate 7 (12)) coated using NaCl at varied concentration was measured as set out in Evaluation Method A.

All coated solid objects tested exhibited heparin concentration of at least 1 μg/cm². Heparin concentration values are shown in Table 9 below.

TABLE 9

Heparin concentration (μg/cm²) of various coated solid objects (dextran sulfate 7 with NaCl at varied concentration

| Example No. | Dextran sulfate No. | Salt concentration [M] | PVC | PUR | Steel |
|---|---|---|---|---|---|
| 1.29/1.48/1.52 | 7 | 0.05 | 4.0 | 2.9 | 7.2 |
| 1.31/1.49/1.53 | 7 | 0.25 | 5.7 | 2.5 | 7.7 |
| 1.35/1.50/1.54 | 7 | 1.70 | 6.8 | 3.5 | 10.4 |
| 1.37/1.51/1.55 | 7 | 3.00 | 7.3 | 4.1 | 8.9 |

It is evident from Table 9 that the salt concentration will affect the heparin concentration regardless of the material of the solid object that has been coated. Tubing made of polyurethane (PUR) and steel coupons were coated with dextran sulfate 7 at varied salt concentrations and the resulting heparin concentration values show that there is a clear salt dependence.

Example 4a: Zeta Potential Measurement of Coated PVC Tubing Using Different Dextran Sulfates at 1.7 M and 0.25 M NaCl Concentration The surface charge of PVC tubing coated according to Examples 1.1, 1.2, 1.3, 1.6, 1.8, 1.13, 1.15, 1.18, 1.22, 1.25, 1.27, 1.31, 1.35 and 1.56 (corresponding to dextran sulfates 1, 2, 3, 4, 5, 6 and 7) at varied NaCl concentration) was measured as set out in Evaluation Method D.

The zeta potential values for PVC coated tubing with dextran sulfates 1 to 7 at 1.7 M NaCl are shown in Table 10.

TABLE 10

The zeta potential for PVC coated tubing with dextran sulfates 1 to 7 at 1.7M NaCl

| Example No. | Dextran sulfate No. | Delta value [mV] | pH (global minimum) | IEP |
|---|---|---|---|---|
| 1.2 | 1 (Reference example dextran sulfate) | 20 | 6.1 | 2.6 |
| 1.56 | 2 (Reference example dextran sulfate) | 18 | 5.6 | 2.6 |
| 1.8 | 3 (Reference example dextran sulfate) | 13 | 4.7 | 2.1 |
| 1.15 | 4 | 30 | 4.4 | 2.6 |
| 1.22 | 5 | 28 | 4.5 | 2.5 |
| 1.27 | 6 | 41 | 3.8 | 2.3 |
| 1.35 | 7 | 40 | 4.2 | 2.4 |

Dextran sulfates 1 to 7 all have an IEP below pH 3. However, the lower molecular weight dextran sulfates (Reference example dextran sulfates 1-3) do not fulfill all the preferred features (i.e. the potential fingerprint for solid objects coated according to the process of the invention, described above). Dextran sulfates 1 and 2 have a global minimum occurring at a pH higher than 5 and dextran sulfate 3 has a delta value which is lower than 20 mV. Solid objects of the invention coated with dextran sulfates 4 to 7 do fulfill these criteria.

Figure 7:
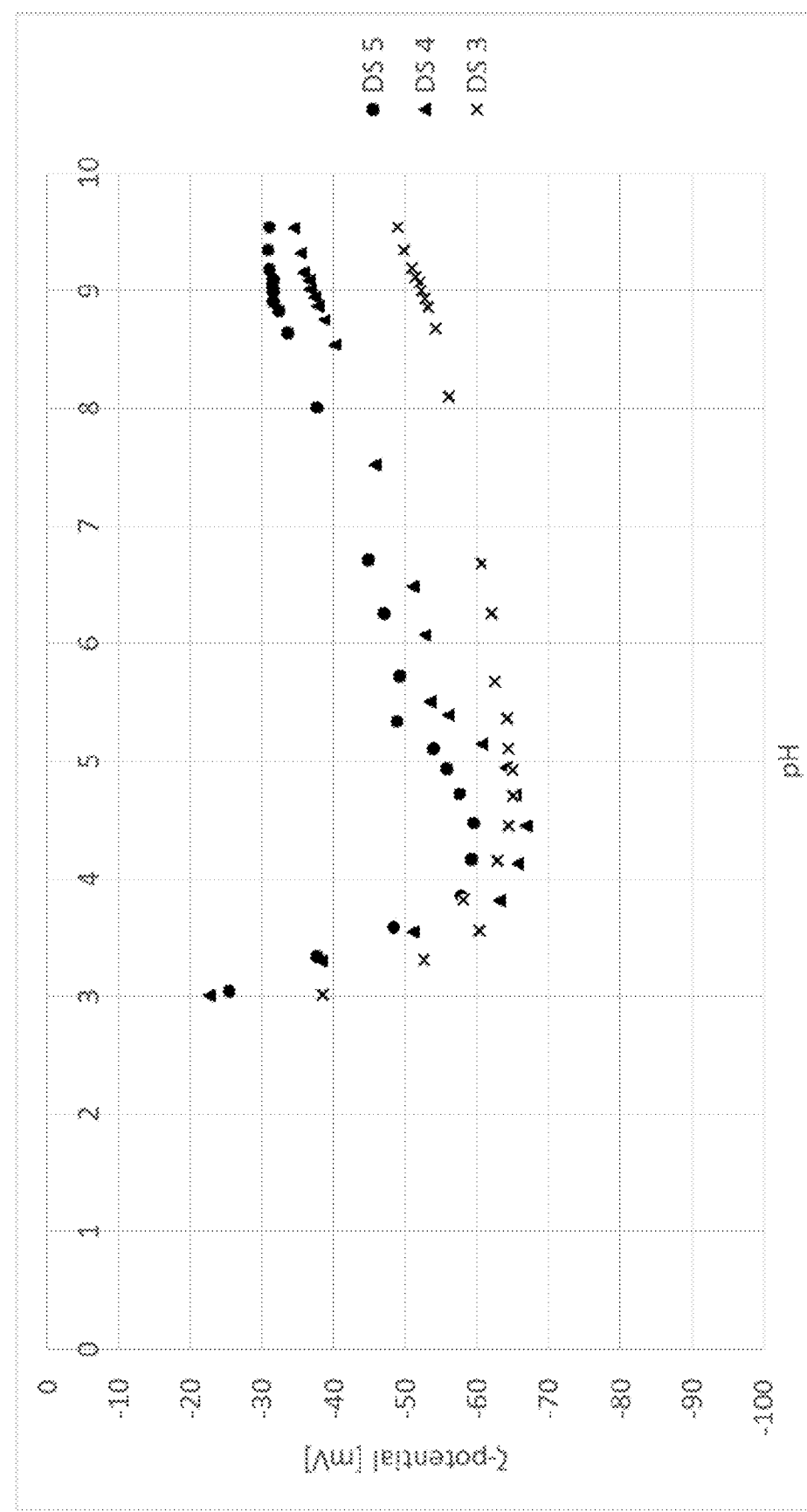
FIG. 7: shows zeta potential for PVC tubing coated with dextran sulfates 3, 4 and 5 at 1.7 M NaCl concentration.

The zeta potential for PVC coated tubing with dextran sulfates 3, 4 and 5 at 1.7 M NaCl (corresponding to Examples 1.8, 1.15 and 1.22) are shown in FIG. 7.

Figure 8:
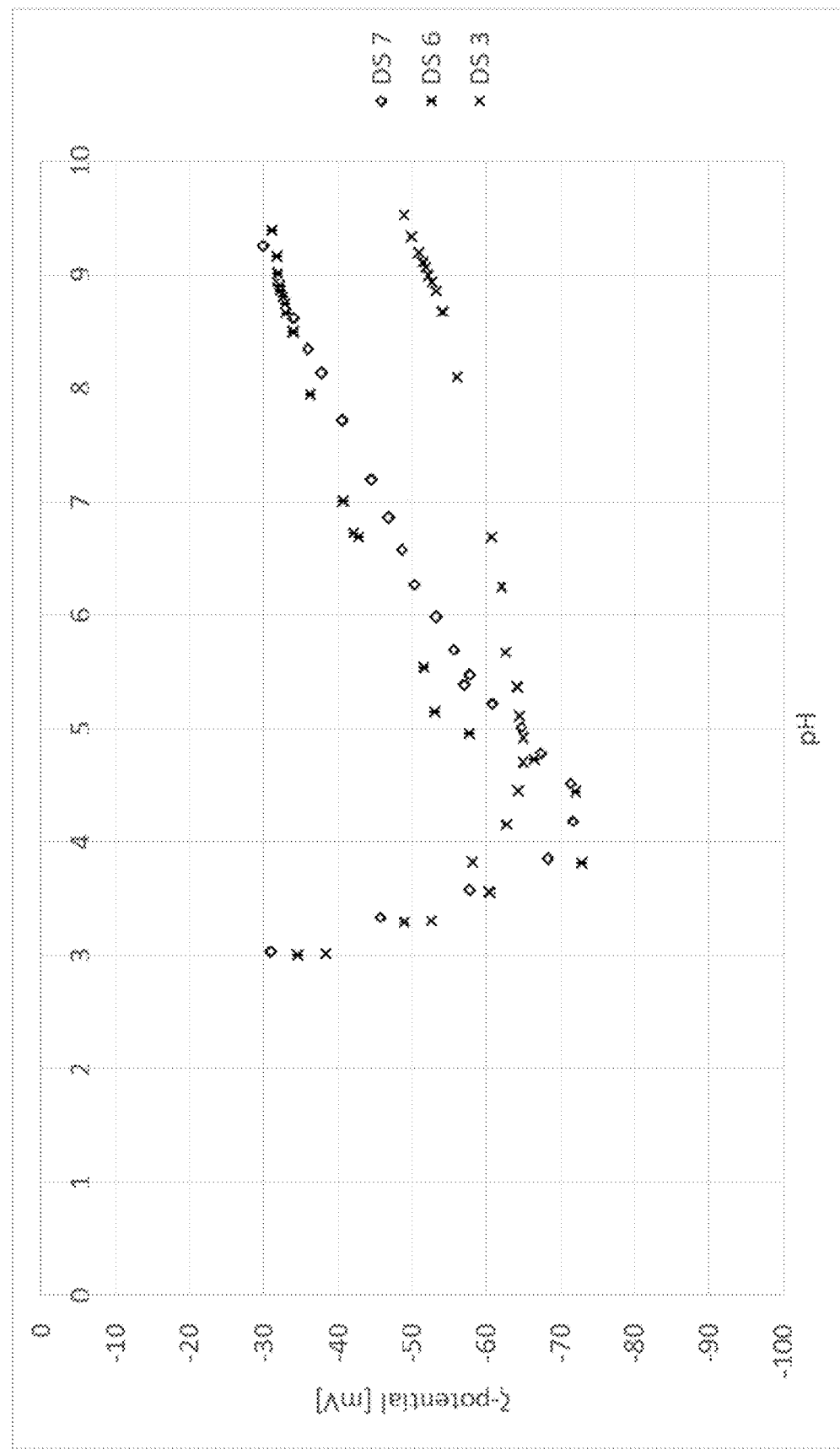
FIG. 8: shows zeta potential for PVC tubing coated with dextran sulfates 3, 6 and 7 at 1.7 M NaCl concentration.

The zeta potential for PVC coated tubing with dextran sulfates 3, 6 and 7 at 1.7 M NaCl (corresponding to Examples 1.8, 1.27 and 1.35) are shown in FIG. 8.

The zeta potential values for PVC coated tubing with dextran sulfates 1 to 7 at 0.25 M NaCl are shown in Table 11.

TABLE 11

The zeta potential for PVC coated tubing with dextran sulfates 1 to 7 at 0.25M NaCl

| Example No. | Dextran sulfate No. | Delta value [mV] | pH (global minimum) | IEP |
|---|---|---|---|---|
| 1.1 | 1 (Reference example dextran sulfate) | 17 | 4.6 | 2.6 |
| 1.3 | 2 (Reference example dextran sulfate) | 23 | 6.1 | 2.7 |
| 1.6 | 3 (Reference example dextran sulfate) | 15 | 4.2 | 1.5 |
| 1.13 | 4 | 37 | 4.5 | 2.7 |
| 1.18 | 5 | 38 | 4.5 | 2.6 |
| 1.25 | 6 | 35 | 4.1 | 2.5 |
| 1.31 | 7 | 36 | 4.5 | 2.5 |

Dextran sulfates 1 to 7 all have an IEP below pH 3. However, the lower molecular weight dextran sulfates (Reference example dextran sulfates 1-3) do not fulfill all the preferred features (i.e. the potential fingerprint for solid objects coated according to the process of the invention, described above). Dextran sulfate 2 has a global minimum occurring at a pH higher than 5 and dextran sulfates 1 and 3 have a delta value which is lower than 20 mV. Solid objects of the invention coated with dextran sulfates 4 to 7 do fulfill these criteria.

Figure 9:
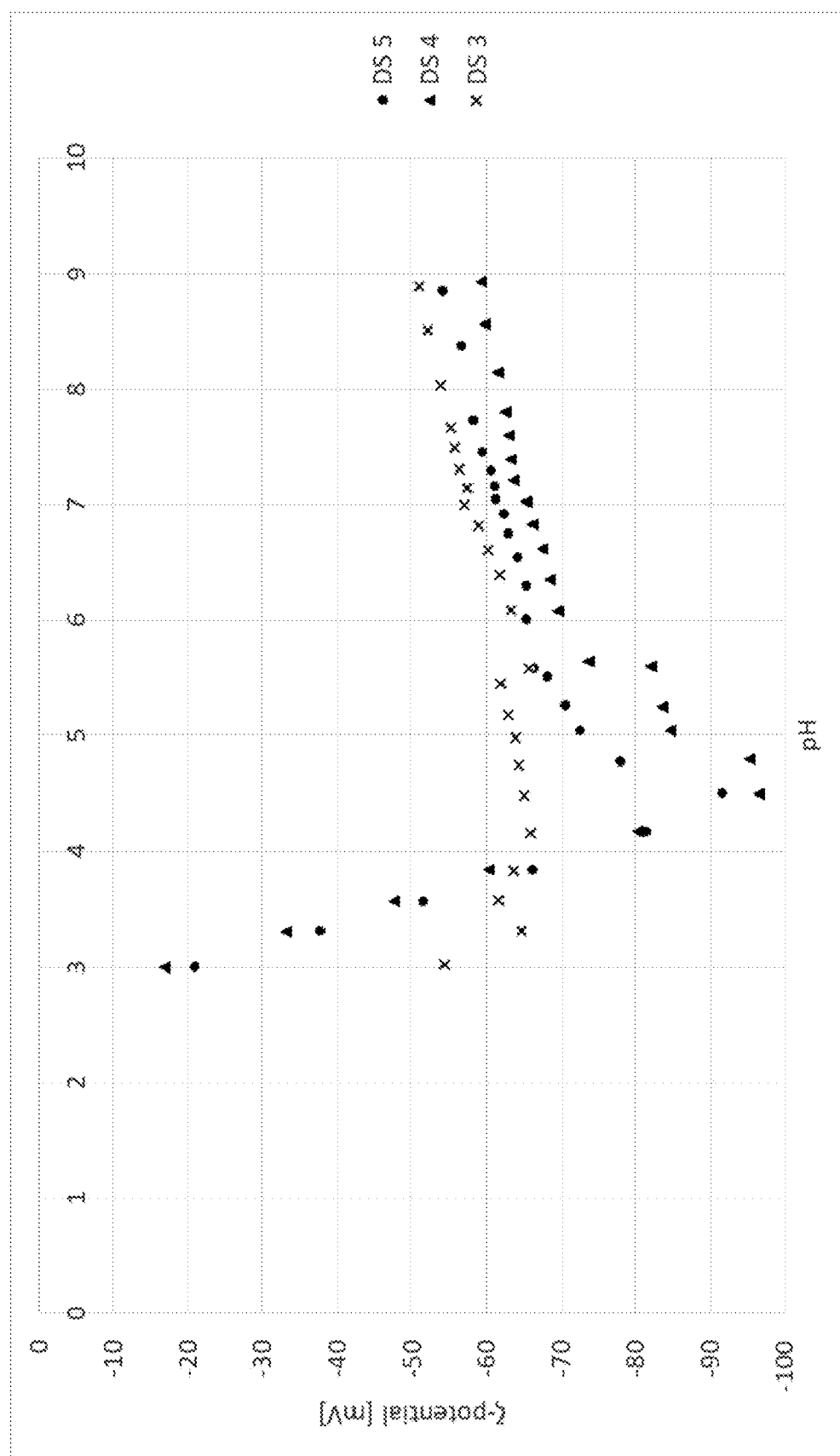
FIG. 9: shows zeta potential for PVC tubing coated with dextran sulfates 3, 4 and 5 at 0.25 M NaCl concentration.

The zeta potential for PVC coated tubing with dextran sulfates 3, 4 and 5 at 0.25 M NaCl (corresponding to Examples 1.6, 1.13 and 1.18) are shown in FIG. 9.

Figure 10:
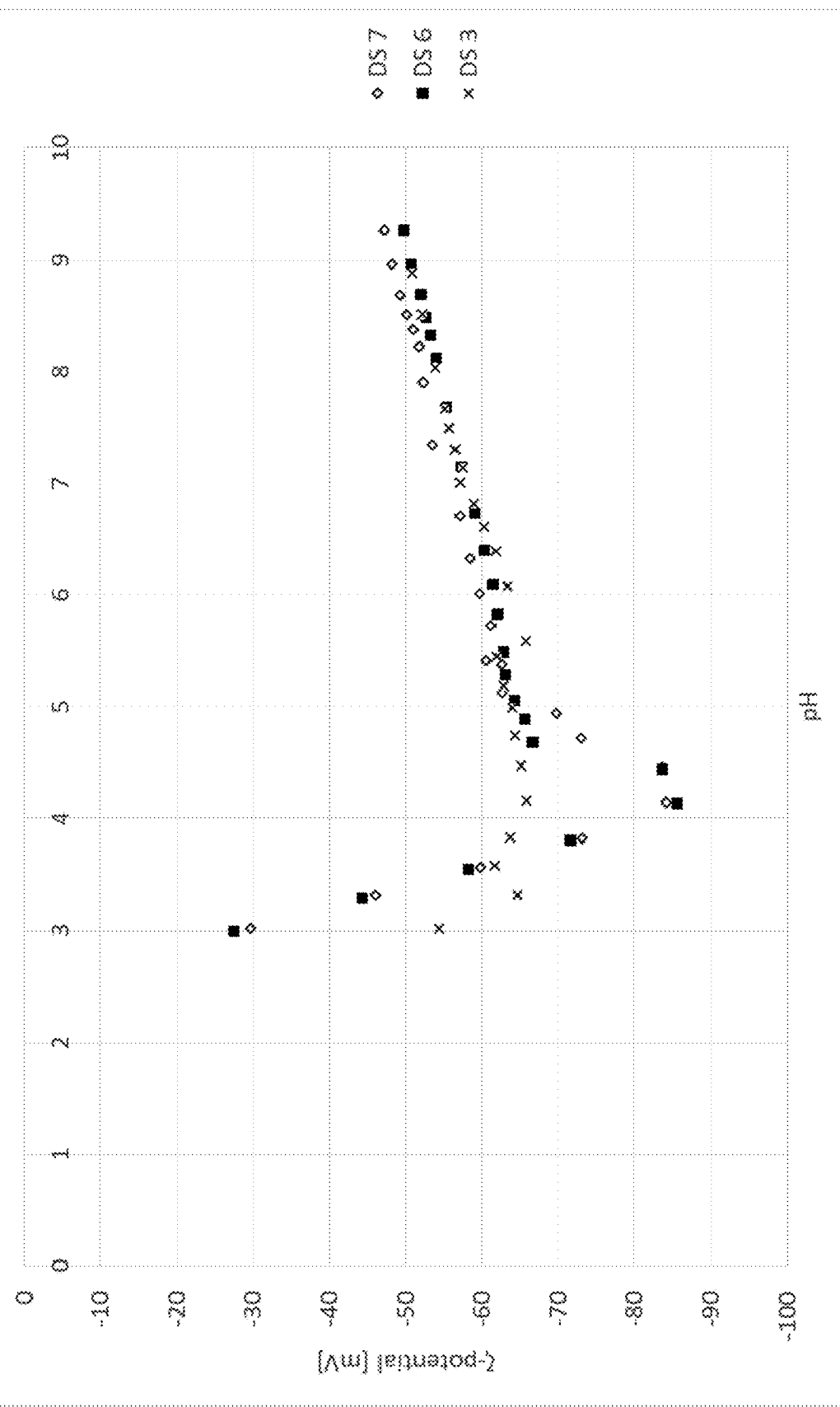
FIG. 10: shows zeta potential for PVC tubing coated with dextran sulfates 3, 6 and 7 at 0.25 M NaCl concentration.

The zeta potential for PVC coated tubing with dextran sulfates 3, 6, and 7 at 0.25 M NaCl (corresponding to Examples 1.6, 1.25 and 1.31) are shown in FIG. 10.

Example 4b: Zeta Potential Measurement of Coated PVC Tubing Using Dextran Sulfate 5 with Different Salts at Varied Concentration The surface charge of PVC tubing coated according to Examples 1.18, 1.22, 1.39-1.42 and 1.44-1.45 (all dextran sulfate 5) using NaCl, $Na_2HPO_4$ or $Na_2SO_4$, at varying concentrations was measured as set out in Evaluation Method D.

The zeta potential values for PVC coated tubing with dextran sulfate 5 at different NaCl concentrations are shown in Table 12.

TABLE 12

The zeta potential for PVC coated tubing with dextran sulfate 5 at different NaCl concentrations

| Example No. | Salt concentration [M] | Delta value [mV] | pH (global minimum) | IEP |
|---|---|---|---|---|
| 1.18 | 0.25 | 38 | 4.5 | 2.4 |
| 1.22 | 1.7 | 28 | 4.5 | 2.5 |

Figure 11:
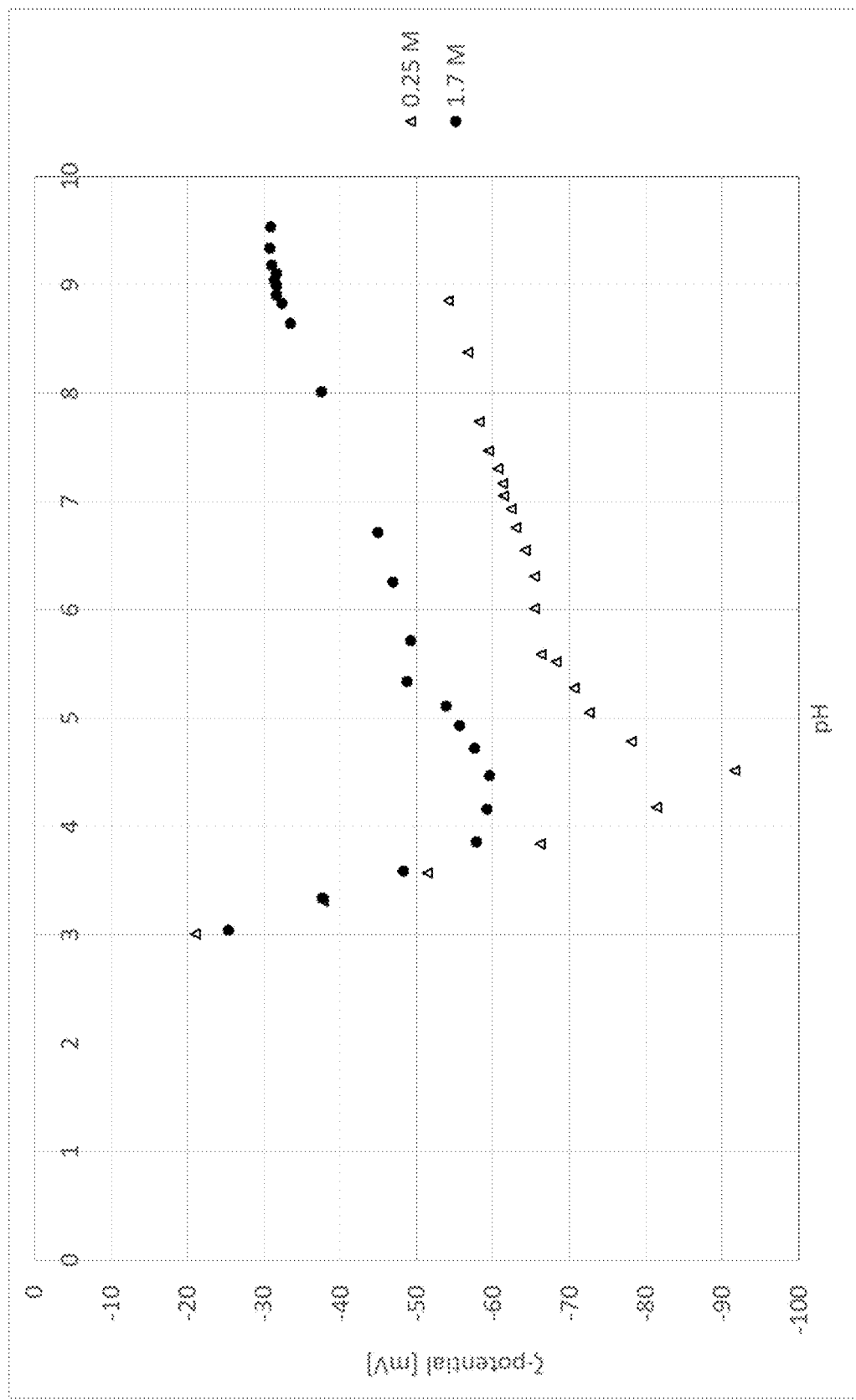
FIG. 11: shows zeta potential for PVC tubing coated with dextran sulfate 5 at varied NaCl concentration.

The zeta potential profiles for PVC coated tubing with dextran sulfate 5 at NaCl concentrations of 0.25 M and 1.7 M (corresponding to Examples 1.18 and 1.22) are shown in FIG. 11 where the salt effect on the zeta potential is evident.

The preferred features (i.e. the potential fingerprint for solid objects coated according to the process of the invention, described above) are fulfilled at 0.25 and 1.7 M NaCl concentration.

The zeta potential values for PVC coated tubing with dextran sulfate 5 at different $Na_2HPO_4$ concentrations are shown in Table 13.

TABLE 13

The zeta potential for PVC coated tubing with dextran sulfate 5 at different $Na_2HPO_4$ concentrations

| Example No. | Salt concentration [M] | Delta value [mV] | pH (global minimum) | IEP |
|---|---|---|---|---|
| 1.39 | 0.05 | 20 | 4.2 | 2.6 |
| 1.40 | 0.25 | 28 | 4.3 | 2.4 |
| 1.41 | 0.85 | 41 | 4.5 | 2.6 |
| 1.42 | 1.70 | 38 | 4.2 | 2.7 |

Figure 12:
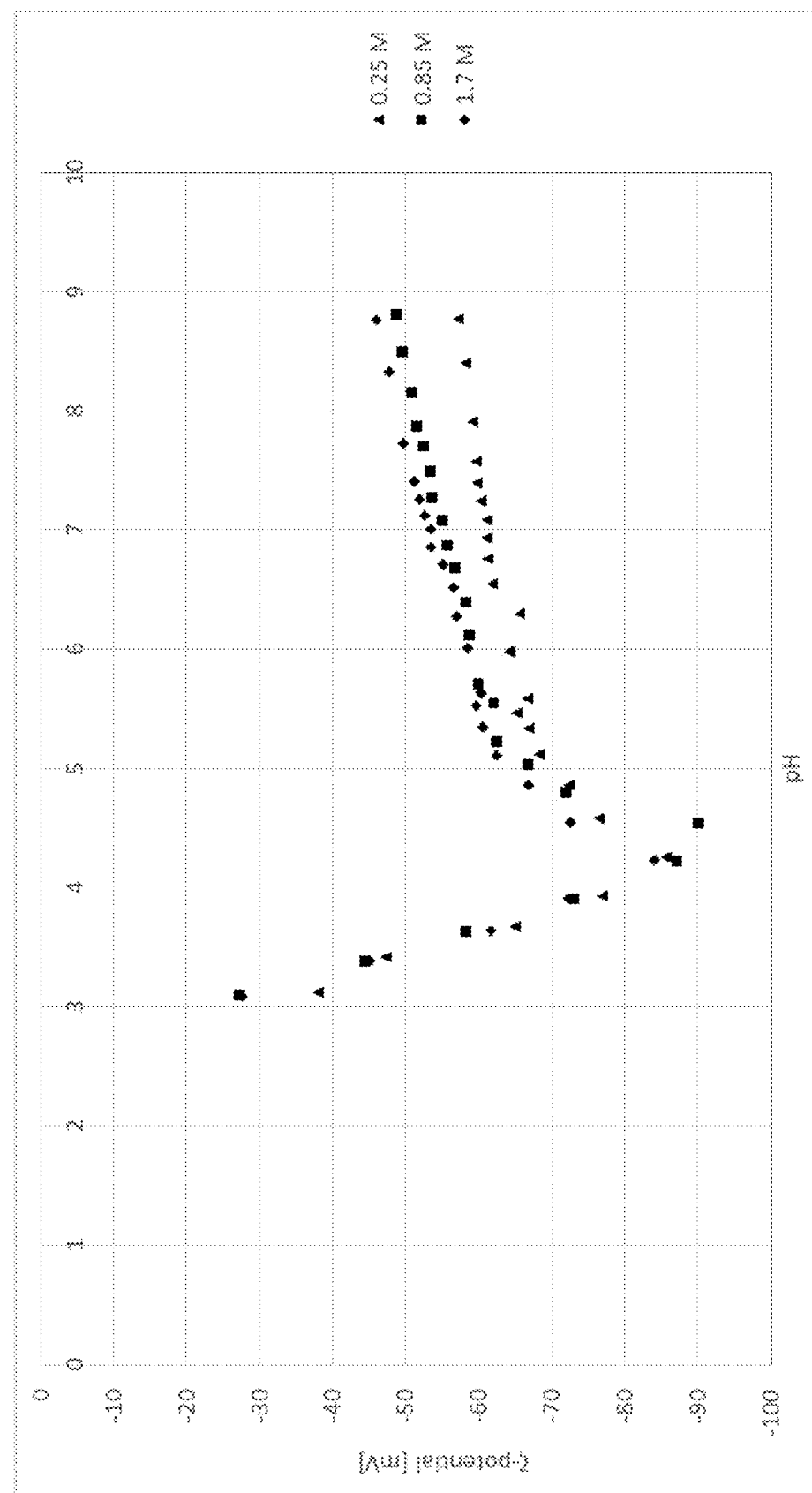
FIG. 12: shows zeta potential for PVC tubing coated with dextran sulfate 5 at varied $Na_2HPO_4$ concentration.

The zeta potential profiles for PVC coated tubing with dextran sulfate 5 at $Na_2HPO_4$ concentrations of 0.25 M, 0.85 M and 1.7 M (corresponding to Examples 1.40, 1.41 and 1.42) are shown in FIG. 12 where it can be seen that all the preferred features (i.e. the potential fingerprint for solid objects coated according to the process of the invention, described above) are fulfilled using $Na_2HPO_4$ at different concentrations.

The zeta potential values for PVC coated tubing with dextran sulfate 5 at different $Na_2SO_4$ concentrations are shown in Table 14.

TABLE 14

The zeta potential for PVC coated tubing with dextran sulfate 5 at different $Na_2SO_4$ concentrations

| Example No. | Salt concentration [M] | Delta value [mV] | pH (global minimum) | IEP |
|---|---|---|---|---|
| 1.44 | 0.25 | 40 | 4.5 | 2.6 |
| 1.45 | 0.85 | 39 | 4.3 | 2.6 |
| N/A** | 1.7 | * | * | * |

* Not soluble in water at 1.7M
**N/A = Not applicable

Figure 13:
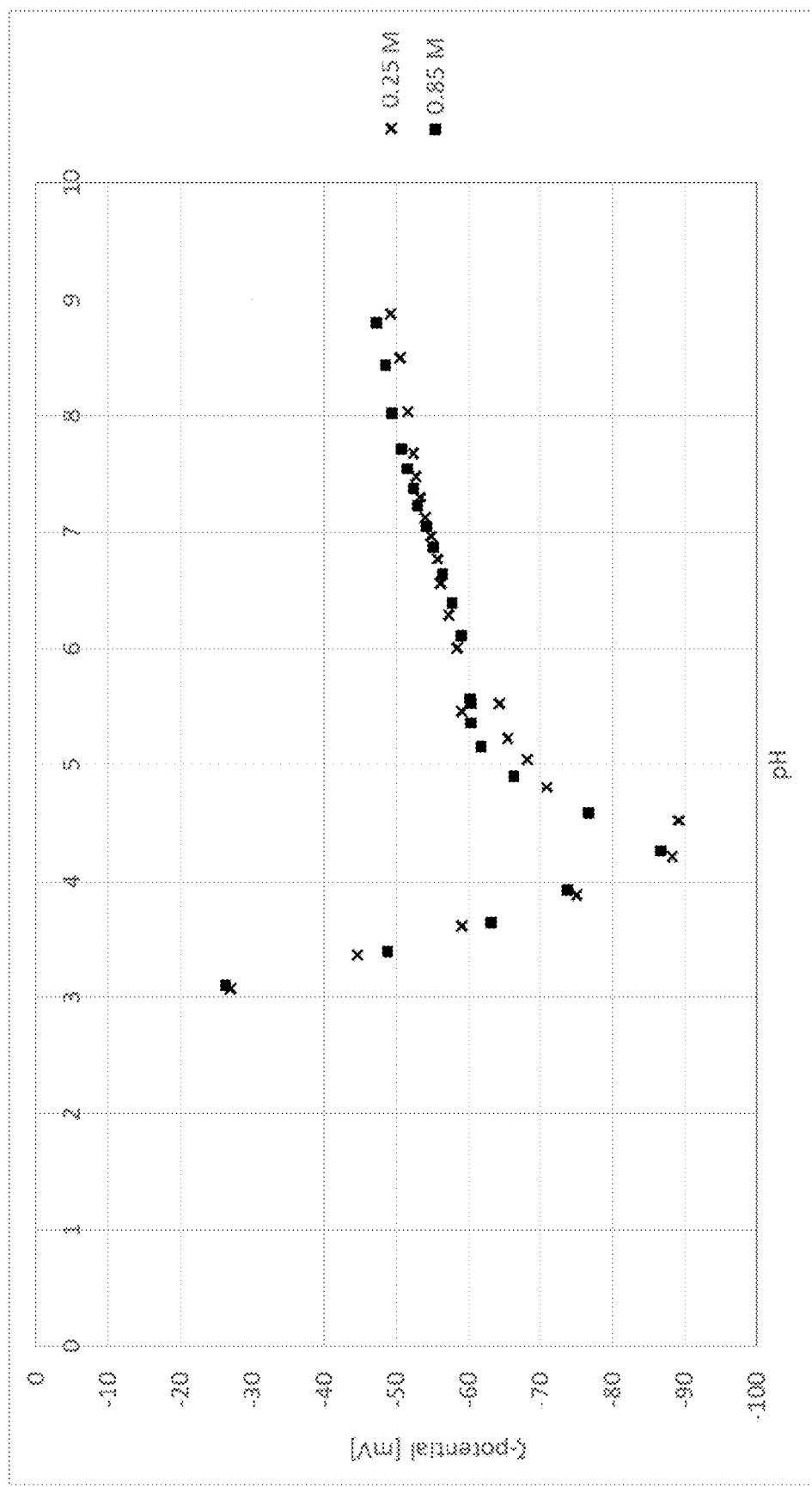
FIG. 13: shows zeta potential for PVC tubing coated with dextran sulfate 5 at varied $Na_2SO_4$ concentration.

The zeta potential profiles for PVC coated tubing with dextran sulfate 5 at $Na_2SO_4$ concentration of 0.25 M and 0.85 M (corresponding to Examples 1.44 and 1.45) are shown in FIG. 13 where it can be seen that all the preferred features (i.e. the potential fingerprint for solid objects coated according to the process of the invention, described above) are fulfilled using $Na_2SO_4$ concentrations at different concentrations. It is evident from Tables 12, 13 and 14 that using different types of salt at different concentrations will not significantly affect the zeta potential profile. It is also clear that there is a salt dependence for the different salt types.

Example 5: Blood Contact Activation (Platelet Loss and F1+2) of Coated PVC Tubing Using Different Dextran Sulfates at Varied NaCl Concentration The percentage of platelets preserved and the F1+2 (prothrombin fragment) after blood exposure of PVC tubing coated according to Examples 1.1, 1.3, 1.13, 1.18, 1.25 and 1.31 (corresponding to dextran sulfates 1, 2, 4, 5, 6 and 7) at varied NaCl concentration were measured as set out in Evaluation Methods E and F, respectively.

Figure 14:
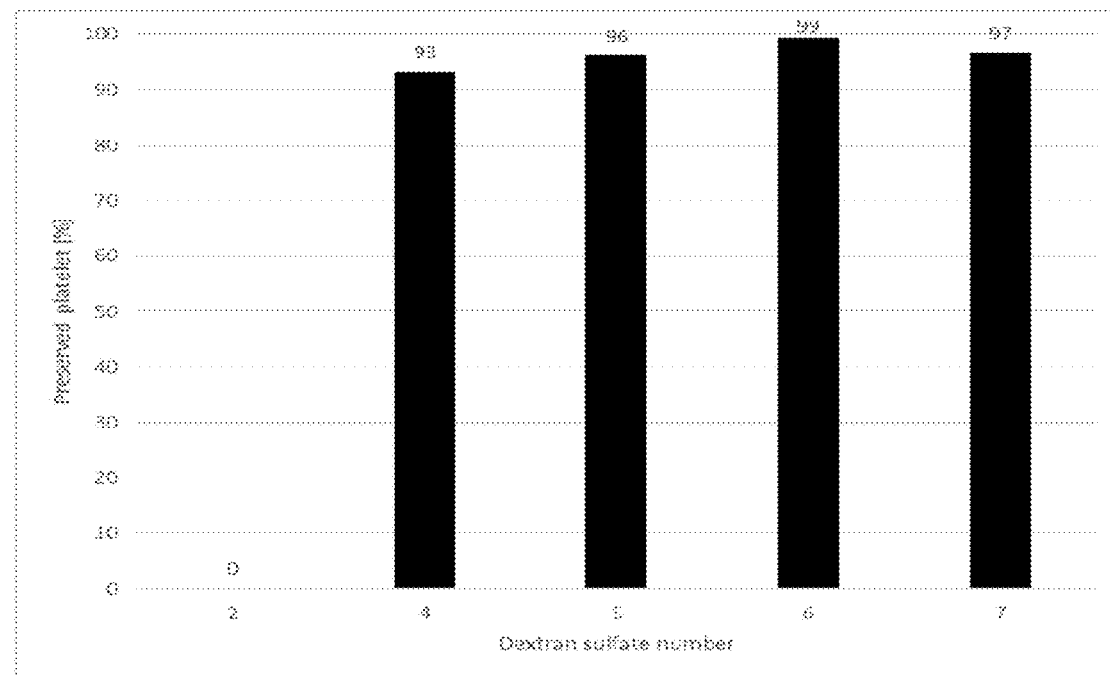
FIG. 14: shows preserved platelets (%) for PVC tubing coated with dextran sulfates 2, 4, 5, 6 and 7 at 0.25 M NaCl concentration.
Figure 15:
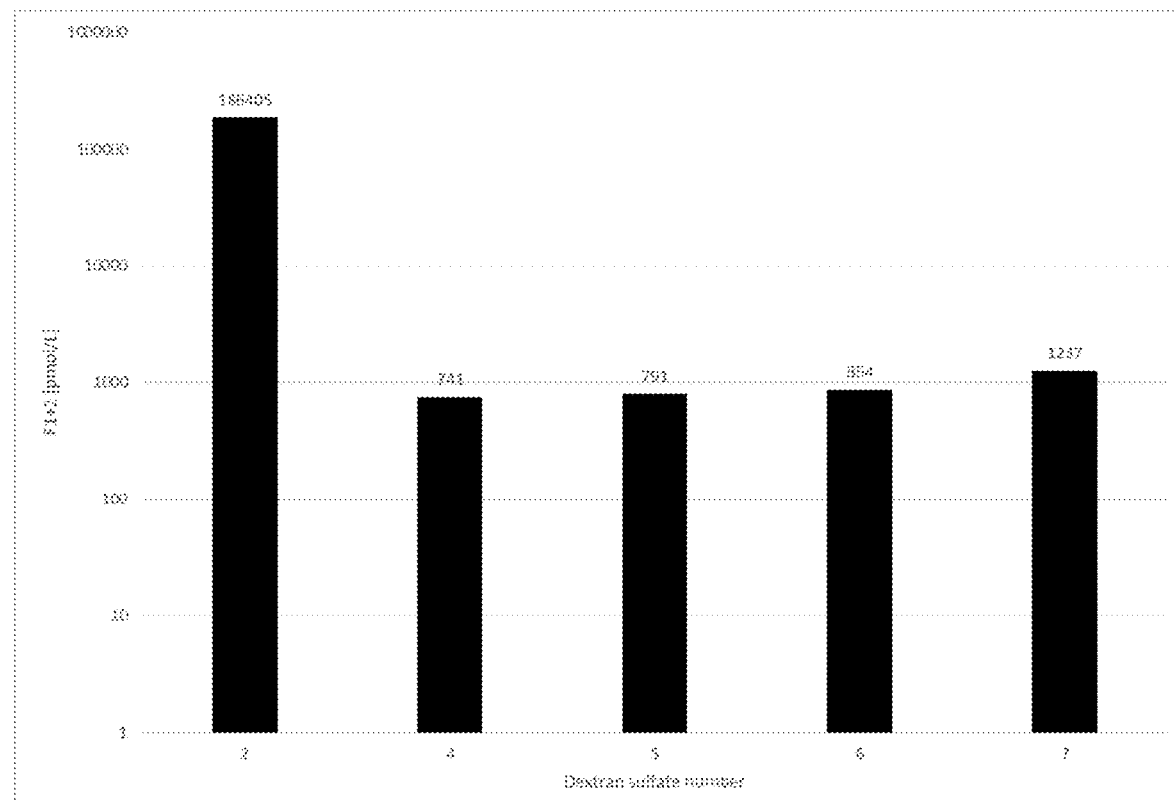
FIG. 15: shows F1+2 (prothrombin fragment) for PVC tubing coated with dextran sulfates 2, 4, 5, 6 and 7 at 0.25 M NaCl concentration.
Figure 16:
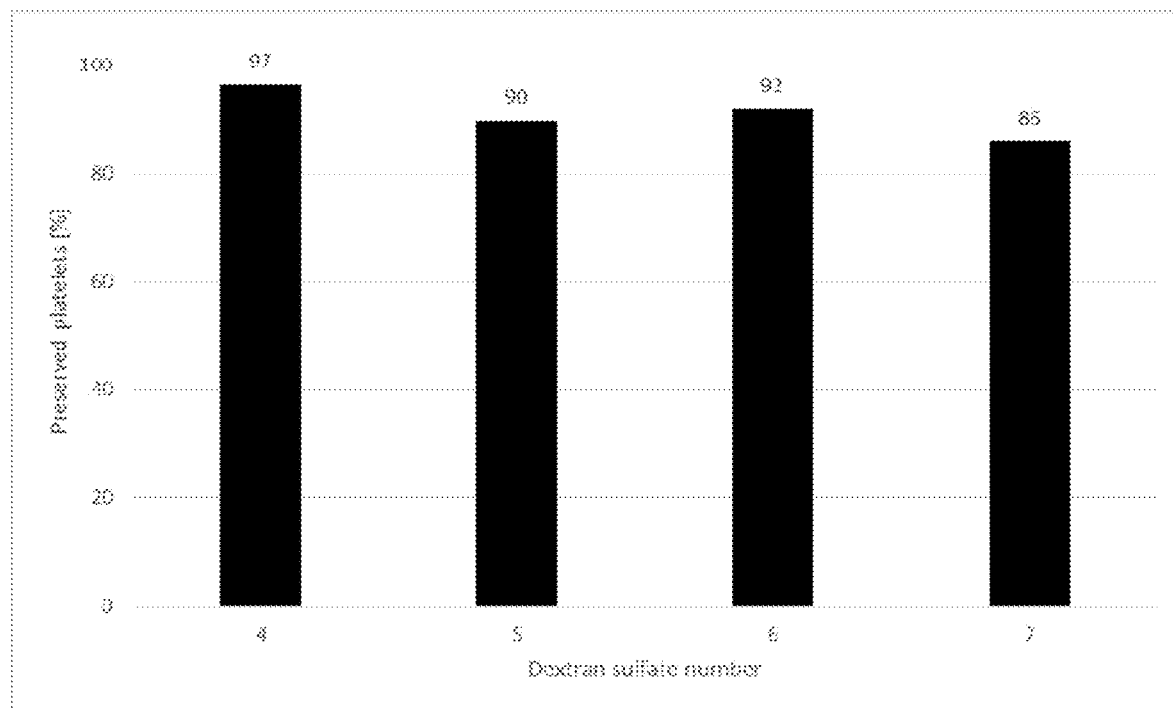
FIG. 16: shows preserved platelets (%) for PVC tubing coated with dextran sulfates 4, 5, 6 and 7 at 1.7 M NaCl concentration.
Figure 17:
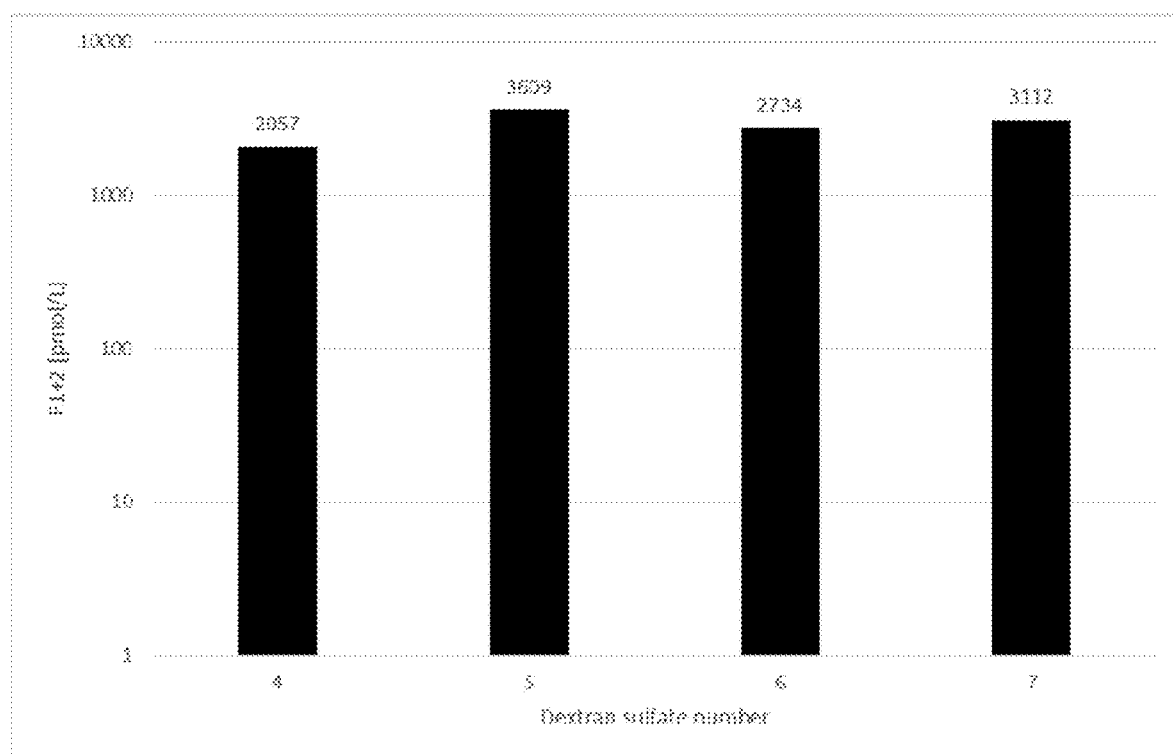
FIG. 17: shows F1+2 (prothrombin fragment) for PVC tubing coated with dextran sulfates 4, 5, 6 and 7 at 1.7 M NaCl concentration.

The results are shown in Table 15 and FIGS. 14 and 15 (0.25 M NaCl concentration) and Table 16 and FIGS. 16 and 17 (1.7 M NaCl concentration).

As seen in the Tables and Figures, no significant platelet loss (platelet loss indicating thrombosis) was observed for solid objects coated according to the process of the invention with dextran sulfates 4, 5, 6 and 7 at 0.25 M and 1.7 M NaCl concentration. The thromboresistant properties of the coatings were further confirmed by the low F1+2 values (prothrombin fragment) observed for the same dextran sulfates. The tubing coated with comparative dextran sulfate 1 with molecular weight of 50 kDa and with comparative dextran sulfate 2 with molecular weight of 100 kDa also showed significant thrombosis and high generation of prothrombin fragments compared with solid objects of the invention coated with dextran sulfates 4-7.

The uncoated PVC tubing and the clotting example show significant thrombosis in this experiment.

TABLE 15

Preserved platelets (%) and F1 + 2 (pmol/L) of PVC tubing coated with dextran sulfates 1, 2, 4, 5, 6 and 7 at 0.25M NaCl concentration

| Example No. | Dextran sulfate No. | Preserved platelets [%] | F1 + 2 [pmol/L] | N (number average) |
|---|---|---|---|---|
| 1.1 | 1 (Reference example dextran sulfate) | 53 | 15868 | 2 |
| 1.3 | 2 (Reference example dextran sulfate) | 0 | 186405 | 1 |
| 1.13 | 4 | 93 | 741 | 1 |
| 1.18 | 5 | 96 | 791 | 1 |
| 1.25 | 6 | 99 | 854 | 2 |
| 1.31 | 7 | 97 | 1237 | 2 |
| Uncoated PVC example | — | 2 | 637658 | — |
| Clotting example | — | 1 | 644465 | — |

TABLE 16

Preserved platelets (%) and F1 + 2 (pmol/L) of PVC tubing coated with dextran sulfates 1, 4, 5, 6 and 7 at 1.7M NaCl concentration

| Example No. | Dextran sulfate No. | Preserved platelets [%] | F1 + 2 [pmol/L] | N (number average) |
|---|---|---|---|---|
| 1.2 | 1 (Reference example dextran sulfate) | 27 | 248469 | 2 |
| 1.15 | 4 (Reference example dextran sulfate) | 97 | 2057 | 2 |
| 1.22 | 5 | 90 | 3609 | 3 |
| 1.27 | 6 | 92 | 2734 | 1 |
| 1.35 | 7 | 86 | 3112 | 1 |
| Uncoated PVC example | — | 2 | 637658 | — |
| Clotting example | — | 1 | 644465 | — |

Example 6: Toluidine Blue Staining of Coated PVC and PUR Tubing and Steel Coupons Using Different Dextran Sulfates at Varied Salt Concentration PVC and PUR tubing and steel coupons coated according to Examples 1.1-1.55 were subjected to a toluidine blue staining test as set out in Evaluation Method C.

A blue/violet color was observed on the luminal surface of the tubing and steel coupons indicating the covalent attachment of end-point functionalized heparin. The homogenous staining obtained for tested solid objects coated according to the process of the invention indicates formation of a uniform coating (in particular uniform heparin distribution) which may be obtained using different dextran sulfates at salt different concentrations, on different solid objects.

Figure 18:
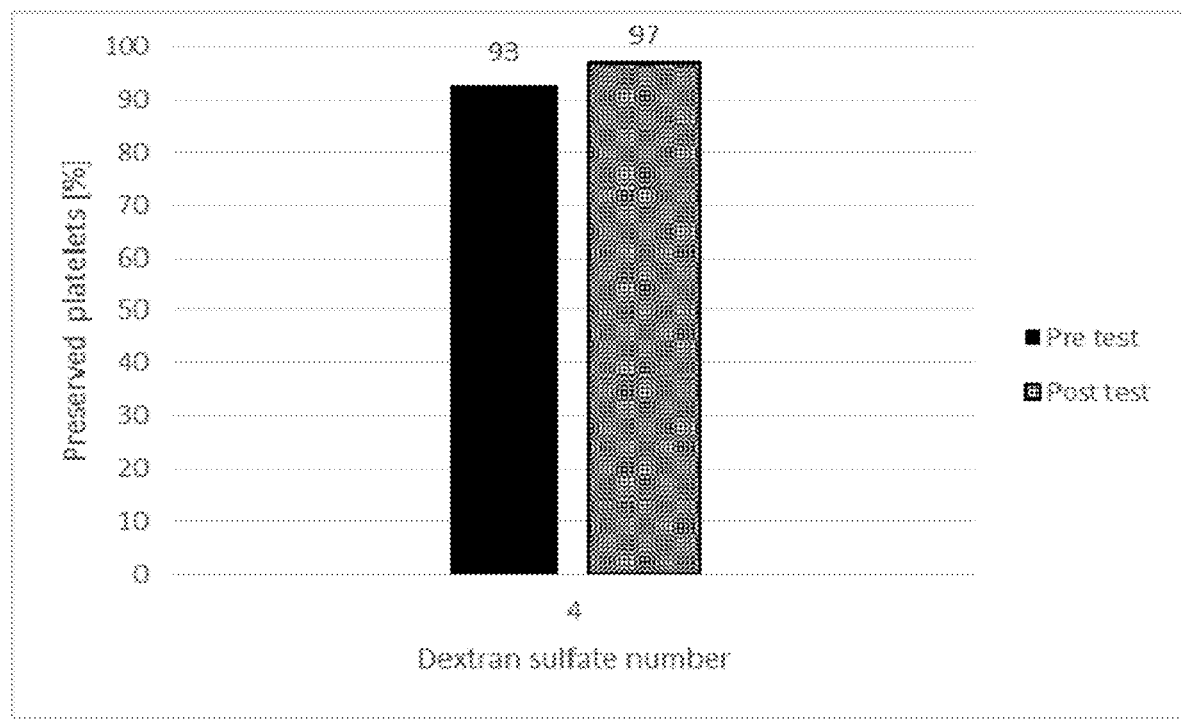
FIG. 18: shows preserved platelets (%) for PVC tubing coated with dextran sulfate 4 at 0.25 M NaCl concentration, pre- and post-temperature and humidity test.
Figure 19:
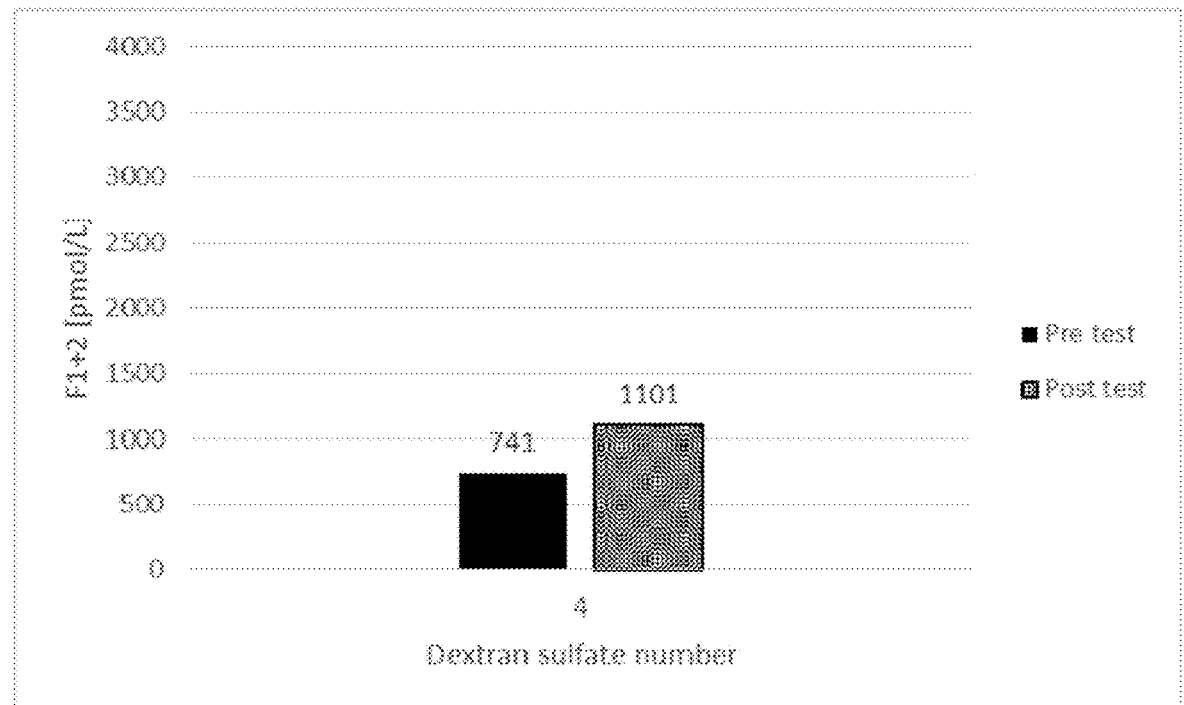
FIG. 19: shows F1+2 (prothrombin fragment) for PVC tubing coated with dextran sulfate 4 at 0.25 M NaCl concentration, pre- and post-temperature and humidity test.
Figure 20:
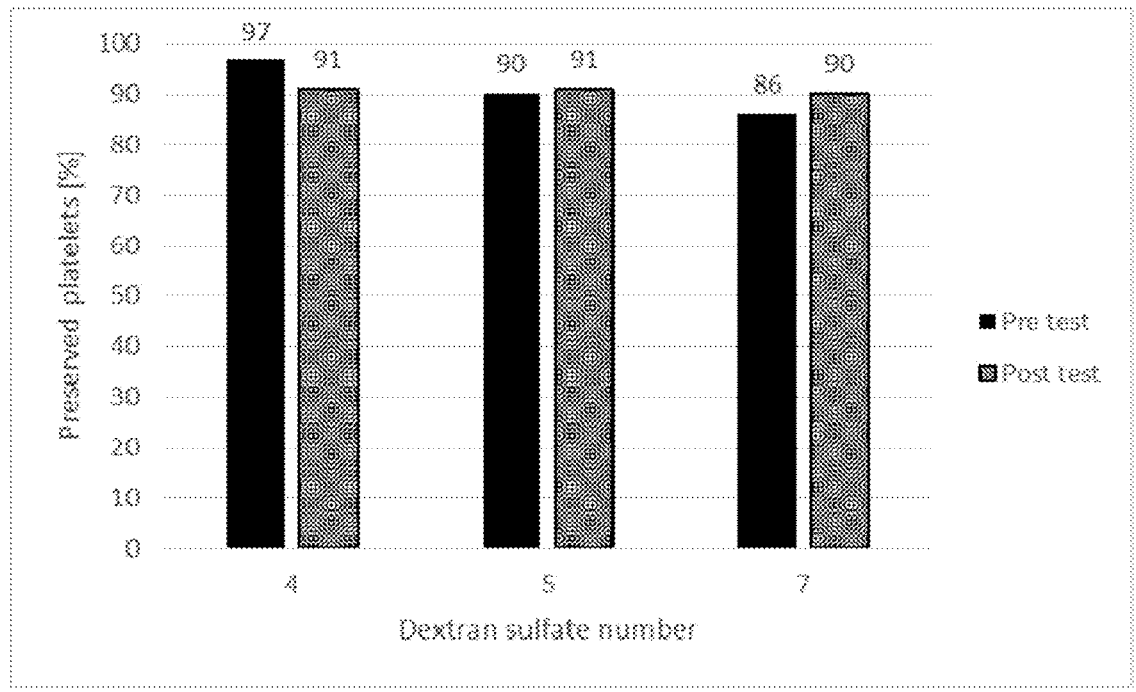
FIG. 20: shows preserved platelets (%) for PVC tubing coated with dextran sulfates 4, 5 and 7 at 1.7 M NaCl concentration, pre- and post-temperature and humidity test.
Figure 21:
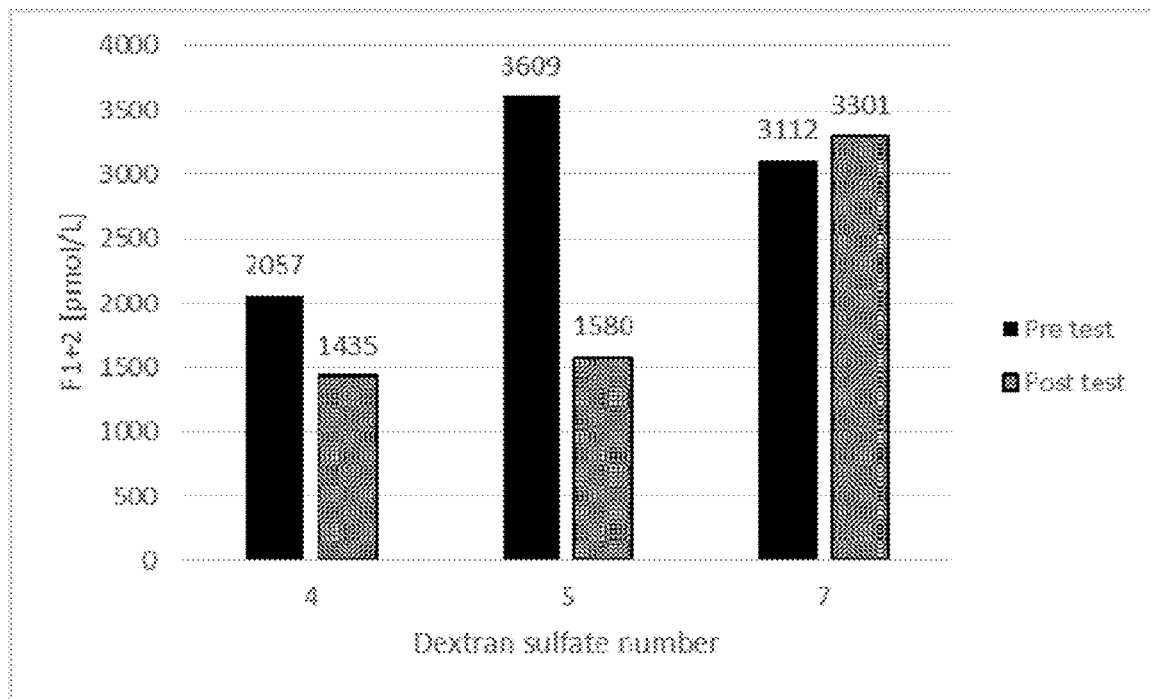
FIG. 21: shows F1+2 (prothrombin fragment) for PVC tubing coated with dextran sulfates 4, 5 and 7 at 1.7 M NaCl concentration, pre- and post-temperature and humidity test.

Example 7: Blood Contact Activation (Platelet Loss and F1+2) of Coated PVC Tubing—Post Temperature and Humidity Test PVC tubing coated according to Examples 1.13, 1.15, 1.22 and 1.35 (corresponding to dextran sulfates 4, 5, and 7)) at varied NaCl concentration was exposed to increased temperature and relative humidity (40° C., 50% RH, 1 week, according to Evaluation Method K) prior to evaluation according to Evaluation Methods E (preserved platelets) and F (F1+2). The results are shown in Table 17 and FIGS. 18 and 19, and Table 18 and FIGS. 20 and 21.

As seen in the Tables and Figures, for solid objects coated according to the process of the invention using dextran sulfates 4, 5 and 7, there is no significant change in the preserved platelet and F1+2 values post exposure to increased temperature and humidity. Similar results were obtained for solid objects coated according to the process of the invention using dextran sulfates 4, 5 and 7 prepared at 0.25 M and 1.7 M NaCl concentration.

These results demonstrate that the thromboresistant properties of the coated solid objects prepared according to the process of the invention are retained in spite of exposure to rigorous conditions as increased temperature and humidity.

TABLE 17

Preserved platelets (%) and F1 + 2 (pmol/L) of PVC tubing coated with dextran sulfate 4 at 0.25M NaCl concentration - before and after exposure to increased temperature and humidity

| Exposure to 40° C. 50% RH, 1 week | Example No. | Dextran sulfate No. | Preserved platelets [%] | F1 + 2 [pmol/L] | N (number average) |
|---|---|---|---|---|---|
| Pre | 1.13 | 4 | 93 | 741 | 1 |
| Post |  | 4 | 97 | 1101 | 1 |
| Pre | Uncoated PVC example | — | 2 | 332748 | — |
| Post |  |  |  |  |  |
| Pre | Clotting example | — | 1 | 853981 | — |
| Post |  |  |  |  |  |

TABLE 18

Preserved platelets (%) and F1 + 2 (pmol/L) of PVC tubing coated with dextran sulfates 4, 5 and 7 at 1.7M NaCl concentration - before and after exposure to increased temperature and humidity

| Exposure to 40° C. 50% RH, 1 week | Example No. | Dextran sulfate No. | Preserved platelets [%] | F1 + 2 [pmol/L] | N (number average) |
|---|---|---|---|---|---|
| Pre | 1.15 | 4 | 97 | 2057 | 2 |
| Post |  | 4 | 91 | 1435 | 1 |
| Pre | 1.22 | 5 | 90 | 3609 | 3 |
| Post |  | 5 | 91 | 1580 | 1 |
| Pre | 1.35 | 7 | 86 | 3112 | 1 |
| Post |  | 7 | 90 | 3301 | 1 |
| Pre | Uncoated PVC example | — | 1 | 619778 | — |
| Post |  |  |  |  |  |
| Pre | Clotting example | — | 2 | 768361 | — |
| Post |  |  |  |  |  |

All patents and patent applications referred to herein are incorporated by reference in their entirety.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A process for the manufacture of a solid object having a thromboresistant surface comprising a layered coating of cationic and anionic polymer wherein the outer coating layer comprises an anticoagulant entity, comprising the steps of:
   i) treating a surface of the solid object with a cationic polymer;
   ii) treating the surface with an anionic polymer;
   iii) optionally repeating steps i) and ii) one or more times;
   iv) treating the surface with a cationic polymer; and
   v) treating the outermost layer of cationic polymer with an anticoagulant entity to covalently attach the anticoagulant entity to the outermost layer of cationic polymer;
   wherein
   the anionic polymer is characterized by having a total molecular weight of 650 kDa-10,000 kDa;
   the sulfur content of the anionic polymer is between 15% and 25% by weight of the anionic polymer;
   the anionic polymer is dextran sulfate;
   and wherein
   step ii) is carried out at a salt concentration of 0.25 M-3.0 M.

2. A process for the manufacture of a solid object according to claim 1, wherein the anionic polymer is characterized by having a total molecular weight of 750 kDa-10,000 kDa.

3. A process for the manufacture of a solid object according to claim 1, wherein step ii) is carried out at a salt concentration of 0.25 M-2.6 M.

4. A process for the manufacture of a solid object according to claim 1, wherein the sulfur content of the anionic polymer is between 15% and 20% by weight of the anionic polymer.

5. A process for the manufacture of a solid object according to claim 1, wherein the salt is selected from the group consisting of sodium chloride, sodium sulfate, sodium hydrogen phosphate and sodium phosphate.

6. A process for the manufacture of a solid object according to claim 5, wherein the salt is sodium chloride.

7. A process for the manufacture of a solid object according to claim 1, wherein the cationic polymer of step i) is a polyamine.

8. A process for the manufacture of a solid object according to claim 1, wherein the cationic polymer of step iv) is a polyamine.

9. A process for the manufacture of a solid object according to claim 1, wherein the anticoagulant entity is a heparin moiety.

10. A process for the manufacture of a solid object according to claim 9, wherein the heparin moiety is an end-point attached heparin moiety.

11. A process for the manufacture of a solid object according to claim 10, wherein the end-point attached heparin moiety is connected through its reducing end.

12. A process for the manufacture of a solid object according to claim 1, wherein the anticoagulant entity is covalently attached via a linker.

* * * * *